United States Patent [19]
Claremon et al.

[11] Patent Number: 5,389,631
[45] Date of Patent: Feb. 14, 1995

[54] FIBRINOGEN RECEPTOR ANTAGONISTS

[75] Inventors: David A. Claremon, Maple Glen; Nigel Liverton, Harleysville, both of Pa.

[73] Assignee: Merck & Co., Inc., Rahway, N.J.

[21] Appl. No.: 34,042

[22] Filed: Mar. 22, 1993

Related U.S. Application Data

[63] Continuation-in-part of Ser. No. 821,116, Jan. 15, 1992, Pat. No. 5,272,158, which is a continuation-in-part of Ser. No. 784,484, Oct. 29, 1991, abandoned.

[51] Int. Cl.⁶ .................. A61K 31/55; A61K 31/505; C07D 243/14; C07D 239/80
[52] U.S. Cl. .................. 514/221; 514/259; 544/284; 544/285; 540/570
[58] Field of Search .............. 544/285, 284; 514/259, 514/221; 540/570

[56]  References Cited
U.S. PATENT DOCUMENTS

| | | | |
|---|---|---|---|
| 4,122,255 | 10/1978 | Krapcho | 544/160 |
| 4,243,807 | 1/1981 | Frieb et al. | 546/232 |
| 4,313,947 | 2/1982 | Nakagawa et al. | 424/248.54 |
| 4,622,331 | 11/1986 | Jozic | 514/331 |
| 5,030,654 | 7/1991 | Barnish | 514/510 |

FOREIGN PATENT DOCUMENTS

| | | |
|---|---|---|
| 0229391 | 7/1987 | European Pat. Off. . |
| 0352249 | 1/1990 | European Pat. Off. . |
| 0372486 | 6/1990 | European Pat. Off. . |
| 0381033 | 8/1990 | European Pat. Off. . |
| 0384362 | 8/1990 | European Pat. Off. . |
| 0405537 | 1/1991 | European Pat. Off. . |

*Primary Examiner*—Raymond J. Henley, III
*Assistant Examiner*—Phyllis G. Spivack
*Attorney, Agent, or Firm*—Richard S. Parr; Melvin Winokur; Paul D. Matukaitis

[57] ABSTRACT

Fibrinogen receptor antagonists of the

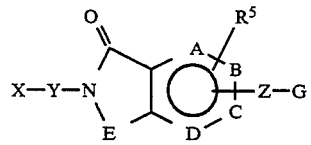

are disclosed for use in inhibiting the binding of fibrinogen to blood platelets and for inhibiting the aggregation of blood platelets wherein G is:

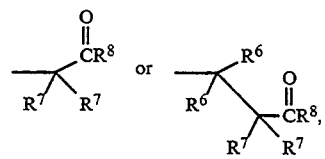

for example,

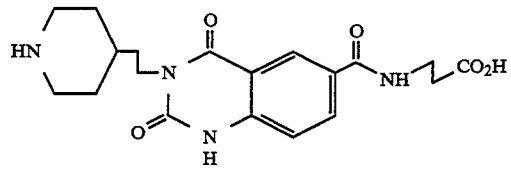

11 Claims, No Drawings

FIBRINOGEN RECEPTOR ANTAGONISTS

CROSS-REFERENCE

This application is a continuation-in-part of U.S. Ser. No. 821,116, filed Jan. 15, 1992, now U.S. Pat. No. 5,272,158, which is a continuation-in-part of U.S. Ser. No. 07/784,484, filed Oct. 29, 1991, abandoned.

FIELD OF THE INVENTION

This invention relates to the discovery of fibrinogen receptor antagonists of Formula I for use in inhibiting the binding of fibrinogen to blood platelets and inhibiting the aggregation of blood platelets when administered to mammals, preferably humans.

BACKGROUND OF THE INVENTION

The interaction of platelets with the coagulation and fibrinolytic systems in the maintenance of hemostasis may become pathogenic, requiring prevention and treatment. The fibrinogen receptor antagonists of Formula I are useful in treating various diseases related to platelet aggregation and fibrin formation.

An interest in platelet inhibitors has reemerged as a result of a better understanding of the role of platelets and thrombosis in the pathogenesis of vascular disease, including unstable angina, acute myocardial infarction and stroke.

Platelets are cell-like anucleated fragments, found in the blood of all mammals which participate in blood coagulation. Fibrinogen is a glycoprotein present as a normal component of blood plasma. Fibrinogen participates in platelet aggregation and fibrin formation in the blood clotting mechanism. Platelets are deposited at sites of vascular injury where multiple physiological agonists act to initiate platelet aggregation culminating in the formation of a platelet plug to minimize blood loss. If the platelet plug occurs in the lumen of a blood vessel, normal blood flow is impaired.

Platelet membrane receptors are essential in the process of platelet adhesion and aggregation. Interaction of fibrinogen with a receptor on the platelet membrane complex IIb/IIIa is known to be essential for normal platelet function.

Zimmerman et al., U.S. Pat. No. 4,683,291, describes peptides having utility in the study of fibrinogen-platelet, platelet-platelet, and cell-cell interactions. The peptides are described as having utility where it is desirable to retard or prevent formation of a thrombus or clot in the blood. The general formula for the peptides includes an Arg-Gly-Asp sequence.

Tjoeng et al., EP 352,249, describe platelet aggregation inhibitors which antagonize interactions between fibrinogen and/or extracellular matrix proteins and the platelet gpIIb/IIIa receptor, including 8-guanido-octanoyl-Asp-2-(4-methoxyphenyl)ethyl amide.

Alig et al., EP 372,486, describe N-aryl beta-amino acids which inhibit fibrinogen, fibronectin and von Willebrand factor to the blood platelet fibrinogen receptor (glyco-protein IIb/IIIa).

Alig et al., EP 381,033, describe di-aryl or heteroaryl substituted alkanoic acid derivatives of a defined formula which inhibit binding of proteins to their specific receptors on cell surfaces, including fibrinogen.

Alig et al., EP 384,362, describe glycine peptides of a specified formula containing an amidine group which inhibit binding of fibrinogen to platelet fibrinogen receptors.

Horwell et al., EP 405,537, describe N-substituted cycloalkyl and polycycloalkyl alpha-substituted Trp-Phe- and phenethylamine derivatives which are useful for treating obesity, hypersecretion of gastric acid in the gut, gastrin-dependent ramors, or as antipsychotics.

It is an object of the present invention to provide fibrinogen receptor antagonists for use in inhibiting the binding of fibrinogen to blood platelets and inhibiting the aggregation of blood platelets. Another aspect of the present invention is to provide novel fibrinogen receptor antagonist compounds. Other objects of the present invention are to provide methods of inhibiting the binding of fibrinogen to blood platelets and inhibiting the aggregation of blood platelets, through the administration of novel fibrinogen receptor antagonist compounds. The above and other objects are accomplished by the present invention in the manner described below.

SUMMARY OF THE INVENTION

The present invention provides fibrinogen receptor antagonist compounds of the formula:

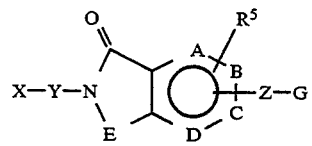

wherein G is

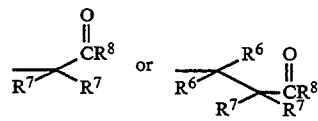

for use in inhibiting the binding of fibrinogen to blood platelets and for inhibiting the aggregation of blood platelets. The above-mentioned compounds can be used in a method of acting upon a fibrinogen receptor which comprises administering a therapeutically effective but non-toxic amount of such compound to a mammal, preferably a human. A pharmaceutical composition comprising a pharmaceutically acceptable carrier and, dispersed therein, an effective but non-toxic amount of such compound is another feature of this invention.

DETAILED DESCRIPTION OF THE INVENTION

Fibrinogen receptor antagonist compounds of Formula I are useful in a method of inhibiting the binding of fibrinogen to blood platelets and for inhibiting the aggregation of blood platelets. Fibrinogen receptor antagonists of this invention are illustrated by compounds having the formula:

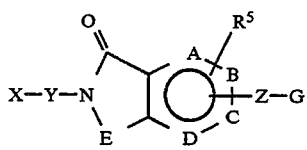

wherein G is

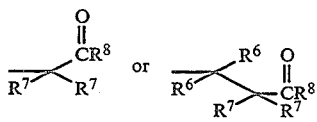

wherein:

A, B, C and D independently represent a carbon atom or a nitrogen atom;

E is —(CHR$^1$)$_m$—(CHR$^2$)$_n$—F—(CHR$^3$)$_o$—(CHR$^4$)$_p$—; or —(CHR$^1$)$_m$—CR$^2$=N—(CHR$^4$)$_n$—, wherein m, n, o, and p are integers chosen from 0–2; and F is chosen from:

O, —CR$^1$R$^2$—,

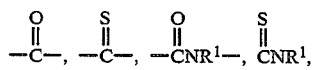

(CH$_2$)$_{0-2}$,

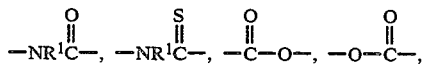

or —NR$^1$R$^2$;

X is
—NR$^1$R$^2$,

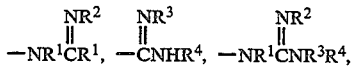

or a 4- to 10- membered mono- or polycyclic aromatic or nonaromatic ring system containing 0, 1, 2, 3 or 4 heteroatoms selected from N, O and S and either unsubstituted or substituted with R$^1$, R$^2$, R$^3$ or R$^4$, wherein R$^1$, R$^2$, R$^3$ and R$^4$ are independently selected from the group consisting of hydrogen, C$_{1-10}$ alkyl aryl C$_{0-8}$ alkyl, oxo, thio, amino C$_{0-8}$ alkyl, C$_{1-3}$ acylamino C$_{0-8}$ alkyl, C$_{1-6}$ alylamino C$_{0-8}$ alkyl, C$_{1-6}$ dialkylamino C$_{0-8}$ alkyl, C$_{1-4}$ alkoxy C$_{0-6}$ alkyl, carboxy C$_{0-6}$ alkyl, C$_{1-3}$ alkoxycarbonyl C$_{0-6}$ alkyl, carboxy C$_{0-6}$ alkyloxy, hydroxy C$_{0-6}$ alkyl, and fused or nonfused heteroaryl C$_{0-8}$ alkyl, wherein the heteroaryl group contains 1, 2, 3 or 4 heteroatoms N, O, or S;

Y is C$_{0-8}$ alkyl, C$_{0-8}$ alkyl—NR$^3$—CO—C$_{0-8}$ alkyl, C$_{0-8}$ alkyl—CONR$^3$—C$_{0-8}$ alkyl, C$_{0-8}$ alkyl—O—C$_{0-8}$ alkyl, C$_{0-8}$ alkyl—S(O$_n$)—C$_{0-8}$ alkyl, or C$_{0-8}$ alkyl—SO$_2$—NR$^3$—C$_{0-8}$ alkyl—, C$_{0-8}$ alkyl—NR$^3$—SO$_2$—C$_{0-8}$ alkyl—, C$_{1-8}$ alkyl—CO—C$_{0-8}$ alkyl;

Z is

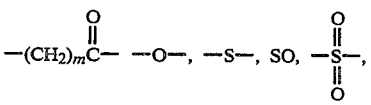

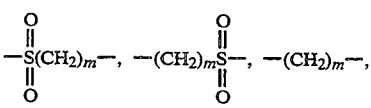

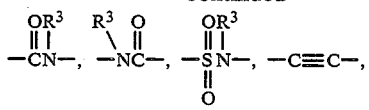

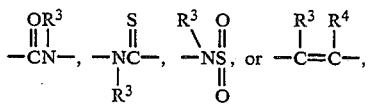

wherein m is 0–6;

R$^5$ is hydrogen C$_{1-6}$ alkyl, C$_{0-6}$ alkylcarboxy C$_{0-6}$ alkyl, C$_{0-6}$ alkyloxy C$_{0-6}$ alkyl, hydroxy C$_{0-6}$ alkyl, aryl C$_{0-6}$ alkyl, or halogen;

R$^6$ is hydrogen, C$_{1-8}$ alkyl, aryl C$_{0-6}$ alkyl, C$_{3-8}$ cycloalkyl C$_{0-6}$ alkyl, C$_{0-6}$ alkylcarboxy C$_{0-6}$ alkyl, carboxy C$_{0-6}$alkyl, C$_{1-4}$ alkyloxy C$_{0-6}$ alkyl, hydroxy C$_{0-6}$ alkyl, provided that any of which groups may be substituted or unsubstituted independently with R$^1$ or R$^2$, and provided that, when two R$^6$ groups are attached to the same carbon, they may be the same or different;

R$^7$ is hydrogen, fluorine C$_{1-8}$ alkyl, C$_{3-8}$ cycloalkyl, aryl C$_{0-6}$ alkyl, C$_{0-6}$ alkylamino C$_{0-6}$ alkyl, C$_{0-6}$ dialkylamino C$_{0-6}$ alkyl, C$_{1-8}$ alkylsulfonylamino C$_{0-6}$ alkyl, aryl C$_{0-6}$ alkylsulfonylamino C$_{0-6}$ alkyl, C$_{1-8}$ alkyloxycarbonylamino C$_{0-8}$-alkyl, aryl C$_{0-8}$ alkyloxycarbonylamino C$_{0-8}$ alkyl, C$_{1-8}$ alkylcarbonylamino C$_{0-6}$ alkyl, aryl C$_{0-6}$ alkylcarbonylamino C$_{0-6}$ alkyl, C$_{0-8}$ alkylaminocarbonylamino C$_{0-6}$ alkyl, aryl C$_{0-8}$ alkylaminocarbonylamino C$_{0-6}$ alkyl, C$_{1-6}$ alkylsulfonyl C$_{0-6}$ alkyl, aryl C$_{0-6}$ alkylsulfonyl C$_{0-6}$ alkyl, C$_{1-6}$ alkylcarbonyl C$_{0-6}$ alkyl aryl C$_{0-6}$ alkylcarbonyl C$_{0-6}$ alkyl, C$_{1-6}$ alkylthiocarbonylamino C$_{0-6}$ alkyl aryl C$_{0-6}$ alkylthiocarbonylamino C$_{0-6}$ alkyl wherein groups may be unsubstituted or substituted with one or more substituents selected from R$^1$ and R$^2$, and provided that when two R$^7$ groups are attached to the same carbon atom, they may be the same or different;

R$^8$ is hydroxy, C$_{1-8}$ alkyloxy, aryl C$_{0-6}$ alkyloxy, C$_{1-8}$ alkylcarbonyloxy C$_{1-4}$ alkyloxy, aryl C$_{1-8}$ alkylcarbonyloxy C$_{1-4}$ alkyloxy, or an L- or D-amino acid joined by an amide linkage and wherein the carboxylic acid moiety of said amino acid is as the free acid or is esterified by C$_{1-6}$ alkyl.

When substituent R$^1$, R$^2$, R$^3$, R$^4$, R$^5$, R$^6$, R$^7$, R$^8$ or Y includes the definition C$_0$, (e.g. aryl C$_0$alkyl), the group modified by C$_0$ is not present in the substituent.

"Aryl" means a mono- or polycyclic system composed of 5- and 6- membered aromatic rings containing 0, 1, 2, 3 or 4 heteroatoms chosen from N, O or S and either unsubstituted or substituted with R$^1$.

"Alkyl" means straight or branched chain alkane, alkene or alkyne.

"Halogen" includes fluorine, chlorine, iodine and bromine.

"Oxo" means=O.

"Thio" means=S.

A preferred embodiment of the present invention is

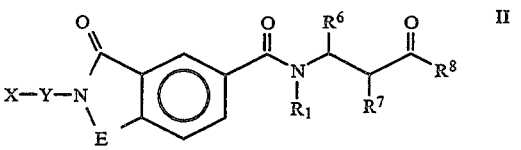

wherein:

E is —(CHR$^1$)$_m$—(CHR$^2$)$_n$—F—(CHR$^3$)$_o$—(CHR$^4$)$_p$—; or —(CHR$^1$)$_m$—CR$^2$=N—(CHR$^4$)$_n$, where m, n, o and p are integers 0–2, F is chosen from: O, —CR$^1$R$^2$—, $$-\overset{O}{\underset{\|}{C}}-,\ -\overset{S}{\underset{\|}{C}}-,\ -\overset{O}{\underset{\|}{C}}NR^1-,$$

(CH$_2$)$_{0-2}$, $$-NR^1\overset{O}{\underset{\|}{C}}-,\ -\overset{O}{\underset{\|}{C}}-O-,\ -O-\overset{O}{\underset{\|}{C}}-,$$

or —NR$^1$R$^2$; and X, Y, R$^1$, R$^2$, R$^3$, R$^4$, R$^6$, R$^7$ and R$^8$ are as previously defined.

A more preferred embodiment of the present invention is

II wherein:

E is —(CHR$^1$)$_m$—F—(CHR$^2$)$_n$—, where m and n are integers 0–2 and

F is $$-\overset{O}{\underset{\|}{C}}NR^1-;$$

X is —NR$^1$R$^2$ or a 4- to 10-membered mono- or polycyclic aromatic or non-aromatic ring system containing 0, 1 or 2 heteroatoms chosen from N or O and either unsubstituted or substituted with R$^1$ and R$^2$, wherein R$^1$ and R$^2$ are independently chosen from: hydrogen, C$_{1-6}$ alkyl, aryl C$_{0-6}$ alkyl, carboxy C$_{0-6}$ alkyl, hydroxy C$_{0-6}$ alkyl, C$_{1-3}$ alkyloxy C$_{0-6}$ alkyl, or amino C$_{0-6}$ alkyl;

Y is C$_{0-6}$ alkyl, C$_{1-6}$ alkyl—CO—C$_{0-6}$ alkyl, or C$_{0-6}$ alkyl—NR$^3$—CO—C$_{0-6}$ alkyl;

R$^6$ and R$^7$ are as previously defined and

R$^8$ is hydroxy, C$_{1-6}$ alkyloxy, aryl C$_{1-4}$ alkyloxy, or C$_{1-6}$ alkylcarbonyloxy C$_{1-4}$ alkyloxy.

An even more preferred embodiment of the present invention is wherein:

$$-\overset{O}{\underset{\|}{C}}-NH;\ CH_2\overset{O}{\underset{\|}{C}}-NH-;\ -\overset{O}{\underset{\|}{C}}-\underset{\underset{H_5C_6}{|}}{N}-;$$

-continued $$-\overset{O}{\underset{\|}{C}}-\underset{\underset{CH_3}{|}}{N}-;\ -\overset{O}{\underset{\|}{C}}-\underset{|}{N}-;\ or\ -\underset{\underset{CH_3}{|}}{C}=N-;$$

and X, Y, R$^1$, R$^2$, R$^3$, R$^6$, R$^7$ and R$^8$ are as previously defined.

Especially preferred compounds of the invention are:

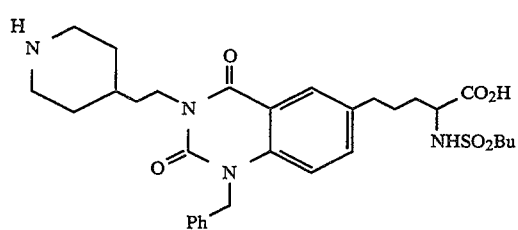
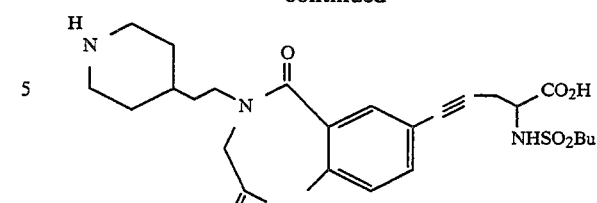
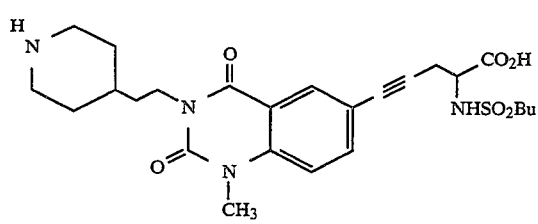
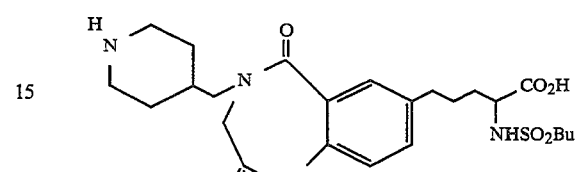
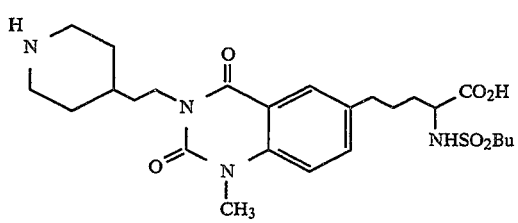
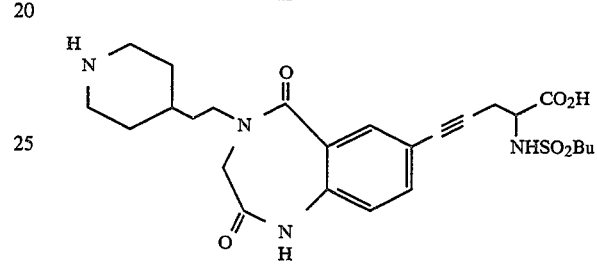
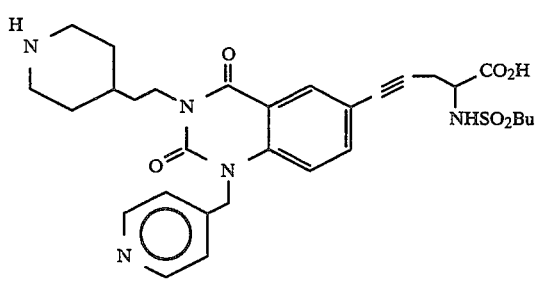
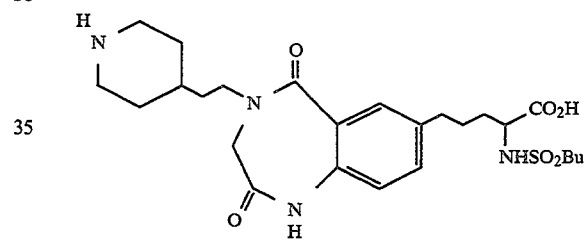
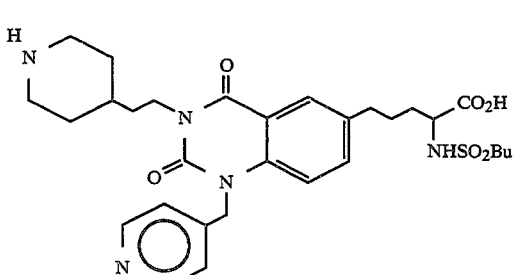
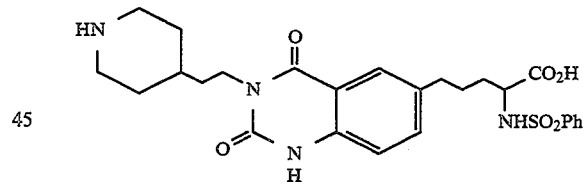
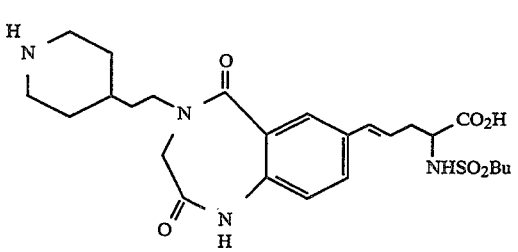
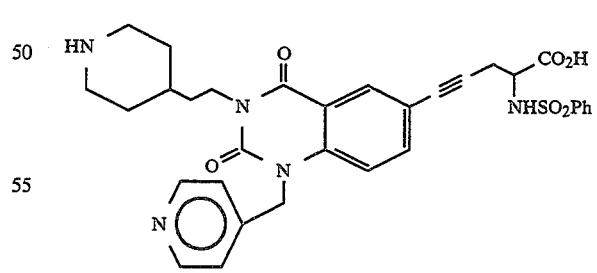
The portion of certain structures represented by "—≡—", which appears above and throughout the application, means "—C≡C—".
Generally, compounds of the present invention can be made according to a procedure including the following steps:
a) preparing a triflate activated aromatic group of the following general formula:

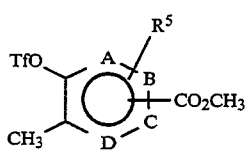

using

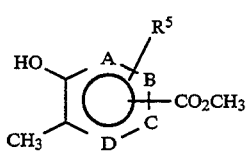

and Tf₂O;

b) inserting a carbonyl group for the triflate group using metal catalyzed carbonyl insertion, followed by trapping with methanol, to form

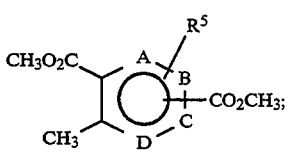

c) brominating the heterocyclic methyl group to form

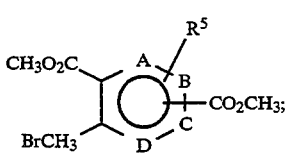

d) cyclizing with a primary amine to form

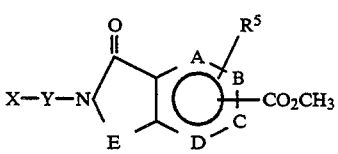

wherein X is an N-terminus protected primary amine, or a primary amine protected directly following this cyclization step;

e) converting the C-terminus ester, via hydrolysis, to an acid

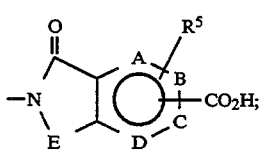

f) coupling the acid with an unsubstituted or substituted amino acid or C-terminus protected analog, or diamino acid or C-terminus protected analog, and optionally functionalizing the amino-acid at the alpha- or beta-position, to form

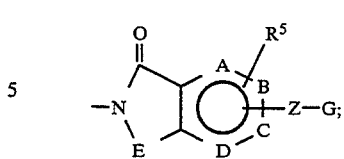

g) deprotecting the protected C-terminus and N-terminus.

Preferably the procedure involves a) preparing an activated aryl group:

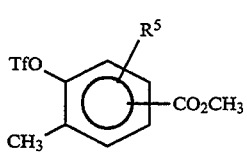

using

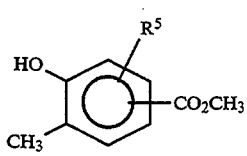

and T₂O;

b) inserting a carbonyl group for the triflate group using metal catalyzed carbonyl insertion followed by trapping with methanol to form

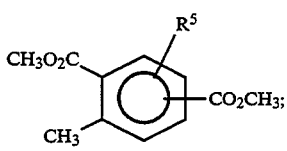

c) brominating the aryl methyl group to form

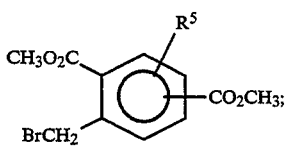

d) cyclizing with a primary amine to form

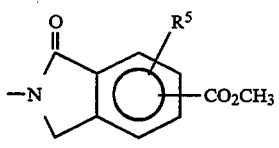

wherein X is an N-terminus protected primary amine, or a primary amine protected directly following this cyclization step;

e) converting the C-terminus ester, via hydrolysis, to an acid

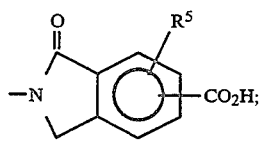

f) coupling the acid with an unsubstituted or substituted amino acid or C-terminus protected analog, or diamino acid or C-terminus protected analog, and optionally functionalizing the amino acid at the alpha- or beta-position via acylation or sulfonylation, to form

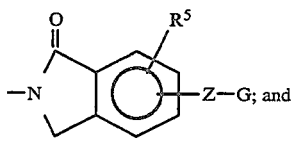

g) deprotecting the protected C-terminus and N-terminus.

An ADP-stimulated platelet aggregation assay was used to determine inhibition associated with compounds of the invention.

Human platelets were isolated from fresh blood, collected into acid citrate/dextrose by differential centrifugation followed by gel filtration on Sepharose 2B in divalent ion-free Tyrode's buffer (pH 7.4) containing 2% bovine serum albumin. Platelet aggregation was measured at 37° C. in a Chronolog aggregometer. The reaction mixture contained gel-filtered human platelets ($2 \times 10^8$ per ml), fibrinogen (100 μg/ml), $Ca^{2+}$ (1 mM), and the compound to be tested. Aggregation was initiated by adding 10 uM ADP 1 minute after the other components had been added. The reaction was allowed to proceed for at least 2 minutes. The extent of inhibition of aggregation was expressed as the percentage of the rate of aggregation observed in the absence of inhibitor. The $IC_{50}$ is the dose of a particular compound inhibiting aggregation by 50% relative to a control lacking the compound.

The abbreviations listed below are defined as Bn, benzyl; NMM, N-methylmorpholine; HOBt, 1-hydroxybenzotriazole; EDC, 1-(3-dimethylaminopropyl)-3-ethylcarbodiimide hydrochloride; DMF, dimethylformamide; Pib, 4-(4-piperidyl)butanoyl; pTSA, para-toluenesulfonic acid; DMS, dimethylsulfide; TFA, trifluoroacetic acid; THF, tetrahydrofuran; DIBAL, diisobutylaluminumhydride; Boc (or BOC), tert-butoxycarbonyl; Cbz, benzyloxycarbonyl; Suc, succinoyl; alpine borane, β-isopinocamphenyl-9-borabicyclo[3.3.1]-nonane; TBDMS, tert-butyldimethylsilyl; Jones reagent, chromic acid; NBS, N-Bromosuccinimide; BPO, Benzoyl peroxide; $PPh_3$, triphenyl phosphine; DMSO, Dimethylsulfoxide; $Et_3N$, triethylamine; $Tf_2O$, triflicanhydride; DMAP, 4-dimethylaminopyridine; BOP, benzotriazol-1-yloxytris(dimethylamino)phosphonium hexafluorophosphate; PhCHO, benzaldehyde; and $Boc_2O$, di-t-butyldicarbonate; dppp, 1,3-bis(diphenylphosphino)propane; ETOH, ethyl acetate; $CH_2Cl_2$, methylene chloride; HOAc, acetic acid; $CH_3OH$, methanol; $CHCl_3$, chloroform.

Unless otherwise indicated, all degree values are Celsius.

The pharmaceutically acceptable salts of the compounds of Formula I include the conventional non-toxic salts or the quarternary ammonium salts of the compounds of Formula I formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula I are also readily prepared by conventional procedures such as treating an acid of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammonium hydroxide and the like.

The compounds of Formula I are useful in inhibiting the binding of fibrinogen to blood platelets, inhibiting aggregation of blood platelets, treatment of thrombus formation or embolus formation, and in the prevention of thrombus formation or embolus formation. These compounds are useful as pharmaceutical agents for mammals, especially for humans. The compounds of this invention may be administered to patients where prevention of thrombosis by inhibiting binding of fibrinogen to the platelet membrane glycoprotein complex IIb/IIIa receptor is desired. Compounds of this invention may also be used to prevent or modulate the progress of myocardial infarction, unstable angina and thrombotic stroke, in either acute or chronic settings. In addition, they may be useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. Compounds of this invention may be administered to surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between GPIIb-/IIIa on the platelet membranes and fibrinogen adsorbed to the surface of the circuit. (Gluszko et al., Amer. J. Physiol., 1987, 252:H, pp 615–621). Platelets released from artificial surfaces show impaired hemostatic function. Compounds of this invention may be administered to prevent adhesion.

Other applications of these compounds include prevention of platelet thrombosis, thromboembolism, reocclusion, and restenosis during and after thrombolytic therapy and prevention of platelet thrombosis, thromboembolism, reocclusion and restenosis after angioplasty of coronary and other arteries and after coronary artery bypass procedures.

The compounds of Formula I may be administered to mammals, preferably in combination with pharmaceutically acceptable carriers or diluents, optionally with known adjuvants such as alum, in a pharmaceutical composition which is non-toxic and in a therapeutically effective amount, according to standard pharmaceutical practice. The compounds can be administered orally or parenterally, including intravenous, intramuscular, intraperitoneal, trans-dermal, subcutaneous and topical administration.

For oral use of a fibrinogen receptor antagonist according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and-/or flavoring agents may be added.

For intramuscular, intraperitoneal, subcutaneous, and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment and prevention of diseases related to platelet aggregation, fibrin formation, and thrombus and embolus formation, comprising the administration of a therapeutically effective but non-toxic amount of the compounds of Formula I, with or without pharmaceutically acceptable carriers or diluents.

Compositions of this invention include fibrinogen receptor antagonist compounds of this invention in combination with pharmacologically acceptable carriers, e.g. saline, at a pH level e.g. 7.4, suitable for achieving inhibition of platelet aggregation. The compositions may also be combined with anticoagulants such as heparin or warfarin. The compositions may also be combined with thrombolytic agents such as plasminogen activators or streptokinase in order to inhibit platelet aggregation in more acute settings. The composition may further be combined with antiplatelet agents such as aspirin. The compositions are soluble in an aqueous medium, and may therefore be effectively administered in solution.

When a compound according to Formula I is used as a fibrinogen receptor antagonist in a human subject, the daily dosage will normally be determined by the prescribing physician with the dosage generally varying according to the age, weight, and response of the individual patient, as well as the severity of the patients symptoms.

In one exemplary application, a suitable amount of compound is administered orally to a heart attack victim subsequent to angioplasty. Administration occurs subsequent to angioplasty, and is in an amount sufficient to inhibit platelet aggregation, e.g. an amount which achieves a steady state plasma concentration of between about 0.01–50 mM preferably between about 0.01–10 mM.

The present invention also includes a pharmaceutical composition comprising compounds of the present invention in combination with tissue type plasminogen activator or streptokinase. The invention also includes a method for promoting thrombolysis and preventing reocclusion in a patient which comprises administering to the patient an effective amount of compositions of the invention.

The present invention provides a method of inhibiting the binding of fibrinogen to blood platelets, inhibiting aggregation of blood platelets, treating thrombus formation or embolus formation, and in preventing thrombus formation or embolus formation in a mammal, comprising the administration of a therapeutically effective but non-toxic amount of the compounds of this invention, with or without pharmaceutically acceptable carriers or diluents.

The present invention still further provides a method of inhibiting the binding of fibrinogen to blood platelets, inhibiting aggregation of blood platelets, treating thrombus formation or embolus formation, and in preventing thrombus formation or embolus formation in a mammal, comprising the administration of a therapeutically effective but non-toxic amounts of the compounds of this invention in combination with thrombolytic agents, such as tissue plasminogen activators or streptokinase, anticoagulants such as heparin or warfarin, or antiplatelet agents such as aspirin, with or without pharmaceutically acceptable carriers or diluents.

The compounds of Formula I are prepared according to the reaction schemes set forth below.

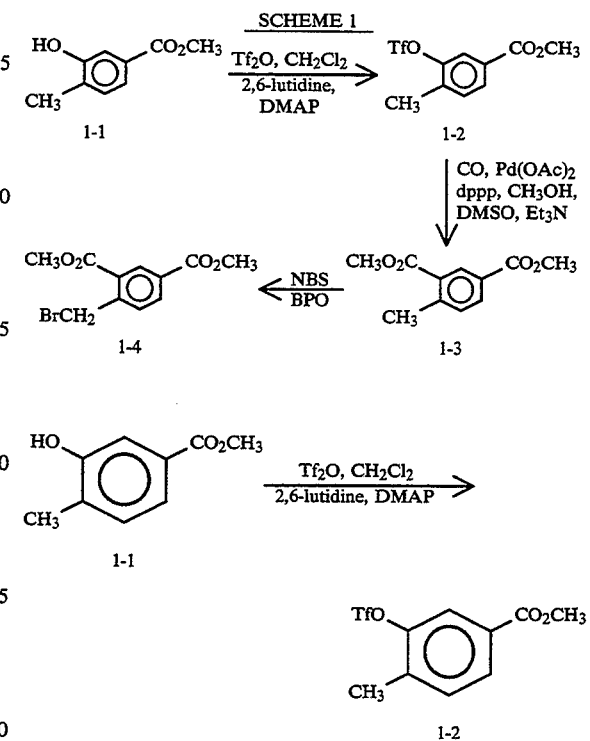

Methyl 4-methyl-3-trifluoromethanesulfonyloxybenzoate (1-2)

A solution of methyl 4-methyl-3-hydroxybenzoate (1-1) (20.0 g, 0.12 moles) [prepared from the corresponding carboxylic acid (Aldrich) by treatment with a methanolic solution of HCl gas] in $CH_2Cl_2$ (900 ml) was cooled to −40° and treated successively with 2,6-lutidine (0.18 moles), DMAP (2.9 g, 0.024 moles) and trifluoromethylsulfonyl anhydride (0.18 moles). The cooling bath was then removed and the resulting mixture was stirred at ambient temperature for 2.0 hours. The solvent was then removed and the residue was purified by flask chromatography on silica eluting with hexane(8)/EtOAc(2) to provide pure 1-2, $R_f$ 0.35.

$^1$H NMR (300 MHz, CDCl$_3$) δ2.18 (3H, s), 3.85 (3H, s), 7.30 (1H, d), 7.84 (1H, s), 7.90 (1H, d).

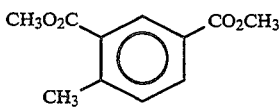

Dimethyl 4-methylbenzene-1,3-dicarboxylate (1-3)

A solution of 1-2 (30.0 g, 0.121 moles) in methanol/300 ml was treated successively with DMSO (180 ml), triethylamine (0.278 moles), palladium acetate (0.807 g, 3.6 mmoles) and dppp (1.48 g, 3.6 mmoles) as the reaction turned to a clear dark brown solution. Carbon monoxide was then bubbled through the reaction mixture for 3 minutes and the resulting mixture was heated at reflux, while continuing to bubble CO. After refluxing for 4 hours the reaction mixture was concentrated and the resulting brown oil was purified by flash chromatography on silica gel eluting with hexane(90)/EtOAc(10) to provide pure 1-3.

$^1$H NMR (300 MHz, CDCl$_3$) δ2.69 (3H, s), 3.95 (3H, s), 3.96 (3H, s), 7.37 (1H, d), 8.09 (1H, dd), 8.60 (1H, d).

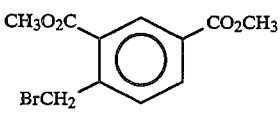

Dimethyl 4-bromomethylbenzene-1,3-dicarboxylic acid (1-4)

A solution of 1-3 (1.35 g, 6.5 mmole) in CHCl$_3$ (20 ml) was treated with dibenzoyl peroxide (0.078 g, 3.5 mmol) and N-bromosuccinimide (NBS) (1.1 g, 6.5 mmole) and the resulting solution was heated at reflux for 2 hours.

The cooled reaction mixture was concentrated, taken up in CCl$_4$, filtered and the filtrate was concentrated to give 1-4 as a tan solid. $R_f$ 0.5 [silica gel, hexane(70)/EtOAc(30)].

Preparation of Boc-4-Piperidine-2-ethanol (1-5)

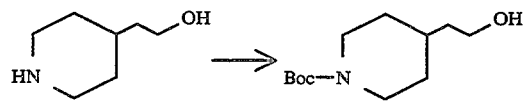

4-Piperidine-2-ethanol (Aldrich) (130 g, 1.0 mole) was dissolved in 700 mL dioxane, cooled to 0° C. and treated with 3N NaOH (336 mL, 1.0 mole), and di-t-butyldicarbonate (221.8 g, 1.0 mole). The ice bath was removed and the reaction stirred overnight. The reaction was concentrated, diluted with water and extracted with ether. The ether layers were combined, washed with brine, dried over MgSO$_4$, filtered and evaporated to give 1-5 $R_f$=0.37 in 1:1 EtOAc/Hexanes, ninhydrin stain.

$^1$H NMR (300 MHz, CDCl$_3$) δ4.07 (bs, 2H), 3.7 (bs, 2H), 2.7 (t, J=12.5 Hz, 2H), 1.8–1.6 (m, 6H), 1.51 (s, 9H), 1.1 (ddd, J=4.3, 12.5, 12 Hz, 2H).

Boc-4-piperidine-2-ethyl iodide (1-6)

Boc-4-piperidine-2-ethanol (1-5) (10.42 g, 0.048 mole was dissolved in 400 ml benzene and imidazole (4.66 g, 0.068 moles) and triphenylphosphine (15.24 g, 0.05 moles) were added at room temperature. After 6 hours the reaction mixture was filtered and the filtrate was evaporated to give a dark residue. This was purified by flash chromatography on silica gel eluting with 10% EtOAc-hexanes to give 1-6 as a yellow oil.

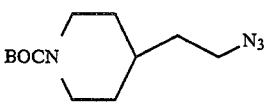

Boc-4-piperidine-2-ethylazide (1-7)

To 1-6 (27.9 g, 0.082 moles) dissolved in DMSO (400 ml) was added sodium azide (5.01 g, 0.086 moles) at room temperature and the resulting solution was heated at 65° for 2 hours. The cooled reaction mixture was diluted with 250 ml EtOAc, extracted with 2×100 ml portions of water 2×50 ml portions of brine and then dried (MgSO$_4$). Solvent removal provided 1-7 as a pale yellow oil, $R_f$ 0.5 (silica gel, 70% acetone/hexane).

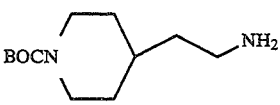

Boc-4-piperidine-2-ethylamine(1-8)

To a solution of 1-5 (19.3 g, 0.076 moles) in THF (400 ml)/H$_2$O (195 ml) was added triphenylphosphine (80.0 g, 0.305 moles) in one portion at room temperature. This was stirred at room temperature 3 hours and the organic solvents were then removed in vacuo. The residue was acidified to pH 2 with 10% KHSO$_4$ solution and this was extracted 4×100 ml portions of EtOAc. The organic extract was extracted with 2×100 ml portions of 10% KHSO$_4$ and the aqueous phases were combined and the pH was adjusted to 10 with 2N NaOH. This solution was extracted with 4×200 ml portions of CH$_2$Cl$_2$. These were combined, dried (MgSO$_4$) and the solvent was removed to give 1-8 as an oil. $R_f$ 0.3 (silica gel, eluting with 10% CH$_3$OH in CHCl$_3$/NH$_3$).

$^1$H NMR (300 MHz, CDCl$_3$) δ4.05 (broad, 2H), 2.72 (t, J=7.2 Hz, 2H), 2.62 (m, 2H), 1.64 (d, J=12.2 Hz, 2H), 1.43 (s, 9H), 1.42–1.32 (m, 5H), 1.09 (m, 2H).

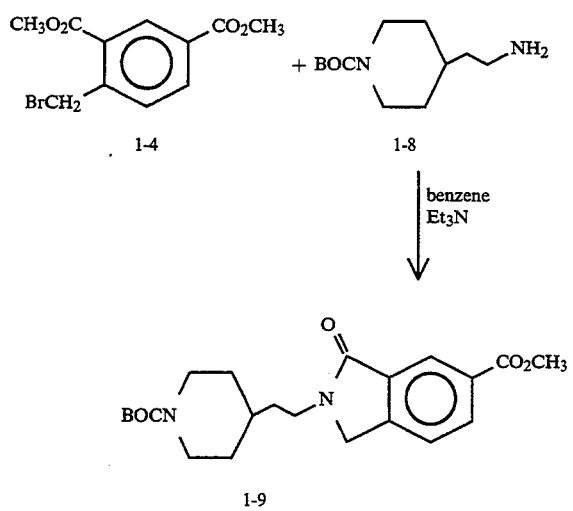

Methyl-1H-Isoindole-5-carboxylate, 2,3-dihydro-N-[2(4-N-t-butyloxycarbonylpiperidinyl)ethyl]-3-oxo (1-9)

A solution of 1-4 (1.0 g, 3.5 mmoles) in benzene (5 ml) was treated with 1-8 (0.80 g, 3.5 mmol) and triethylamine (0.49 ml, 3.5 mmol) and the reaction mixture was heated at reflux for 3 hours. The solvent was removed and the residue was taken up in EtOAc, washed in 10% KHSO₄ solution, H₂O, brine and dried. Solvent removal gave a residue that was purified by flash chromatography on silica gel eluting with hexane(1)/EtOAc(1) to give pure 1-9. R$_f$0.2 (silica gel, hexane(1)/EtOAc(1)).

¹H NMR (300 MHz, CDCl₃) δ1.08 (2H, m), 1.43 (9H, s) 1.61 (4H, m), 1.73 (2H, bd), 2.62 (2H, bt), 3.64 (2H, t), 3.93 (3H, s), 4.07 (2H, m), 4.40 (2H, s), 7.50 (1H, d), 8.21 (1H, dd), 8.47 (1 H, d).

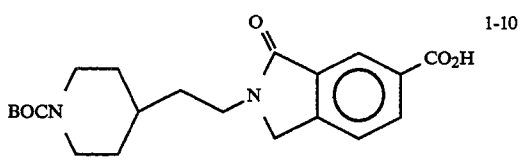

1-H-Isoindole-5-carboxylic acid, 2,3-dihydro-N-[2-(4-N-t-butyloxycarbonylpiperidinyl)ethyl]-3-oxo (1-10)

A solution of 1-9 (0.43 g, 1.12 mmole) in THF (1)/MeOH(1)/H₂O(1) (9 ml) was treated at room temperature with LiOH·H₂O (0.235 g, 5.6 mmol) and the resulting solution was stirred for 4 hours. The reaction mixture was then diluted with EtOAc (75 ml)/10% KHSO₄ solution (30 ml) and the organic phase was separated and dried (Na₂SO₄). Solvent removal gave the desired acid 1-10. R$_f$0.5 (silica gel, CH₂Cl₂(9)/MeOH (0.5)/HOAc(0.5)).

¹H NMR (300 MHz, CDCl₃) δ1.12 (2H, m), 1.42 (9H, s), 1.60 (3H, m), 1.71 (2H, bd), 2.63 (2H, bt), 3.68 (2H, t), 4.08 (2H, m), 4.40 (2H, s), 7.03 (1H, d), 8.28 (1H, dd), 8.60 (1H, s).

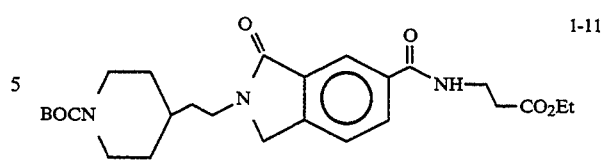

1-H-Isoindole-5-carboxamide, 2,3-dihydro-N-[2-(carbo-ethoxy)ethyl]-2-[2-(4-N-t-butyloxycarbonylpiperidin-yl)ethyl]-3-oxo (1-11)

A solution of 1-10 (0.35 g, 0.94 mmole), triethylamine (0.40 ml, 2.82 mmol), and g-alanine ethyl ester (0.22 g, 1.41 mmol) (Aldrich) in CH₃CN (5 ml) was treated at room temperature with BOP (1.2 mmoles) reagent and the resulting solution was stirred for 16 hours.

The solvent was removed and the residue was taken up in EtOAc, washed with H₂O, 10% KHSO₄ solution, brine and dried (Na₂SO₄). Solvent removal gave a residue that was purified by flash chromatography on silica gel eluting with hexane(20)/EtOAc(80) to give pure 1-11 as a clear oil.

¹H NMR (300 MHz, CDCl₃) δ1.10–1.30 (3H, m), 1.44 (9H, s), 1.60 (3H, m), 1.75 (2H, bd), 2.63 (4H, m), 3.70 (4H, m), 4.05–4.20 (4H, m), 4.38 (2H, s), 7.50 (1H, d), 8.08 (2H, m).

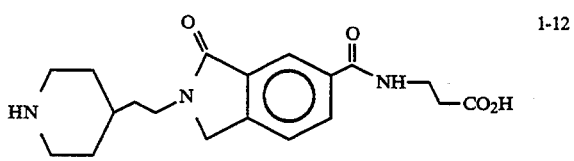

1-H-Isoindole-5-carboxamide, 2,3-dihydro-N-(2-carboxyethyl)-2-[2-(4-piperidinyl)ethyl]-3-oxo (1-12)

A solution of 1-11 (0.32 g, 0.68 mmol) in THF(1)/MeOH(1)/H₂O (1) (9 ml) was treated with LiOH·H₂O (0.14 g, 3.4 mmoles) at room temperature for 1.0 hr. The solvent was then removed and the residue was taken up in EtOAc and washed with 10% KHSO₄ solution, brine and dried (Na₂SO₄). Solvent removal gave the desired acid. R$_f$0.3 (silica gel, CHCl₃ (9)/MeOH (0.5)/HOAc (0.5)).

This acid (0.30 g, 0.68 mmole) was dissolved in CH₂Cl₂ and anisole (150 μl was added. This was cooled to −15° C. and trifluoroacetic acid (3 ml) was added and the resulting mix stirred for 0.5 hours. The solvent was removed and the residue purified by flash chromatography on silica gel eluting with EtOH (9)/NH₄OH (1.2)/H₂O (1.2) to provide pure 1-12.

¹H NMR (300 MH₃, D₂O) δ1.30 (7H, m), 1.50–1.70 (3H, m), 1.83 (2H, bd), 2.38 (2H, t), 2.80 (2H, dt), 3.27 (2H, bd), 3.50 (4H, m), 4.42 (2H, s), 7.51 (1H, d), 7.83 (2H, m).

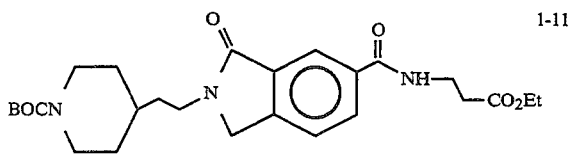

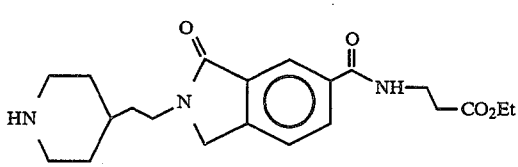

1-H-Isoindole-5-carboxamide,
2,3-dihydro-N-[2-(carboethoxy)ethyl]-2-[2-(4-piperidinyl)ethyl]-3-oxo (1-13)

A solution of 1-11 (0.72 g, 1.57 mmoles) in EtOAc (20 ml) was cooled to −78° C. and HCl gas was bubbled through. This solution for 1-2 minutes and the reaction mixture was then stirred at 0° C. After a few minutes a white solid had precipitated and this mixture was stirred for 0.5 hours. The solvent was then removed and the residue was triturated with Et$_2$O to give pure 1-13.

$^1$H NMR (300 MHz, CD$_3$OD) δ1.23 (3H, t), 1.45 (2H, m), 1.66 (2H, m), 1.72 (2H, m), 2.07 (2H, m), 2.65 (2H, t), 2.94 (2H, m), 3.47 (2H, bd), 3.68 (4H, m), 4.12 (2H, q), 4.57 (2H, s), 7.67 (1H, d), 8.03 (1H, dd), 8.14 (1H, d).

minutes. The solvent was then removed and the residue was slurried in DMF (20 ml) and this was treated at room temperature with chloromethyl pivalate (1.8 mmoles). The resulting mixture was stirred at room temperature for 24 hours.

The reaction mixture was then diluted with EtOAc and washed with H$_2$O, 10% KHSO$_4$, saturated with NaHCO$_3$ solvent and brine. The organic phase was dried (MgSO$_4$), and the solvent removed to provide 1-15 as a white solid.

$^1$H NMR (300 MHz, CDCl$_3$) δ1.11–1.25 (13H, m), 1.46 (9H, s), 1.63 (2H, q), 1.77 (2H, bd), 2.62–2.76 (4H, m), 3.72 (9H, m), 4.09 (2H, bd), 4.42 (2H, s), 5.80 (2H, s), 6.89 (1H, bt), 7.53 (1H, d), 8.09 (1H, d), 8.14(1H, s).

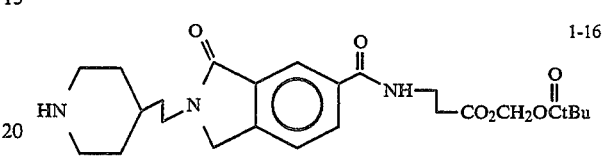

1-H-Isoindole-5-carboxamide,
2,3-dihydro-N-[2-(t-butylcarbonyloxy-methylcarboxy)ethyl]-2-[2-(4-piper-idinyl)ethyl]-3-oxo (1-16)

A solution of 1-15 (15 mg) in EtOAc (5 ml) was cooled to −78° C. and treated with HCl gas for 10 minutes and the resulting solution was stirred at −10° C. for 1.0 hour. The solvent was then removed to provide pure 1-16 as a white solid.

$^1$H NMR (300 MHz, CD$_3$OD) δ1.06 (9H, s), 1.92 (1H, m), 1.70 (2H, m), 2.08 (2H, bd), 3.73 (2H, t), 2.95 (2H,

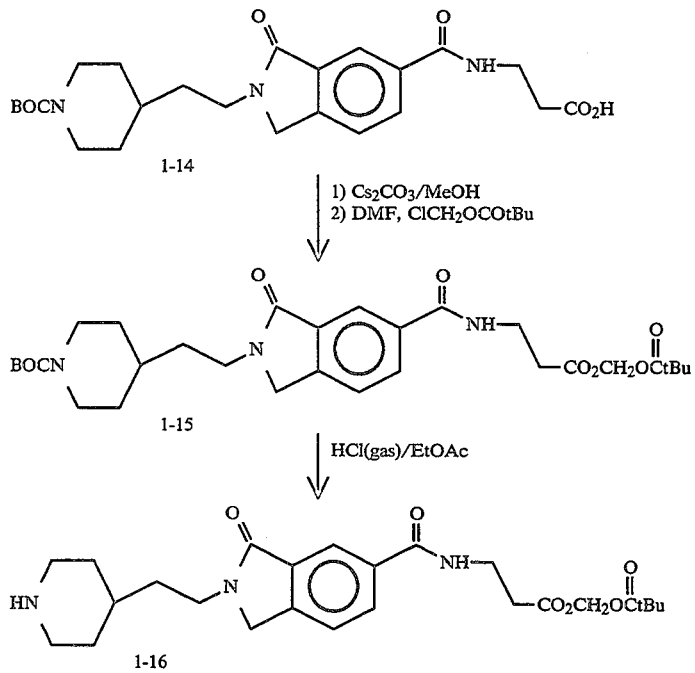

1H-Isoindole-5-carboxamide,
2,3-dihydro-N-[2-(t-butylcarbonyloxy-methylcarboxy)ethyl]-2-[2-(4-N-t-butyloxycarbonylpiperidinyl)ethyl]-3-oxo (1-15)

A slurry of 1-16 (0.80 g, 1.8 mmoles) in MeOH (20 ml) was treated with Cs$_2$CO$_3$ (0.24 g, 0.90 mmoles) at room temperature and the resulting mixture was stirred for 45 dt), 3.38 (2H, bd), 3.70 (6H, m), 4.58 (2H, s), 5.86 (2H, s), 7.67 (1H, d), 8.06 (1H, d), 8.17 (1H, s).

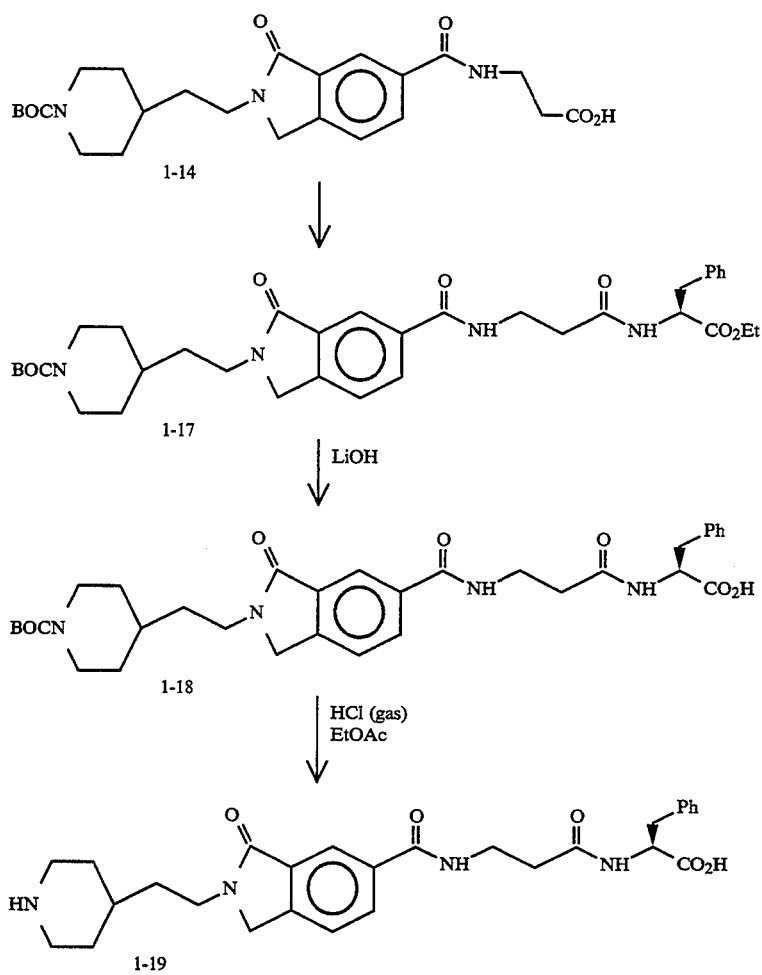

1-H-Isoindole-5-carboxamide, (1H, q), 7.12 2H, m), 7.25 (5H, m), 7.54 (1H, d), 8.08 d), 8.19 S).

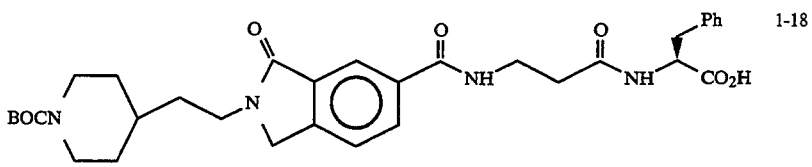

2,3dihydro-N-[L-Phe(OEt),2-carboxamido)ethyl]-2-[2-(4-N-t-butyl-oxycarbonylpiperidinyl)ethyl]-3-oxo(1-17)

1-14 (0.35 g, 0.76 mmoles) was treated with L-phenylalanine ethyl ester (2.0 mmoles), N-methylmorpholine (2.0 mmoles) and BOP (0.886 g, 2.0 mmoles), in $CH_3CN$ (5 ml) at room temp for 24 hrs. as described for 6-3. Flash chromatography on silica gel eluting with EtOAc (9)/MeOH (1) gave pure 1-17 as a white solid. $R_f$ 0.3 (silica gel, $CHCl_3(2)$/acetone (1).

$^1$H NMR (300 MHz, $CDCl_3$) δ1.28 (3H, t), 1.47 (9H,S), 1.79 (2H, bd), 2.54 (2H, t), 2.72 (2H, m), 3.15 (2H, m) 3.75 (5H, m), 4.20 (4H, m), 4.43 (2H, S), 2.90

1-H-Isoindole-5-carboxamide, 2,3-dihydro-N[L-Phe-2-(carboxamido)ethyl]-2-[2-(4-N-t-butyloxycarbonyl-piperidinyl)ethyl]-3-oxo(1-18)

1-17 (0.46 g, 0.72 mmoles) was treated with LiOH·$H_2O$ (0.152 g, 3.6 mmoles) as described for 1-12 to give 1-18 as a white solid.

$^1$H NMR (300 MHz, $CD_3OD$) δ1.13 (2H, m), 1.43 (9H, s), 1.66 (2H, q), 1.80 (2H, bd), 2.50 (2H, t), 2.70 (2N, M), 2.93 (1H, m), 3.20 (1H, dd), 3.58 (2H, q), 3.70 (2H, t), 4.04 (2H, m), 4.56 (2H, S), 4.68 (1H, m), 7.20 (5H, m), 7.56 (1H, d), 8.02 (1H, d), 8.15 (1H, s).

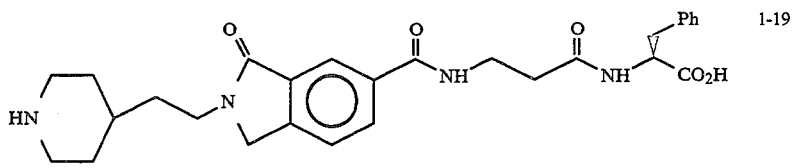

1-H-Isoindole-5-carboxamide, 2,3-dihydro-N[L-Phe-2-(carboxamido)ethyl]-2-[2-(4-piperidinyl)ethyl]-3-oxo (1-19)

1-18 (0.35 g, 0.37 mmoles) was treated with HCl gas as described for 1-13 to give pure 1-19 as a white solid.

$^1$H NMR (300 MHz, CDCl$_3$) δ1.16 (2H, m), 1.45 (9H,s), 1.42 (2H, q), 1.65 (2H, bd), 2.03 (2H, m), 2.66 (5H, m), 3.51 (1H, m), 3.67 (2H, m), 3.80 (2H, m), 4.09 (2H, m), 4.20 (2H, q), 4.40 (2H, s), 4.50 (1H, m), 7.41 (1H, m), 7.50 (1H, d), 8.03 (1H, d), 8.19 (1H, s).

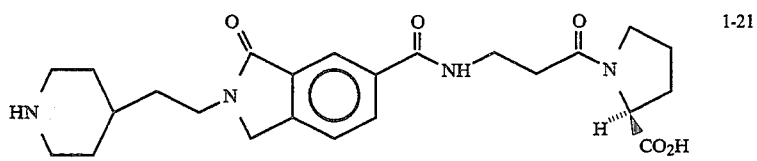

$^1$H NMR (300 MHz, D$_2$O) δ1.35 (2H, m), 1.62 (2H, m), 1.93 (2H, m), 2.43 (2H, m), 2.79 (3H,m), 3.07 (1H, m), 3.28 (2H, m), 3.45(2H, m), 4.50 (2H,S), 6.80 (1H, m), 6.92 (2H, m), 7.00 (2H, m), 7.55 (1H, d), 7.77 (2H, bs).

1-H-Isoindole-5-carboxamide, 2,3-dihydro-N-[L-Pro-2-(carboxamido)ethyl]-2-[2-(4-piperidinyl)ethyl]-3-oxo(1-21)

1-20 (0.2 g, 0.34 mmoles) was treated with LiOH·H$_2$O

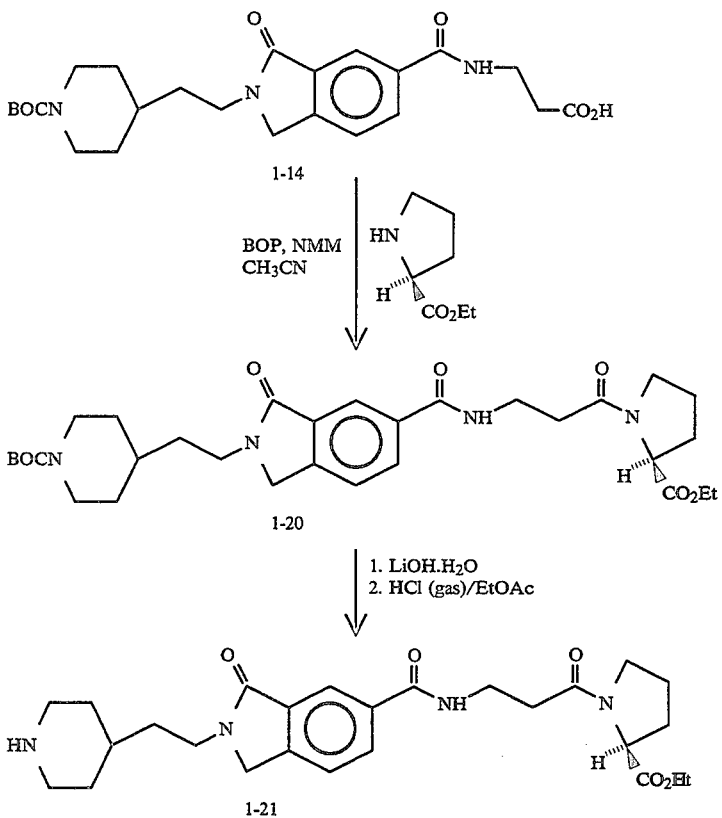

1-H-Isoindole-5-carboxamide, 2,3-dihydro-N-[L-Pro(OEt)-2-(carboxamido)ethyl]-2-[2-(4-N-t-butyloxycarbonylpiperidinyl)ethyl]-3-oxo (1-20)

1-14 (0.35 g, 0.76 mmoles) was treated with L-Proline ethyl ester (0.288 g, 2.0 mmoles), N-methylmorpholine (2.0 mmoles) and BOP (0.886 g, 2.0 mmoles) in CH$_3$CN (5 ml) as described for 1-17 to give an oily residue. This was purified by flash chromatography on silica gel eluting with acetone (1)/CHCl$_3$(1) to give pure 1-20.

(0.07 1 g, 1.7 mmoles) as described for 1-12 to give the desired acid.

$^1$H NMR (300 MHz, CD$_3$OD) δ1.15 (2H, m), 1.44 (9H, s), 1.67 (2H, q), 2.80 (2H, bd), 2.25 (1H, m) 2.73 (2H, m), 3.68 (4H, m), 4.06 (2H, m), 4.55 (2H, s), 7.66 (1H, d), 8.05 (1H, d), 8.17 (1H, s).

This acid (0.15 g) was dissolved is EtOAc (10 ml) and treated with HCl gas as described for 1-13 to give pure 1-21 as a white solid.

¹H NMR (300 MHz, D₂O) δ1.48 (2H, m), 1.67 (1 H, m), 1.76 (2H, m), 2.06 (4H, m), 2.32 (1H, m), 2.62 (1H, m), 2.84 (2H, t), 2.96 (2H, t), 3.43 (2H, d), 3.70 (6H, m), 4.47 (1H, m), 4.66 (2H, s), 7.72 (1H, d), 8.00 (1H, d), 8.09 (1H, s).

4-(N-t-Butyloxycarbonylpiperidinyl)methylamine (2-3)

A solution of 4-(piperidinyl)methylamine (2-1) (22.8 g, 0.2 mmoles) in toluene (250 ml) was treated with benzaldehyde (21.2 g, 0.2 mmoles) at room temperature and the resulting mixture was heated at reflux for 3 hours with the aid of a Dean-Stark trap for water removal. The cooled reaction mixture containing the desired Schiff's base 2—2 was treated portionwise with di-t-butyl dicarbonate (47.96 g, 0.22 moles) and the resulting solution was stirred at room temperature for 16 hours. The solvent was then removed and the residue was cooled to 0°–5° C. and treated with 1N KHSO₄ (220 ml) with stirring for 3 hours. The resulting reaction mixture was extracted with ether (3×200 ml) and then made basic with 1N KOH solution and extracted with CHCl₃ (4×75 ml). The combined organic extract was washed with brine, dried (Na₂SO₄) filtered through celite, and the solvent removed to provide pure 2-3 as a clear oil.

¹H NMR (300 MHz, CDCl₃) δ1.13 (2H, m), 1.45 (9H, s), 1.60 (1H, m), 1.74 (2H, d), 2.68 (4H, m), 4.15 (2H, bd).

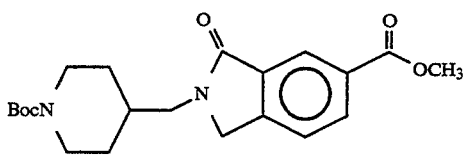

Methyl-1H-Isoindole-4-carboxylate, 2,3-dihydro-N-[(4-N-t-butyloxycarbonylpiperidinyl)-methyl]-3-oxo (2-4)

A solution of 1-4 (3.01 g, 10.5 mmoles) in benzene (20 ml) was treated at room temperature with 2-3 (2.30 g, 10.7 mmoles) and Et₃N (10.8 mmoles) and the resulting solution was heated at reflux for 2 hours. The solvent was removed and the residue was taken up in EtOAc (200 ml) and extracted with 10% KHSO₄ solution (5×50 ml), brine and dried (MgSO₄). Solvent removal gave a residue that was purified by flash chromatography on silica gel eluting with hexane (1)/EtOAc (1) to give pure 2-4. R_f 0.25.

¹H NMR (300 MHz, CDCl₃) δ1.29 (2H, m), 1.45 (9H, s), 1.67 (4H, m), 1.95 (1H, m), 2.70 (2H, t), 3.52 (2H, b), 3.97 (3H, s), 4.13 (2H, b), 4.95 (2H, s), 7.52 (1H, d), 8:23 (1H, d), 8.50 (1H, s).

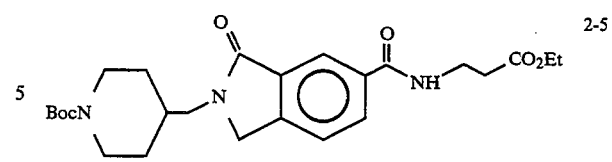

1-H-Isoindole-5-carboxamide, 2,3-dihydro-N-[2-(carboethoxyethyl]-2-[(4-N-t-butyloxycarbonyl-piperidinyl)methyl]-3-oxo (2-5)

A solution of 2-4 (1.92 g, 5.58 mmoles) in 150 ml of THF(1)/MeOH(1)/H₂O(1) was treated with LiOH·H₂O (1.20 g, 28.6 mmoles) at room temperature and the resulting solution was stirred for 1.0 hr. The solvent was then removed and the residue was taken up in H₂O (100 ml) acidified to pH 2 with 10% KHSO₄ solution. The desired acid precipitated from solution and was collected.

¹H NMR (300 MHz, CD₃OD) δ1.13 (2H, m), 1.40 (9H, s), 1.50–1.65 (3H, m), 2.70 (2H, b), 3.45 (2H, d), 3.98 (2H, d), 4.45 (2H, s), 7.60 (1H, d), 8.10 (1H, d), 8.21 (1H, s).

This acid (1.62 g, 4.91 mmoles) was dissolved in CH₃CN (25 ml) and treated at 0° successively with Et₃N (34.4 mmoles), δ-alanine ethyl ester (5.0 mmoles), and BOP (3.27 g, 7.38 mmoles). The reaction mixture was then stirred at room temperature for 16 hrs. The solvent was removed and the residue purified by flash chromatography in silica gel eluting with EtOAc (7)/hexane (1) to provide 2-5 as a white solid.

¹H NMR (300 MHz, CDCl₃) δ1.27 (6H, m), 1.42 (9H, s), 1.67 (5H, m), 1.95 (1H, m), 2.66 (4H, m), 3.50 (2H, b), 3.74 (2H, g), 4.16 (4H, m), 4.45 (2H, s), 7.00 (1H, t), 7.53 (1H, d), 8.11 (2H, m).

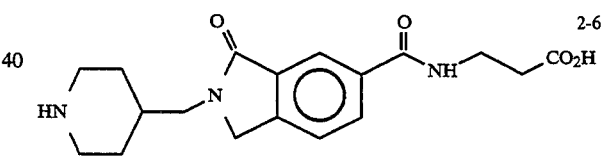

1-H-Isoindole-5-carboxamide, 2,3-dihydro-N-(2-carboxyethyl)-2-[(4-piperidinyl)methyl]-3-oxo (2-6).

A solution of 2-5 (0.86 g, 2.0 mmoles) in 60 ml of THF(1)/MeOH(1)/H2O (1) was treated with LiOH·H₂O (0.45 g, 10.7 mmoles) at room temperature and the resulting solution was stirred at room temperature for 1.0 hr. The solvent was removed and the residue was dissolved in H₂O (25 ml), acidified to pH 2-3 with 10% KHSO₄ solution and extracted with EtOAc (4×25 ml). The combined organic extracts were washed with brine, dried (Na₂SO₄) and the solvent removed to give the desired acid as a white solid.

¹H NMR (300 MHz, CD₃OD) δ1.16 (2H, m), 1.39 (9H, s), 1.45 (1H, m), 1.80 (2H, bd), 1.93 (2H, d), 2.58 (2H, t), 2.70 (2H, b), 3.45 (2H, d), 3.57 (2H, t), 4.00 (2H, m), 7.59 (1H, d), 8.00 (1H, d), 8.09 (1H, s).

This acid (0.80 g, 1.89 mmoles) was treated with HCl gas in EtOAc solution as described for 2-3 to provide pure 2-6 as a white solid.

¹H NMR (300 MHz, CD₃OD) δ1.43 (2H, m), 1.85 (2H, m), 2.10 (1H, m), 2.56 (2H, t), 2.90 (2H, t), 3.34 (2H, bd), 3.54 (4H, m), 4.52 (2H, s), 7.61 (1H, d), 8.00 (1H, d), 8.10 (1H, s).

2-5 can also be converted to 2-7 as shown below:

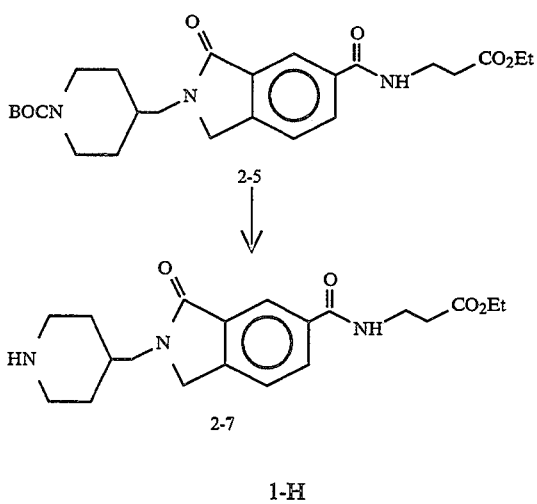

1-H-Isoindole-5-carboxamide,2,3-dihydro-N-[(2-carboethoxy)ethyl]-2-]2-(4-piperidinyl)ethyl]-3-oxo(2-7).

Treatment of 2-5 (0.90 g, 2.09 mmoles) in EtOAc with HCl gas as described for 1-12 gave 2-7 as an white, solid.

$^1$H NMR (300 MHz, CD$_3$OD) δ1.09 (3H, t), 1.45 (2H, m), 1.86 (2H, bd), 2.13 (2H, m), 2.60 (2H, t), 2.90 (2H, t), 3.32 (2H, bd), 3.56 (4H, m), 4.08 (2H, q), 4.56 (2H, s), 7.62 (1H, d), 8.00 (1H, d), 8.09 (1H, s).

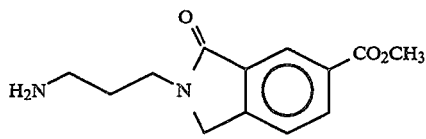

Methyl-1H-Isoindole-5-carboxylate, 2,3-dihydro-N-[3-aminopropyl]-3-oxo (3-1)

A solution of 1-4 (2.58 g, 8.99 mmoles in benzene (10 ml) was treated with Et$_3$N (12.9 mmoles) and 1,3-diaminopropane (13.0 mmoles) at room temperature and the resulting mixture was heated at reflux for 2 hrs. The reaction mixture was cooled and the solvent removed to give 3-1.

$^1$H NMR (300 MHz, CD$_3$OD) δ1.53 (9H, s), 1.79 (2H, m), 3.02 (2H, m), 3.58 (2H, m), 3.84 (3H, s), 4.48 (2H, s), 7.58 (1H, d), 8.10 (1H, d), 8.20 (1H, s).

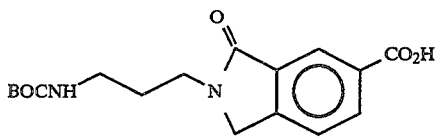

1-H-Isoindole-5-carboxylic acid, 2,3-dihydro-N-[3-(N-t-butyloxy-carbonylamino)propyl]-3-oxo (3-2)

3-1 (2.22 g, 8.99 mmoles) was suspended in 100 ml of THF(1)/H$_2$O(1) and treated with Et$_3$N (9.3 mmoles) and di-t-butyl dicarbonate (4.0 g, 18.3 mmoles) and the resulting mixture was stirred vigorously for 5 hrs. The solvent was removed and the residue was purified by flash chromatography to give the desired protected ester.

$^1$H NMR (300 MHz, CD$_3$OD) δ1.53 (9H, s), 1.80 (2H, m), 3.03 (2H, m), 3.58 (2H, m), 3.86 (3H, s), 4.48 (2H, s), 7.55 (1H, d), 8.10 (1H, d), 8.20 (1H, s).

This ester (0.67 g, 1.93 mmoles) was treated with LiOH·H$_2$O (0.41 g, 9.76 mmoles) in 60 ml of THF(1)/MeOH(1)/H$_2$O (1) at room temperature for 1 hr. Solvent removal gave a residue that was dissolved in 25 ml H$_2$O, acidified to pH 2-3 with 10% KHSO$_4$ solution and extracted with EtOAc (4×25 ml). The organic extract was washed with brine, dried (MgSO$_4$) and the solvent removed to give 3-2 as a white solid.

$^1$H NMR (300 MHz, CD$_3$OD) δ1.35 (9H, s), 1.80 (2H, m), 3.04 (2H, t), 3.62 (2H, t), 4.55 (2H, s), 7.62 (1H, d), 8.20 (1H, d), 8.32 (1H, s).

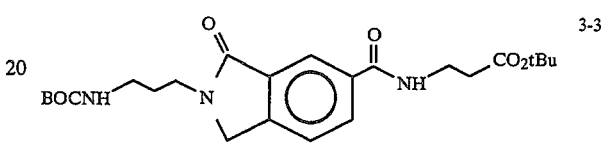

1-H-Isoindole-5-carboxamide, 2,3-dihydro-N-[2-(t-butyloxycarbonyl)ethyl]-2-[3-(N-t-butyloxycarbonyl-amino)propyl]3-oxo (3—3)

A solution of 3-2 (0.65 g, 1.94 mmoles) in 10 ml CH$_3$CN was cooled to 0°-10° and treated with Et$_3$N (13.6 mmoles) and BOP (1.30 g, 2.93 mmoles) and the resulting solution was stirred at room temperature for 16 hrs. The solvent was then removed and the residue was taken up in EtOAc (100 ml) extracted with H$_2$O (4×25 ml), 10% KHSO$_4$ solution and dried (MgSO$_4$). Solvent removal give a residue that was purified by flash chromatography on silica gel eluting with CHCl$_3$(95)/MeOH(5) to give pure 3-3 as a white solid. R$_f$0.3 (silica gel, CHCl$_3$(95)/MeOH(5)).

$^1$H NMR (300 MHz, CDCl$_3$), δ1.46 (9H, s), 1.53 (9H, s), 1.90 (2H, m), 2.62 (2H, t), 3.60 (2H, m), 3.76 (4H, m), 4.50 (2H, s), 7.00 (1H, 6t), 7.62 (1 h, d). 8.17 (1H, d), 8.20 (1H, s).

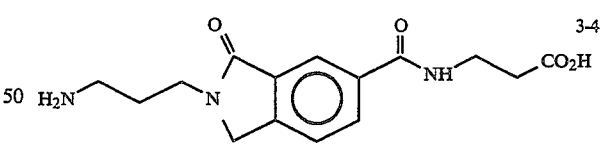

1-H-Isoindole-5-carboxamide, 2,3-dihydro-N-(2-carboxy-ethyl)-2-[3-aminopropyl]-3-oxo (3-4)

3—3 (0.77g, 1.67 mmoles) was suspended in EtOAc (25 ml) and after cooling to −70°, HCl gas was bubbled into the mixture for 5 minutes at which time the reaction mixture was homogeneous. The reaction mixture was then stirred at 0°-5° for 30 minutes. The solvent was removed and the residue was dried at high vacuum to provide pure 3-4 as a white solid.

$^1$H NMR (300 MHz, CD$_3$OD) δ2.00 (2H, m), 2.60 (2H, t) 2.92 (2H, t), 3.59 (2H, m), 3.70 (2H, t), 4.28 (2H, s), 7.63 (1H, d), 8.02 (1H, d), 8.12 (1H, s).

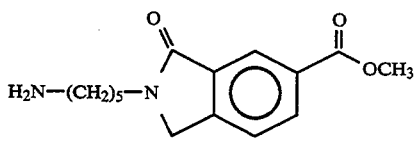

Methyl-1H-Isoindole-5-carboxylate, 2,3-dihydro-N-[5-aminopentyl]-3-oxo (4-1)

A solution of 1-4 (2.56 g, 8.92 mmoles) in benzene (15 ml) was treated with Et₃N (11.5 mmoles) and 1,5-diaminopentane (11.9 mmoles) and the resulting reaction mixture was heated at reflux for 3 hrs. The solvent was then removed and the residue was purified by flash chromatography on silica gel eluting with 25% MeOH in CHCl₃(MHz) to provide pure 4-1.

¹H NMR (300 MHz, CDCl₃) δ1.77 (6H, m), 2.45 (2H, bs), 2.71 (2H, t), 3.63 (2H, t), 4.44 (2H, s), 7.52 (1H, d), 8.22 (1H, d), 8.49 (1H, s).

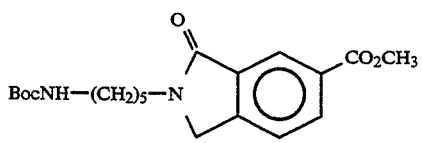

Methyl-1H-Isoindole-5-carboxylate, 2,3-dihydro-N-[5-(N-t-butyloxy-carbonylamino)pentyl]-3-oxo (4-2)

A solution of 4-1 (0.64 g, 2.32 mmoles) in CH₂Cl₂ (10 ml) was treated at room temperature with Et₃N (2.29 mmoles) and Boc₂O (0.74 g, 3.39 mmoles) for 48 hrs. The solvent was then removed and the residue was purified by flash chromatography on silica gel eluting with hexane(7)/acetone(3) to give pure 4-2.

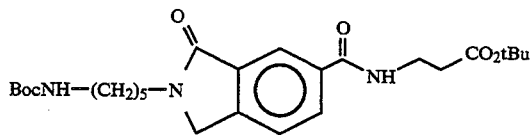

1-H-Isoindole-5-carboxamide, 2,3-dihydro-N-[2-(2-t-butyloxy-carbon)ethyl]-2-[5-N-t-butyloxycarbonyl-amino)pentyl]-3-oxo (4-3)

A solution of 4-2 (0.71 g, 1.89 mmoles) in THF(1)/MeOH(1)/H₂O(1) (60 ml) was treated with LiOH·H₂O (0.42 g, 10.0 mmoles) at room temperature for 0.5 hr. The solvent was then removed and the residue was dissolved in H₂O (50 ml), acidified to pH 2-3 with 10% KHSO₄ solution and extracted with EtOAc. The organic phase was washed with brine, dried (MgSO₄) and the solvent removed to give the desired acid.

¹H NMR (300 MHz, CD₃OD) δ1.30 (9H, s), 1.45 (3H, m), 1.63 (3H, m), 2.92 (2H, t), 3.55 (2H, t), 4.47 (2H, s), 7.58 (1H, d), 8.16 (1H, d), 8.03 (1H, s).

This acid (0.75 g, 2.07 moles) was dissolved in CH₃CN (15 ml) and was treated at room temperature with β-alanine t-butyl ester (0.39 g, 2.54 mmoles), BOP (1.4 g, 3.16 mmoles), Et₃N (6.1 mmoles) and the resulting solution was stirred at room temperature for 20 hrs. The solvent was then removed and the residue was dissolved in EtOAc and extracted with H₂O, 10% KHSO₄ solution and brine. The organic phase was dried (MgSO₄) and was solvent was removed to give a residue that was purified by flash chromatography on silica gel eluting with EtOAc(7)/hexane(3) to give pure 4-3.

¹H NMR (300 MHz, CD₃OD) δ1.39 (9H, s), 1.45 (2H, m), 1.65 (2H, m), 2.50 (2H, t), 2.96 (2H, q), 3.53 (4H, q), 4.47 (2H, s), 7.58 (1H, d), 7.96 (1H, d), 8.08 (1H, s).

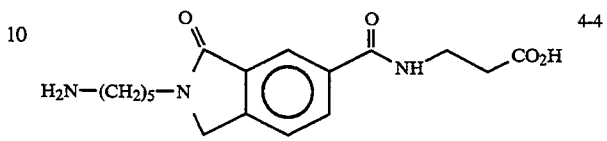

1-H-Isoindole-5-carboxamide, 2,3-dihydro-N-(2-carboxy-ethyl)-2-[5-aminopentyl]-3-oxo (4-4)

A solution of 4-3 (0.71 g, 1.45 mmoles) in EtOAc (20 ml) was cooled to −78° and treated with HCl gas for 10 minutes. The resulting solution was stirred in at 0° for 0.5 hr. The solvent was removed to provide 4-4 as white solid.

¹H NMR (300 MHz, D₂O) δ1.29 (2H, m), 1.63 (4H,m), 2.62 (2H,t), 2.87 (2H, t), 3.52 (4H, m), 4.40 (2H, s), 7.51 (1H, d), 7.80 (2H, m).

N-t-Butyloxycarbonyl-N-methyl-1,3-diaminopropane (5-3).

A solution of N-methyl-1,3-diaminopropane (2.05 g, 23.2 mmoles) in toluene (30 ml) was treated with benzaldehyde (2.41 g, 22.7 mmoles) and the resulting mixture was heated at reflux with use of a Dean-Stark trap. After 2 hrs. the reaction mixture was cooled and treated with Boc₂O (5.57 g, 25.5 mmoles) portionwise and the resulting solution was stirred for 48 hrs.

The solvent was then removed and the residue was cooled to 0°–5° and acidified to pH 2-3 with 10% KHSO₄ solution (25 ml) and the resulting slurry was stirred for 3 hrs. This mixture was then extracted with EtOAc and the aqueous phase was adjusted to pH 9 with 1N NaOH and extracted with CHCl₃ (5×25 ml). The dried organic phase was concentrated to give 5-3 as an oil.

¹H NMR (300 MHz, CDCl₃) δ1.47 (9H, s), 1.72 (2H, bt), 2.16 (2H, bs), 2.75 (2H, t), 2.87 (3H, s), 3.34 (2H, bs).

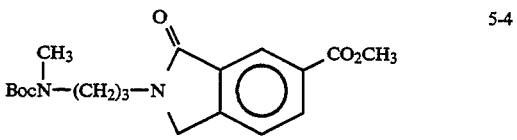

Methyl-1H-Isoindole-5-carboxylate, 2,3-dihydro-N-[2-(3-N-t-butyloxy-carbonyl-N-methylamino)propyl]-3-oxo (5-4)

A solution of 1-4 (2.0 g, 6.97 mmoles) in benzene (10 ml) was treated with 5-3 (1.19 g, 6.32 mmoles) and Et₃N (7.17 mmoles) and the resulting solution was heated at reflux for 24 hrs. The cooled reaction mixture was then dissolved in EtOAc (150 ml), washed with 10% KHSO₄ solution (4×50 ml), brine (50 ml) and dried (MgSO₄). The solvent was removed to give an oil that was purified by flash a chromatography on silica gel eluting with EtOAc(7)/hexane(1 ) to give pure 5-4 as a white solid.

¹H NMR (300 MHz, CDCl₃) δ1.45 (9H, s), 1.92 (2H, m), 2.90 (3H, s), 3.30 (2H, t), 3.68 (2H, t), 3.97 (3H, s), 4.50 (2H, s), 7.55 (1H, d), 8.26 (1H, d), 8.52 (1H, s).

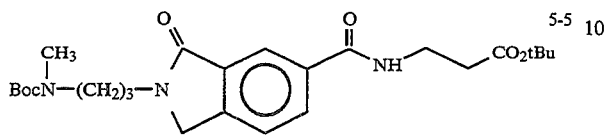

1-H-Isoindole-5-carboxamide, 2,3-dihydro-N-[2-(t-butyloxycarbonyl)ethyl]-2-[3-(N-t-butyloxycarbonyl-N-methylamino)propyl]-3-oxo (5-5)

A solution of 5-4 (1.28 g, 3.53 mmoles) in THF(1)/MeOH(1)/H₂O(1) (105 ml) was treated with LiOH·H₂O (0.76 g, 18.1 mmoles) and the resulting solution was stirred at room temperature for 30 minutes. The solvent was then removed and the residue was taken up in H₂O (30 ml), acidified to pH 2-3 with 10% KHSO₄ solution, and extracted with EtOAc. The combined organic extracts were washed with brine, dried (MgSO₄) and the solvent removed to provide the desired acid.

¹H NMR (300 MHz, CD₃OD) δ1.34 (9H,s), 1.86 (2H, m), 2.78 (3H, s), 3.22 (2H, m), 3.55 (2H, t), 4.50 (2H, s), 7.60 (1H, d), 8.17 (1H, d), 8.30 (1H, s).

This acid (1.28 g, 3.59 mmoles) was dissolved in CH₃CN (20 ml) and treated successively with β-alanine t-butyl ester hydrochloride (0.65 g, 3.59 mmoles), Et₃N (2.51 mmoles), and BOP (2.39 g, 5.40 mmoles) and the resulting cloudy suspension was stirred at room temperature for 20 hrs. The reaction mixture was then concentrated and the residue was taken up in EtOAc (100 ml), extracted with H₂O (2×25 ml), 10% KHSO₄ solution (4×25 ml), brine and dried (MgSO₄). Solvent removal gave a residue that was purified by flash chromatography on silica gel eluting with acetone(3)/hexane(7) to give pure 5-5 as a white solid.

¹H NMR (300 MHz, CDCl₁₃) δ1.42 (9H,s), 1.44 (9H, s), 1.93 (2H, m), 2.37 (2H, t), 2.88 (3H, s), 3.30 (2H, t), 3.68 (4H, m), 4.47 (2H, s), 6.98 (1H, bt), 7.55 (1H, d), 8.09 (1H, d), 8.12 (1H, s).

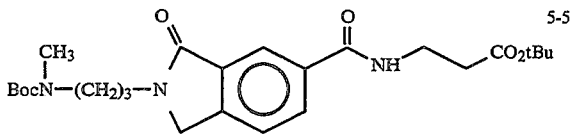

1-H-Isoindole-5-carboxamide, 2,3-dihydro-N-(2-carboxyethyl)-2-[3-(N-methylamino)-propyl]-3-oxo(5-6)

A solution of 5-5 (1.42 g, 2.09 mmoles) in EtOAc (40 ml) was cooled to −78° and treated with HCl gas for 3-5 minutes. The resulting solution was stirred at 0° for 0.5 hr. The solvent was then removed to provide 5-6 as a white solid. ¹H NMR (300 MHz, D₂O) δ2.00 (2H, m), 2.62 (5H, m), 3.00 (2H, t), 3.60 (4H, m), 4.29 (2H, s), 7.75 (1H, d), 7.83 (1H, d), 7.88 (1H, s).

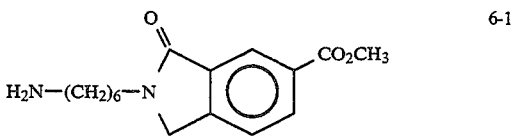

Methyl-1H-Isoindole-5-carboxylate, 2,3-dihydro-N-[6-aminohexyl]-3-oxo (6-1)

Treatment of 1-4 with 1,6-diaminohexane as described for 1-9 provided 6-1 as a white solid. R_f 0.5 (silica gel, hexane (9)/EtOAc (1).

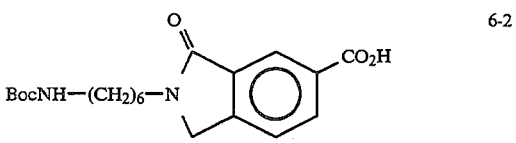

1-H-Isoindole-5-carboxylic acid, 2,3-dihydro-N-[6-N(t-butyloxy-carbonylamino)hexyl]-3-oxo (6-2)

Treatment of 6-1 with Boc₂O (1 equiv) and triethylamine (2 equivalents) in H₂O (1)/THF(1) (100 ml) at room temperature for 48 hours followed by solvent removal gave crude BOC-protected derivative. Hydrolysis of this with LiOH·H₂O (4 equiv.) as described for 1-10 gave 6-2. as an oil. ¹H NMR/(300 MHz, CD₃OD) δ1.32 (17H, m), 1.68 (2H, m) 2.95 (2H, t), 4.50 (2H, s), 7.62 (1H, d), 8.19 (1H, d), 8.31 (1H, s).

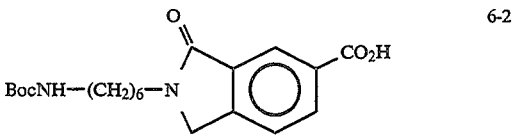

1-H-Isoindole-5-carboxamide, 2,3-dihydro-N-[2-(t-butyloxy-carbonyl)ethyl]-2-[6-N-(t-butyloxycarbonylamino)hexyl]-3-oxo (6-3)

Treatment of 6-2 (1.18 g, 3.12 mmoles) with t-butyl β-alanine (0.54 g, 3.51 mmoles) as described for 1-11 gave crude 6-3. This was purified by flash chromatography on silica gel eluting with pet ether (6)/EtOAc (4) to provide 6-3 as an oil. R_f 0.25 (silica gel, pet ether (7)/acetone (3)).

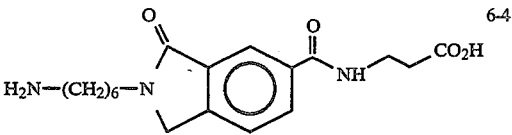

1-H-Isoindole-5-carboxamide,2,3-dihydro-N-(2-carboxy-ethyl)-2-[6-aminohexyl]-3-oxo(6-4)

6-3 (0.44 g) was dissolved in EtOAc (25 ml) cooled to −78° and treated with HCl gas for 5 minutes. The reaction mixture was then stirred at 0° for 30 minutes and the solvent was removed. The residue was purified by flash chromatography on silica gel eluting with EtOH(9)/H₂O(1)/NH₄OH(1) to provide 6-4 as a white solid.

¹H NMR (300 MHz, CD₃OD) δ1.42 (4H, m), 1.68 (4H, m), 2.63 (2H, t), 2.88 (2H, t), 3.60 (4H, m), 4.52 (2H, s), 7.60 (1H, d), 7.97 (1H, d), 8.10(1H, s).

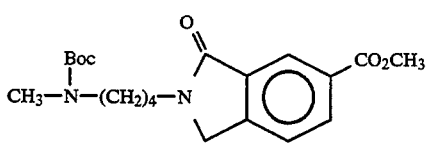

Methyl-1H-Isoindole-5-carboxylate, 2,3-dihydro-N-[4-(N-methyl-N-t-butyloxycarbonylamino)butyl]-3-oxo (7-1)

Treatment of 1-4 with 4-(N-methyl-N-t-butyl-oxycarbonylamino)butylamine (prepared as described for 5-3) as described for 1-9 provided crude 7-1. This was purified by flash chromatography on silica gel eluting with EtOAc(7)/hexane(3) to give pure 7-1. $R_f$ 0.3 (silica gel, EtOAc(7)/hexane(3).

¹H NMR (300 MHz, CDCl₃) δ1.45 (9H, s), 1.60 (4H, m), 7.52 (1H, d), 8.23 (1H, d), 8.23 (1H, d), 8.50 (1H, s).

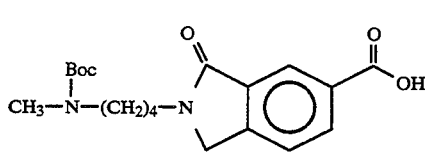

1H-Isoindole-5-carboxylic acid, 2,3-dihydro-N-[4-(N-methyl-N-t-butyloxycarbonylamino)butyl]-3-oxo (7-2)

Treatment of 7-1 (1.16 g, 2.08 mmoles) with LiOH·H₂O (0.65 g, 15.5 mmoles)in THF(1)/CH₃OH(1)/H₂O(1) (75 ml) as described for 1-10 gave 7-2 as a white solid. ¹H NMR (300 MHz, CD₃OD) δ1.67 (10H, m), 1.80 (2H, m), 1.89 (2H, m), 3.05 (3H, s), 3.50 (2H, t), 3.88 (2H, t), 4.78 (2H, s), 7.90 (1H, d), 8.45 (1H, d), 8.60 (1H, s).

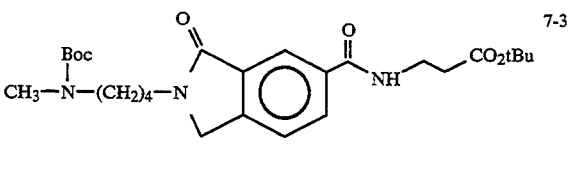

1-H-Isoindole-5-carboxamide, 2,3-dihydro-N-[2-(t-butyloxycarbonyl)ethyl]-2-[4-(N-t-butyloxycarbonyl-N-methylamino)butyl]-3-oxo (7-3)

Treatment of 7-2 (1.04 g, 2.86 mmoles) with β-alanine t-butyl ester (0.54 g, 2.97 mmoles) as described for 1-11 gave crude 7-3. This was purified by flash chromatography on silica gel eluting with hexane(6)/acetone(4) to give 7-3 as an oil. $R_f$ 0.4 (silica gel, EtOAc(7)/hexane(3).

¹H NMR (300 MHz, CHCl₃) δ1.46 (18H, m), 1.60 (4H, m), 2.58 (2H, t), 2.83 (3H, s), 3.28 (2H, t), 3.70 (4H, m), 4.45 (2H, s), 7.52 (1H, d), 8.09 (1H, d), 8.11 (1H, s).

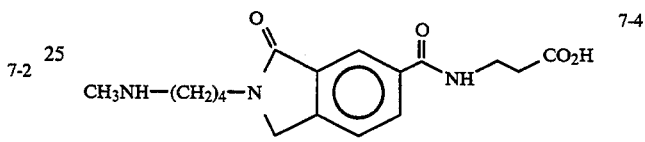

1-H-Isoindole-5-carboxamide, 2,3-dihydro-N-(2-carboxyethyl)-2-[4-(N-methylamino)butyl]-3-oxo (7-4)

Treatment of 7-3 with HCl gas in EtOAc solution as described for 6-4 gave 7-4 as a white solid.

¹H NMR (300 MHz, CD₃OD) d 1.67 (4H, m), 2.58 (5H, m), 2.95 (2H, t), 3.50 (4H, m), 4.50 (2H, s), 7.56 (1H, d), 7.97 (1H, d), 8.08 (1H, s).

SCHEME 8

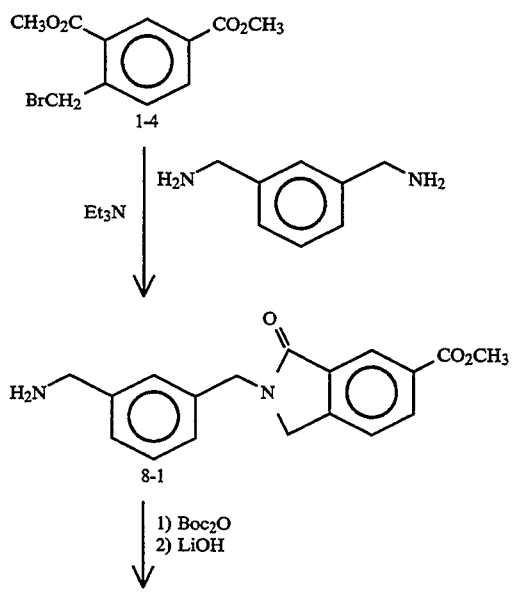

SCHEME 8
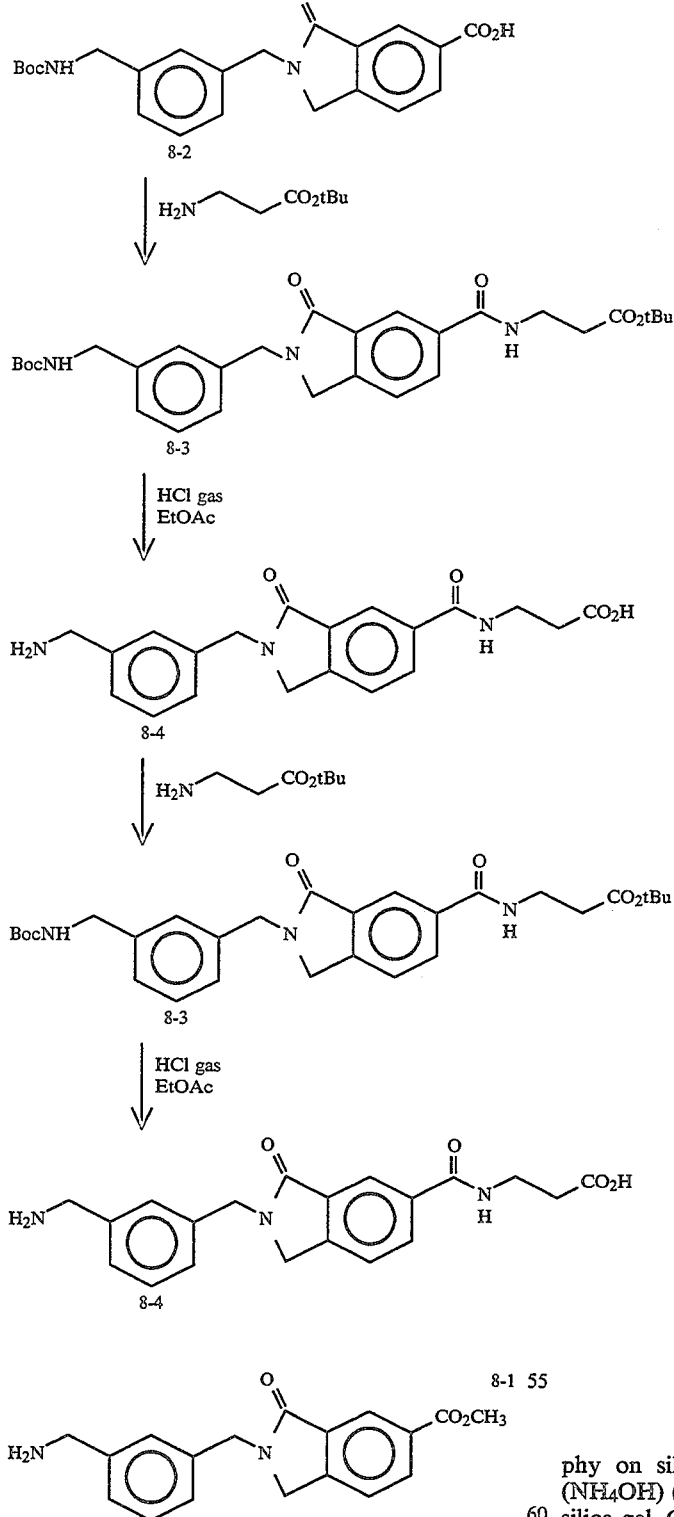
Methyl-1H-Isoindole-5-carboxylate, 2,3-dihydro-N-[(3-aminomethyl-phenyl)methyl]-3-oxo (8-1)
Treatment of 1-4 (2.15 g, 7.49 mmoles) with mxylenediamine (9.85 mmoles) as described for 1-9 gave crude 8-1. This was purified by flash chromatography on silica gel eluting with CH₃OH (10/CHCl₃ (NH₄OH) (90) to give pure 8-1 as a white solid. R_f 0.7 silica gel, CH₃OH (10)/CHCl₃ (NH₄OH) (90).
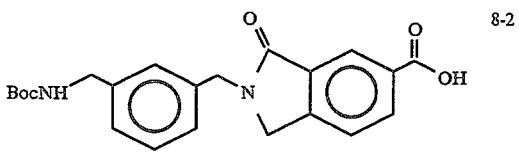

1-H-Isoindole-5-carboxylic acid, 2,3-dihydro-N-[(3-N-t-butyloxy-carbonylaminomethyl-phenyl)methyl]-3-oxo (8-2)

8-1 (1.76 g, 5.67 mmoles) was dissolved in CH$_2$Cl$_2$ (25 ml) and treated with Boc$_2$O (1.50 g, 6.87 mmoles) and Et$_3$N (6.45 mmoles) as described for 6-2 to give the desired N-protected ester. R$_f$ 0.25 (silica gel, EtOAc (1)/hexane (1)).

$^1$H NMR (300 MHz, CDCl$_3$) δ1.45 (9H, s), 1.65 (1H, m), 2.06 (2H, s), 4.30 (4H, m), 4.81 (2H, s), 7.27 (6H, m), 7.47 (1H, d), 8.22 (1H, d), 8.55 (1H, s).

This acid was treated with LiOH·H$_2$O as described for 6-2 to provide 8-2 as a white solid. R$_f$ 0.1 (silica gel, CHCl$_3$ (97)/CH$_3$OH (1)/HOAc (1)).

$^1$H NMR (300 MHz, CD$_3$OD) δ1.32 (9H, s), 4.12 (2H, s), 4.38 (2H, s), 4.73 (2H, s), 7.12 (4H, m), 7.25 (1H, m), 7.52 (1H, d).

1-H-Isoindole-5-carboxamide, 2,3-dihydro-N-[2-(t-butyloxycarbonyl)ethyl]-2-[(3-N-t-butyloxycarbonylaminomethylphenyl)methyl]-3-oxo (8-3)

Treatment of 8-2 (0.80 g, 2.02 mmoles) with b-alanine t-butyl ester (0.35 g, 2.28 mmoles), BOP (1.35 g, 3.04 mmoles) and Et$_3$N (14.3 mmoles) as described for 1-11 gave crude 8-3. This was purified by flash chromatography on silica gel eluting with hexane (6)/acetone (4) to give pure 8-3.

$^1$H NMR (300 MHz, CDCl$_3$) δ1.45 (9H, s), 1.47 (9H, s), 2.59 (2H, t), 3.72 (2H, m), 4.30 (4H, s), 4.82 (2H, s), 4.88 (1H, m), 7.28 (5H, m), 7.48 (1H, d), 8.08 (1H, d), 8.19 (1H, s).

1-H-Isoindole-5-carboxamide, 2,3-dihydro-N-(2-carboxyethyl)-2-[(3-aminomethyl-phenyl)methyl]-3-oxo (8-4)

8-3 (0.872 g, 1.67 mmoles) was dissolved in EtOAc (25 ml) and treated with HCl as described for 6-4 to give pure 8-4.

$^1$H NMR (300 MH$_3$, CD$_3$OD) δ2.58 (2H, t), 3.56 (2H, t), 4.00 (4H, s), 4.42 (2H, s), 7.32 (4H, m), 7.52 (1H, d), 7.95 (1H, d), 8.11 (1H, s).

SCHEME 9

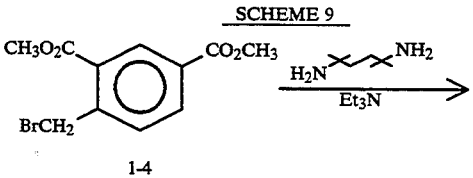

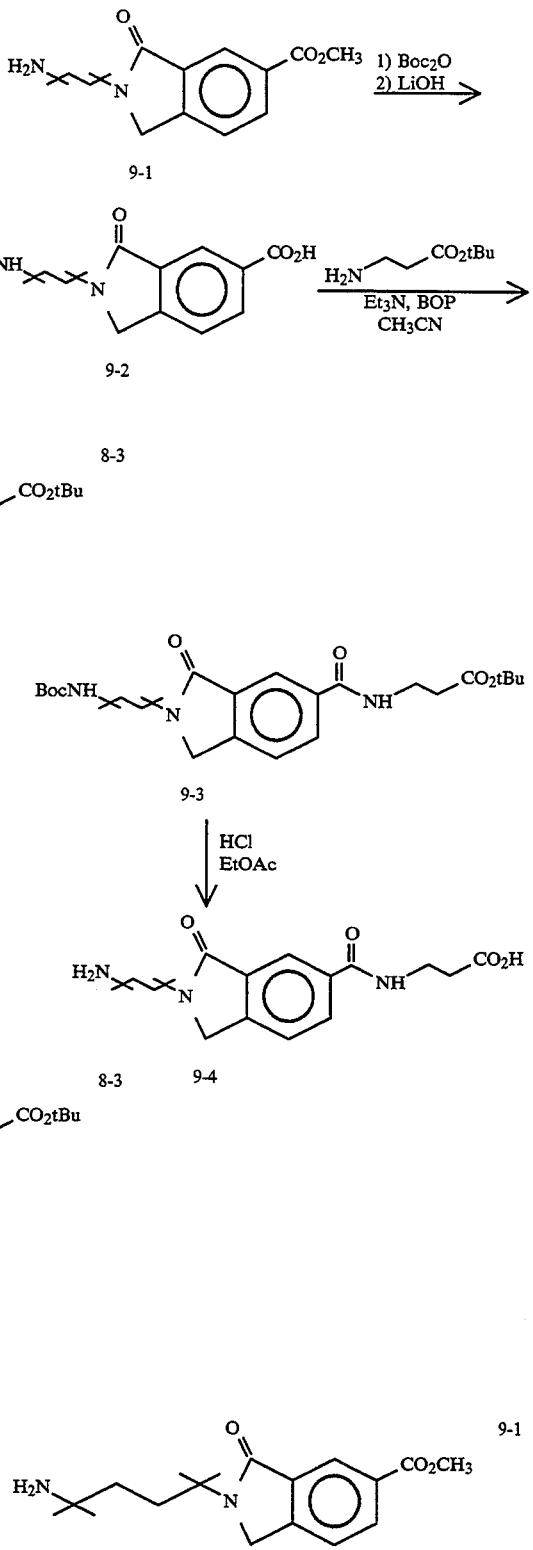

Methyl- 1H-Isoindole-5-carboxylate, 2,3-dihydro-N-[(4-amino-1,1,4,4-tetramethyl)butyl]-3-oxo (9-1)

Treatment of 1-4 (2.51 g, 8.74 mmoles) with 1,1,4,4,-tetramethyl-1,4-diaminobutane (1.50 g, 10.40 mmoles)

as described for 1-9 provided 9-1. $R_f$ 0.25 silica gel, 10% $CH_3OH$ in $CHCl_3/NH_4OH$.

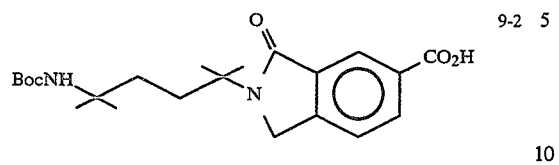

1-H-Isoindole-5-carboxylic acid, 2,3-dihydro-N-[(4-N-t-butyloxy-carbonylamino)-1,1,4,4-tetramethyl)butyl]-3-oxo (9-2)

9-1 was treated with $Boc_2O$ and $Et_3N$ as described for 6-2 to give the desired Boc-protected ester. $R_f$ 0.3 (silica gel, hexane (7)/acetone/3).

This ester (1.03 g, 2.46 mmoles) was treated with $LiOH \cdot H_2O$ (0.54 g, 12.9 mmoles) in THF (1)/$CH_3OH$ (1)/$H_2O$ (1) (60 ml) as described for 6-2 to give pure 9-2. $R_f$ 0.35 (silica gel, EtOAc).

$^1H$ NMR (300 MHz, $CD_3OD$) δ 1.10 (6H, s), 1.28 (9H, s), 1.48 (6H, s), 4.60 (2H, s), 7.55 (1H, d), 8.16 (1H, d), 8.26 (1H, s).

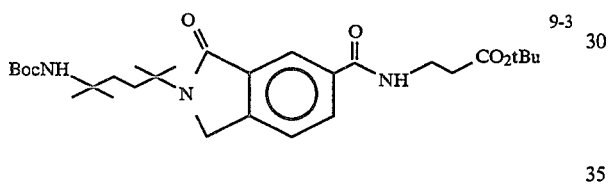

1-H-Isoindole-5-carboxamide, 2,3-dihydro-N-[2-t-butyloxycarbonyl)ethyl]-2-[4-(N-t-butyloxycarbonylamino)-(1,1,4,4-tetramethyl)butyl]-3-oxo (9-3)

9-2 (1.05 g, 2.83 mmoles) was treated with b-alanine t-butyl ester (0.48 g, 3.12 mmoles), $Et_3N$ (20.0 mmoles) and BOP (1.91 g, 4.31 mmoles) in $CH_3CN$ (15 ml) as described for 1-11 to provide crude 9-3. This was purified by flash chromatography on silica gel eluting with pet ether (7)/acetone (3) to give pure 9-3. $R_f$ 0.3 silica gel, pet ether (7)/acetone (3).

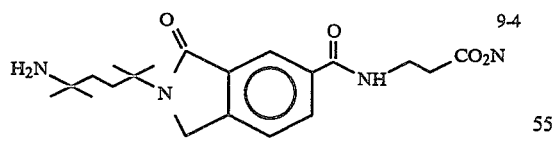

1-H-Isoindole-5-carboxamide, 2,3-dihydro-N-(2-carboxyethyl)-2-(4-amino-1,1,4,4-tetramethyl)butyl]-3-oxo (9-4)

9-3 (1.23 g) was dissolved in EtOAc (25 ml), cooled to −78° and treated with HCl gas as described for 6-4 to give pure 9-4.

$^1H$ NMR (300 MHz, $CD_3OD$) δ 1.26 (6H, s), 1.53 (5H, m), 2.59 (2H, t), 3.57 (2H, m), 4.63 (2H, s), 7.57 (1H, d), 7.98 (1H, d), 8.06 (1H, s).

SCHEME 10

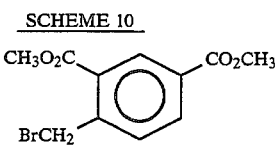

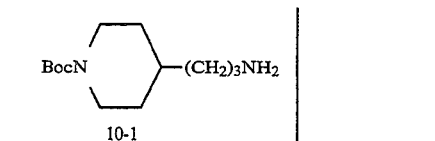

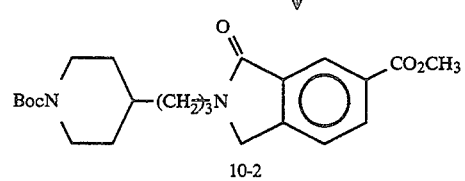

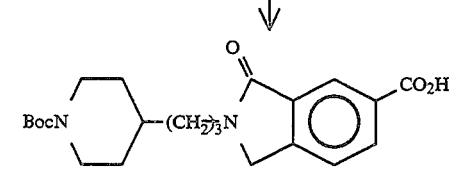

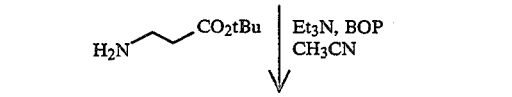

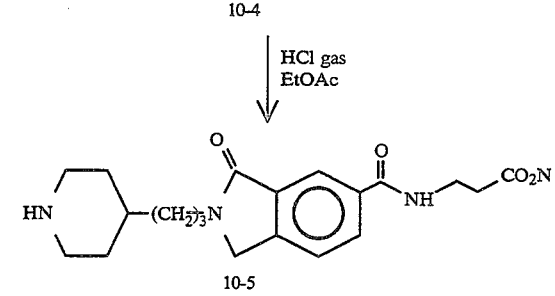

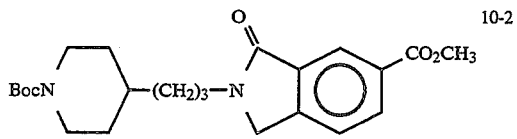

Methyl-1H-Isoindole-5-carboxylate, 2,3-dihydro-N-[3-(4-N-t-butyloxycarbonylpiperidinyl)-propyl]-3-oxo(10-2)

Treatment of 1-4 (4.59 g, 16.0 mmoles) with 3-(4-N-t-butyloxycarbonylpiperidinyl)propylamine (prepared from 1-6 by nitrile formation followed by catalytic hydrogenation) (4.36 g, 15.6 mmoles) as described for 1-9 gave crude 10-2. This was purified by flash chromatography on silia gel eluting with hexane (3)/ethyl acetate (1) to give pure 10-2.

$^1$H NMR (300 MHz, CDCl$_3$) δ1.10 (2H, m), 1.30 (2H, m), 1.45 (9H, s), 1.68 (4H, m), 2.66 (2H, m), 3.62 (2H, t), 3.95 (3H, s), 4.10 (2H, m), 4.44 (2H, s), 7.52 (1H, d), 8.23 (1H, d), 8.50 (1H, s).

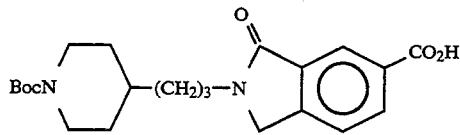

1-H-Isoindole-5-carboxylic acid, 2,3-dihydro-N[3-(4-N-t-butyloxy-carbonylpiperidinyl)-propyl]-3-oxo (10-3)

Treatment of 10-2 (2.79 g, 6.91 mmoles) with LiOH·H$_2$O (1.48 g, 35.2 mmoles) in THF (1)/MeOH (1)/H$_2$O (1) as described for 1-10 provided 10-3 as a white solid.

$^1$H NMR (300 MHz, CD$_3$OD) δ0.95 (2H, m), 1.23 (3H, m), 1.35 (9H, s), 1.66 (3H, m), 2.65 (2H, m), 3.56 (2H, t), 3.96 (2H, bd), 4.50 (2H, s), 7.60 (1H, d), 8.17 (1H, d), 8.30 (1H, s).

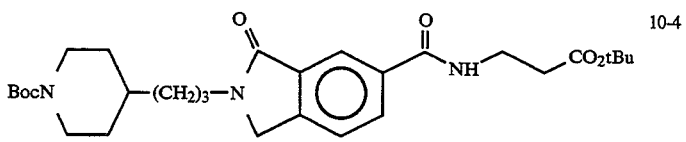

1-H-Isoindole-5-carboxamide, 2,3-dihydro-N-[3-(t-butyloxy-carbonyl)ethyl]-2-[3-(4-N-t-butyloxycarbonylpiperdinyl)propyl]-3-oxo (10-4)

Treatment of 10-3 (1.28 g, 3.28 mmoles) with b-alanine t-butyl ester (0.64 g, 3.52 mmoles), Et3N (3.3 mmoles), BOP (2.16 g) in CH$_3$CN as described for 1-11 gave crude 10-4. This was purified by flash chromatography on silica gel eluting with hexane (7)/acetone (3) to give pure 10-4.

$^1$H NMR (300 MHz, CDCl$_3$) δ1.09 (2H, m), 1.30 (3H, m), 1.45 (9H, s), 1.68 (4H, m), 2.62 (4H, m), 3.62 (2H, t), 3.70 (2H, t), 4.08 (2H, bd), 4.23 (2H, s), 7.52 (1H, d), 8.10 (1H, d), 8.13 (1H, s).

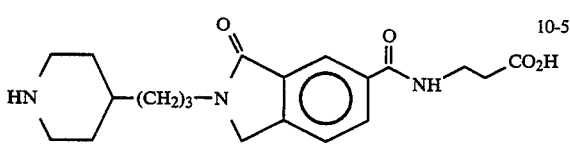

1-H-Isoindole-5-carboxamide, 2,3-dihydro-N-(2-carboxyethyl)-2-[3-(4-piperidinyl)-propyl]-3-oxo (10-5)

Treatment of 10-4 (1.18 g) in EtOAc (30 ml) −78° with HCl gas as described for 6-4 gave pure 10-5 as a white solid. R$_f$0.4 (silica gel, EtOAc).

$^1$H NMR (300 MHz, CD$_3$OD) δ1.30 (4H, m), 1.67 (4H, m), 1.89 (2H, bd), 2.60 (2H, t), 2.40 (2H, t), 3.19 (2H, bd), 3.58 (4H, m), 4.50 (2H, s), 7.60 (1H, d), 7.99 (1H, d), 8.08 (1H, s).

SCHEME 1

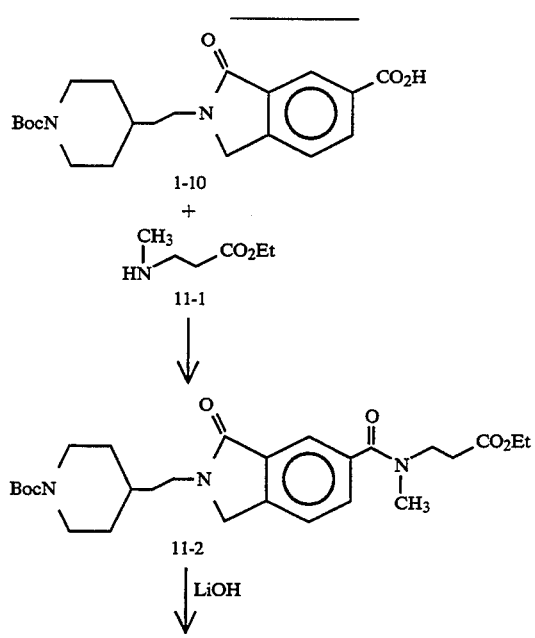

-continued
SCHEME 11

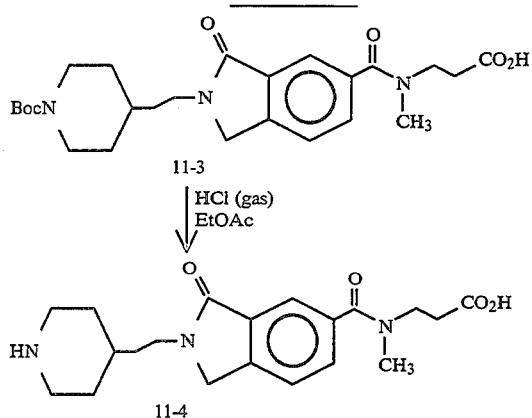

1-H-Isoindole-5-carboxamide, 2,3-dihydro-N-[N-methyl-N-2-(carboethoxy)ethyl]-2-[2-(4-N-t-butyloxycarbonylpiperidinyl)ethyl]-3-oxo (11-2)

Treatment of 1-10 (0.2 g, 0.54 mmoles) with ethyl 3-(N-methyl)aminopropionate (0.14 g, 1.08 mmoles) (Appl. Polymer Sci., 1969, 13, 227), N-methylmorpholine (1.08 mmoles), and BOP (0.35 g, 0.8 mmoles) in CH3CN (3 ml) as described for 1-11 gave crude 11-2. This was purified by flash chromatography on silica gel eluting with EtOAc to give pure 11-2 as a white solid.

$^1$H NMR (300 MHz, CD$_3$OD) δ1.20 (6H, m), 1.45 (9H, s), 1.67 (2H, q), 1.80 (2H, bd), 2.73 (2H, m), 3.00 (3H, s), 3.08 (1H, bs), 3.71 (2H, t), 3.84 (1H, m), 4.05 (4H, m), 4.17 (1H, m), 4.56 (2H, s), 7.66 (2H, m), 7.77 (1 H, s).

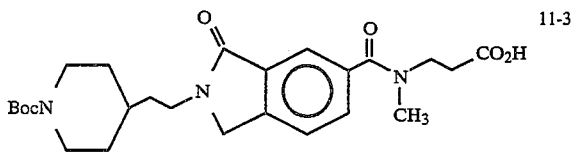

1-H-Isoindole-5-carboxamide, 2,3-dihydro-N-[N-methyl-N-(2-carboxy-ethyl)]-2-[2-(4-N-t-butyloxycarbonylpiperidinyl)ethyl]-3-oxo (11-3)

11-2 (0.23 g, 0.49 mmoles) was treated with LiOH·H$_2$O (0.096 g, 2.3 mmoles) as described for 8-2 to give 11-3 as a white solid.

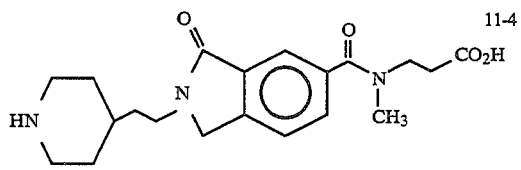

1-H-Isoindole-5-carboxamide, 2,3-dihydro-N-[N-methyl-N-(2-carboxy-ethyl)]-2-[(4-piperidinyl)ethyl]-3-oxo(11-4)

11-3 (0.2 g, 0.45 mmoles) in EtOAc was treated with HCl gas as described for 8-4 to give pure 11-4 as a white solid.

$^1$H NMR (300 MHz, CD$_3$OD) δ1.14 (1H, t), 1.37 (2H, m), 1.50 (1H, m), 1.63 (2H, q), 1.92 (2H, bd), 2.51 (1H, t), 2.67 (1H, t), 2.83 (2H, m), 3.31 (2H, bd), 3.54 (1H, t), 3.60 (2H, t), 3.73 (1H, t), 4.49 (2H, s), 7.57 (2H, q), 7.65 (1H, s).

SCHEME 12

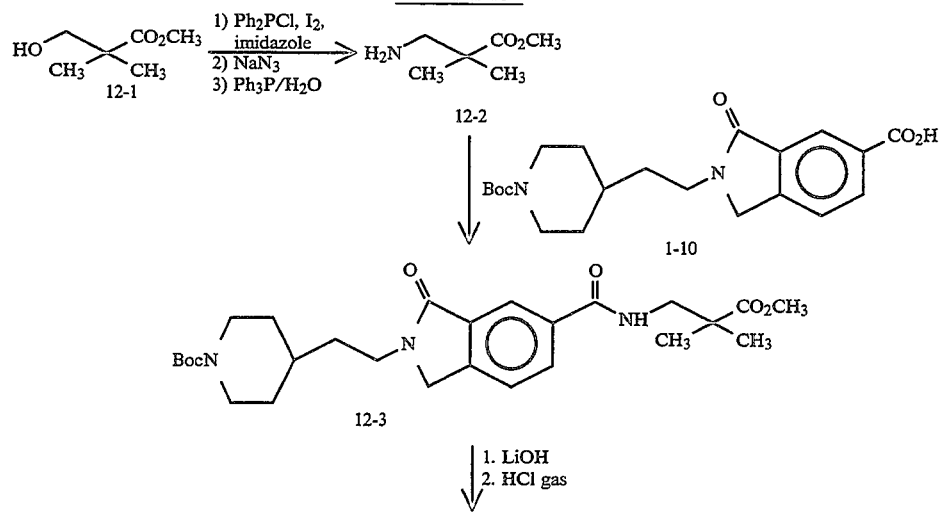

-continued
SCHEME 12

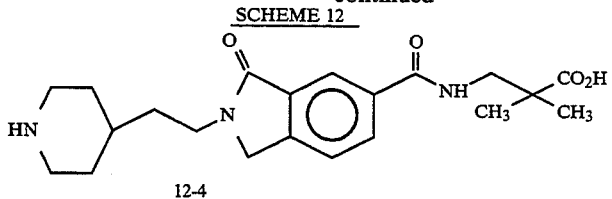

Methyl 3-amino-2,2-dimethylpropionate (12-2)

12-1 (Aldrich, 5.0 g, 38 mmoles) in toluene (150 ml) at room temperature was treated with chlorodiphenyl phosphine (49.4 mmoles) followed by imidazole (5.7 g, 83.6 mmoles) and $I_2$ (12.5 g, 49.4 mmoles) and the resulting brown solution was stirred for 0.5 hours. This mixture was poured into 150 ml saturated $Na_2CO_3$ solution and the organic layer was separated and washed with saturated $Na_2CO_3$ solvent, 5% $Na_2SO_4$ solution, $H_2O$, and 10% $KHSO_4$ solution. The nearly colorless organic layer was then washed with brine, dried ($Na_2SO_4$) and the solvent was removed to produce a yellow residue. This was purified by flash chromatography on silica gel eluting with hexane (6)/EtOAc (4) to give the desired iodo intermediate as an oil. $R_f$ 0.9 (silica gel, hexane (6)/EtOAc (4)).

$^1$H NMR (300 MHz, $CDCl_3$) $\delta$1.38 (6H, s), 3.40 (2H, s), 3.75 (3H, s).

This iodo compound (3.9 g, 16 mmoles) was dissolved in DMSO (80 ml) and treated with $NaN_3$ (2.1 g, 32 mmoles) at 70° for 2 hours. The cooled reaction next was diluted with EtOAc and extracted with $H_2O$ and brine. The organic phase was washed with brine, dried ($Na_2SO_4$) and the solvent was removed to give the desired azide as a foam.

$^1$H NMR (300 MHz, $CDCl_3$) $\delta$1.25 (6H, s), 3.45 (2H, s), 3.75 (3H, s).

This azide (2.0 g, 12.7 mmoles) was dissolved in THF (50 ml) and treated with $H_2O$ (25 ml) and triphenyl phosphine (13.3 g, 50.8 mmoles) at room temperature for 2 hours. The THF was removed under vacuum and the resulting residue was acidified to pH 2-3 with 10% $KHSO_4$ solution. This was filtered to remove triphenyl phosphine and the filtrate was extracted with EtOAc. The acidic aqueous phase was then basified with 10% NaOH and extracted with $Et_2O$. The combined ether extracts were washed with brine, dried ($Na_2SO_4$) and the solvent removed to give 12-2 as a clear oil. $R_f$ 0.35 (silica gel, $CH_2Cl_2$ (9)/$CH_3OH$ (1)/$H_2O$(1).

$^1$H NMR (300 MHz, $CD_3OD$) $\delta$1.22 (6H, s), 2.75 (2H, s), 3.75 (3H, s).

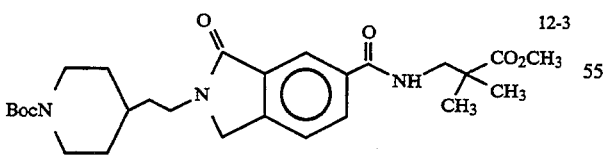

1-H-Isoindole-5-carboxamide, 2,3-dihydro-N-[(2-carbomethoxy-2methyl)propyl]-2-[2-(4-N-t-butyloxycarbonylpiperidinyl)ethyl]-3-oxo (12-3)

Treatment of 1-10 (1.0 g, 2.7 mmoles) with 12-2 (0.524 g, 4.0 mmoles), N-methylmorpholine (4.0 mmoles) and BOP (1.78 g, 4.0 mmoles) in $CH_3CN$ (15 ml) as described for 6-3 provided crude 12-3. This was purified by flash chromatography on silica gel eluting with EtOAc (9)/Hexane (1) to give pure 12-3 as a white solid.

$^1$H NMR (300 MHz, $CDCl_3$) $\delta$1.20 (2H, m), 1.33 (6H, s), 1.48 (9H, s), 1.80 (2H, bd), 2.71 (2H, bt), 3.64 (2H, d), 3.73 (2H, t), 3.77 (3H, s), 4.13 (2H, m), 4.44 (2H, s), 6.94 (1H, t), 7.57 (1H, d), 8.11 (1H, d), 8.13 (1H, s).

1-H-Isoindole-5-carboxamide, 2,3-dihydro-N-[(2-carboxy-2-methyl)-propyl]-2-[2-(4-piperidinyl)ethyl]-3-oxo (12-4).

12-3 (0.5 g, 1.0 mmoles) was treated with LiOH·$H_2O$ (0.216 g, 5.0 mmoles) as described for 6-2 to give the desired acid as a white solid.

$^1$H NMR (300 MHz, $CD_3OD$) $\delta$1.13 (2H, m), 1.25 (6H, s), 1.45 (9H, s), 1.65 (2H, m), 1.80 (2H, bd), 2.72 (2H, m), 3.68 (2H, m0, 3.70 (2H, t), 4.05 (2H, bd), 4.56 (2H, s), 7.67 (1H, d), 8.04 (1H, dd), 8.15 (s).

This acid (0.40 g) was dissolved in EtOAc and was treated with HCl gas as described for 6-4 to give pure 12-4 as a white solid.

$^1$H NMR (300 MHz, $D_2O$) d 1.14 (6H, s), 1.35 (2H, m), 1.49 (1H, m), 1.60 (2H, q), 1.90 (2H, bd), 2.81 (2H, t), 3.30 (2H, bd), 3.47 (2H, s), 3.57 (2H, t), 4.48 (2H, s), 7.55 (1H, d), 7.82 (1H, d), 7.90 (1H, s).

SCHEME 13

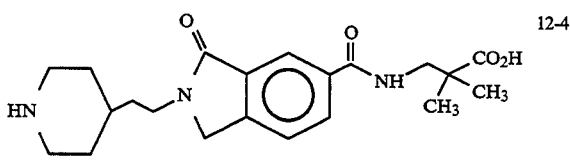

-continued
SCHEME 13

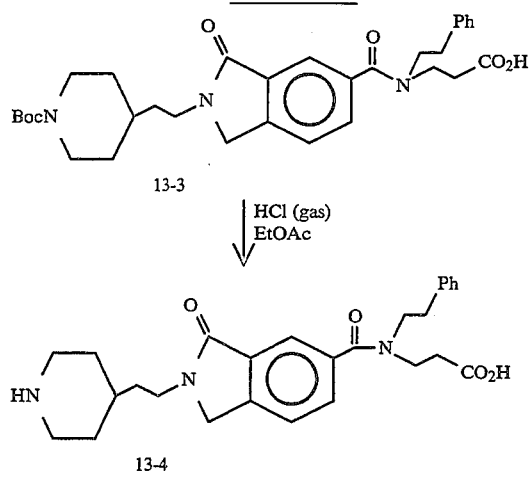

13-3

HCl (gas) ↓ EtOAc

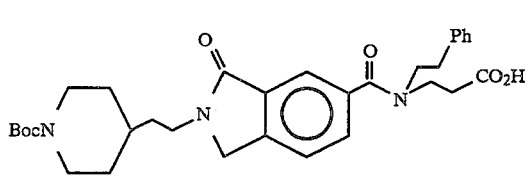

13-4

1-H-Isoindole-5-carboxamide,
2,3-dihydro-N:[N-phenethyl-N-2-carboethoxyethyl]-2-
[2-(4-N-t-butyloxycarbonylpiperidinyl)ethyl]-3-oxo
(13-2)

1-10 (0.388 g, 1.0 mmoles) was treated with ethyl 3-(N-phenethyl)aminopropionate (0.22 g, 1.0 mmoles) (prepared by treatment of phenethylamine with ethyl acrylate), triethylamine (0.243 g, 2.4 mmoles) and BOP (0.53 g, 1.2 mmoles) in DMF (15 ml) and the resulting solution was stirred at room temperature for 18 hours. The solvent was then removed and the residue was diluted with H₂O (100 ml) and extracted with EtOAc (3×100 ml portions). The organic phase was washed with 10% KHSO₄ solution, brine, saturated NaHCO₃ solution, brine and dried (Na₂SO₄). Solvent removal gave 13-2 as an oil.

¹H NMR (300 MHz, CDCl₃) δ1.07–1.35 (6H, m), 1.48 (9H, s), 1.62 (3H, m), 1.75 (2H, bd), 2.72 (4H, m), 3.00 (1H, m), 3.50 (2H, m), 3.67 (2H, t), 3.83 (2H, m), 4.10 (5H, m), 4.38 (2H, s), 6.94 (1H, bs), 7.30 (6H, m), 7.50 (1H, m), 7.67 (1H, m).

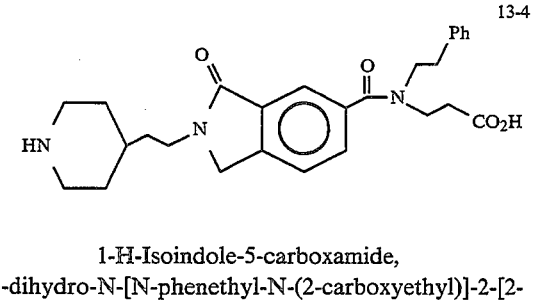

13-3

1-H-Isoindole-5-carboxamide,
2,3-dihydro-N-[N-phenethyl-N-(2-carboxyethyl)]-
2-[2-(4-N-t-butyloxycarbonylpiperidinyl)ethyl]-3-oxo
(13-3)

13-2 (0.60 g, 1.0 mmoles) was treated with LiOH·H₂O (0.127 g, 3.0 mmoles) as described for 6-2 to give 13-3 as a white solid. R/0.45 (silica gel, CHCl₃ (9)/MeOH (5)/HOAc (1).

¹H NMR (300 MHz, CDCl₃) δ1.17 (2H, m), 1.47 (9H, s), 1.63 (3H, m), 1.75 (2H, bd), 2.67 (2H, t), 2.80 (3H, m), 3.42 (1H, m), 3.57 (1H, m), 3.67 (2H, t), 3.80 (2H, m), 4.08 (3H, m), 4.37 (2H, s), 6.93 (1H, m), 7.25 (6H, m), 7.48 (1H, m), 7.70 (1H, m).

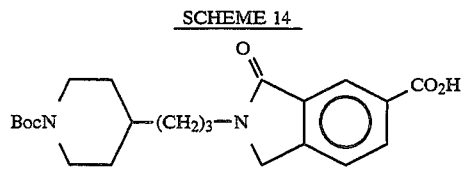

13-4

1-H-Isoindole-5-carboxamide,
2,3-dihydro-N-[N-phenethyl-N-(2-carboxyethyl)]-2-[2-
(4-piperidinyl)ethyl]-3-oxo (13-4)

13-3 was treated with HCl (gas) in EtOAc as described for 6-4 to give pure 13-4 as a white solid. R/0.25 (silica gel, EtOH (10)/H₂O (1)/NH₄OH (1)).

¹H NMR (300 MHz, CD₃OD) δ1.45 (2H, m), 1.62 (2H, m), 1.71 (2H, m), 2.07 (2H, bd), 2.45 (1H, m), 2.78 (2H, m), 2.95 (3H, m), 3.37 (3H, bd), 3.57 (1H, bt), 3.72 (2H, t), 3.83,(2H, m), 3.55 (2H, s), 6.95 (1H, m), 7.20 (4H, bs), 7.33 (1H, bs), 7.45 (1H, bs), 7.55 (1H, m), 7.66 (1H, m).

SCHEME 14

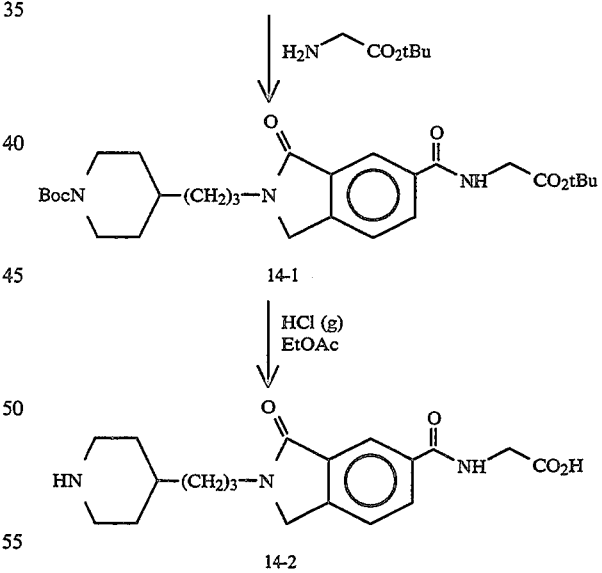

1-H-Isoindole-5-carboxamide,
2,3-dihydro-N-[t-butyloxycarbonyl-methyl]-2-[3-(4-N-t-butyloxycarbonylpiperidinyl)propyl]-3-oxo (14-1)

Treatment of 10-3 with glycine t-butyl ester as described for 6-3 gave 14-1.

¹H NMR (300 MHz, CDCl₃) δ1.13 (2H, m), 1.30 (2H, m), 1.41 (9H, s), 1.52 (9H, s), 1.73 (4H, m), 2.69 (2H, t), 3.65 (2H, t), 4.10 (2H, bd), 4.16 (2H, d), 4.45 (2H, s), 7.53 (1H, d), 8.10 (1H, d), 8.22 (1H, s).

1-H-Isoindole-5-carboxamide, 2,3,-dihydro-N-[carboxymethyl]-2-[3-(4-piperidinyl)-propyl]-3-oxo (14-2)

Treatment of 14-1 with HCl gas in EtOAc as described for 6-4 gave 14-2 as a white solid.

¹H NMR (300 MHz, CD₃OD) δ1.30 (4H, m), 1.65 (4H, m), 1.90 (2H, bd), 2.59 (2H, t), 2.90 (2H, t), 3.30 (2H, bd), 3.58 (4H, m), 4.50 (2H, s), 7.58 (1H, d), 7.98 (1H, d), 8.07 (1H, s).

Methyl-1H-Isoindole-5-carboxylate, 2,3-dihydro-N-[2-(4-aminobutyl)]-3-oxo(15-1)

1-4(2.56 g, 8.92 mmoles)was treated with 1,4-diaminobutane (10.9 mmoles) as described for 1-9 to give crude 15-1. This was purified by flash chromatography on silica gel eluting with 25% CH₃OH/CHCl₃(NH₃) to give pure 15-1 as a solid.

¹H NMR (300 MHz, CD₃OD) δ1.61 (2H, m), 1.75 (2H, m), 2.90 (2H, t), 3.24 (1H, m), 3.63 (2H, t), 3.85 (3H, s), 4.53 (2H, s), 7.62 (1H, d), 8.18 d) 8.28 s).

1-H-Isoindole-5-carboxylic acid-2,3-dihydro-N-[2-(4-N-t-butyloxy-carbonyamino)-butyl]-3-oxo(15-2)

15-1 (1.11 g, 4.24 mmoles) was treated with Boc₂O (1.17 g, 5.36 mmoles) as described for 3-1. Crude residue was purified by flash chromatography on silica gel eluting with 30% acetone/hexane to give the desired protected ester as an oil. R𝑓0.7 silica gel, 30% acetone/hexane.

This ester (0.85 g, 2.34 mmoles) was dissolved in THF(1)/CH₃OH(1)/H₂O(1) (30 ml) and treated with LiOH·H₂O (0.52 g, 12.4 mmoles) as described for 3-2 to give 15-2 as a white solid.

¹H NMR (300 MHz, CD₃OD) δ1.36 (9H, s), 1.44 (2H, m), 1.66 (4H, m), 3.01 (2H, t), 3.60 (2H, t), 4.54 (2H, s), 7.62 (1H, d), 8.20 (1H, d), 8.35 (1H, s).

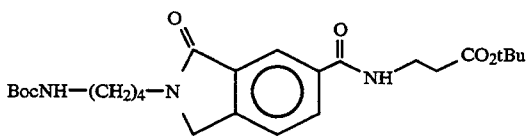

1-H-Isoindole-5-carboxamide, 2,3-dihydro-N-[2-(t-butyloxycarbonyl)-ethyl]-2-[4-(N-t-butyloxycarbonyl)butyl]-3-oxo(15-3)

Treatment of 15-2 (0.75 g, 2.07 mmoles) in CH₃CN (12 ml) with b-alanine t-butyl ester (0.39 g, 2.54 mmoles), Et₃N (14.3 mmoles) and BOP (1.40 g, 3.16 mmoles) as described for 3-3 gave crude 15-3. This was purified by flash chromatography on silica gel eluting with 75% EtOAc/hexane to give pure 15-3 as a white solid. R𝑓0.25 (silica gel, 75% EtOAc/hexanes).

¹H NMR (300 MHz, CDCl₃) δ1.42 (9H, s), 1.44 (9H, s), 1.52 (2H, m), 1.77 (2H, m), 2.55 (2H, t), 3.19 (2H, m), 3.67 (4H, m), 4.43 (2H, s), 7.00 (1H, bt), 7.52 (1H, d), 8.09 (1H, d), 8.10 (1H, s).

1-H-Isoindole-5-carboxamide, 2,3-dihydro-N-[2-carboxyethyl]-2-[4-aminobutyl]-3-oxo(15-4)

Treatment of 15-3 (0.51 g, 1.07 mmoles) in EtOAc with HCl gas as described for 3-4 provided pure 15-4 as a white solid.

¹H NMR (300 MHz, D₂O), δ1.63 (4H, m), 2.64 (2H, t), 2.92 (2H, t), 3.52 (4H, m), 4.46 (2H, s), 7.55 (1H, d), 7.81 (1H, d), 7.85 (1H, s).

1-H-Isoindole-5-carboxamide, 2,3-dihydro-N-[ethyl-3-(2(S)-amino-propionate)]-2-[2-(4-N-t-butyloxycarbonylpiperidinyl]-3-oxo (16-2)

A solution of 1-10 (1.5 g, 3.87 mmoles) in DMF (15 ml) at room temperature was treated with carbonyl diimidazole (0.627 g, 3.87 mmoles) (CDI) and after 2 hours this solution was added dropwise to a DMF solution of ethyl 2(S),3-diaminopropionate (1.5 g, 7.74 mmoles) and N-methylmorpholine (23.2 mmoles). The reaction mixture was then stirred at room temperature for 16 hrs.

The solvent was then removed and the residue was dissolved in EtOAc and 10% aqueous KHSO₄ solution. The aqueous phase was separated, washed with EtOAc and made basic to pH 12. This was extracted with EtOAc, and the extracts were combined, washed with brine, and dried (Na₂SO₄). Solvent removal provided 16-2.

¹H NMR (300 MHz, CD₃OD) δ1.24 (2H, m), 1.46 (3H, t), 1.43 (9H, s), 1.66 (2H, q), 1.80 (2H, bd), 3.67 (4H, m), 4.10 (2H, bd), 4.17 (2H, q), 4.57 (2H, s), 7.04 (1H, d), 7.67 (1H, m), 8.06 (1H, m), 8.17 (1H, d).

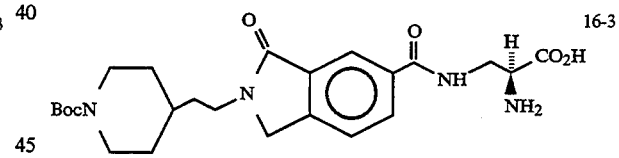

1-H-Isoindole-5-carboxamide, 2,3-dihydro-N-[3-[2(S)-aminopropanoic acid]-2-[2-(4-N-t-butyloxycarbonylpiperidinyl]-3-oxo (16-3)

Treatment of 16-2 (0.6 g, 1.2 mmoles) with LiOH·H₂O (0.25 g, 6.0 mmoles) as described for 1-10 gave 16-3.

¹H NMR (300 MHz, D₂O) δ0.92 (2H, m), 1.27 (9H, s), 1.46 (4H, m), 2.58 (2H, t), 3.48 (4H, m), 3.83 (2H, bd), 4.38 (2H, s), 6.96 (1H, s), 7.50 (1H, d), 7.82 (1H, d), 7.87 (1H, s).

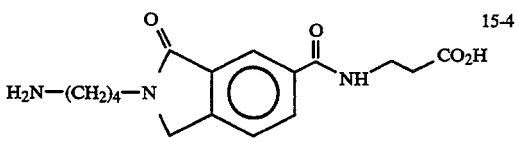

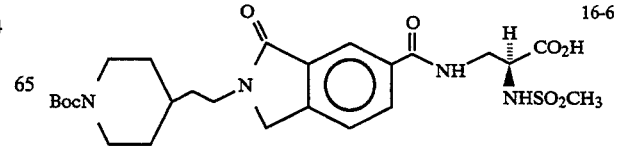

1-H-Isoindole-5-carboxamide, 2,3-dihydro-N-[3-[2(S)-methylsulfonylamino)propanoic acid)]-2-[2-(4-N-t-butyloxycarbonylpiperidinyl]-3-oxo (16-6)

A solution of 16-6 (0.55 g, 1.2 mmoles) in $H_2O$ (15 ml)/dioxane (3 ml) was cooled to 0°–10° and treated with 1N NaOH soln. (1.5 ml) and methane sulfonyl chloride (2.4 mmoles) in 3 ml dioxane was added dropwise while also adding 1N NaOH solution to keep the pH at 10-12. This cycle of $CH_3SO_2Cl$ addition at basic pH was carried out 5 times at which point all 16-6 was consumed. The acidity was carefully adjusted to pH 2-3 with 10% $KHSO_4$ solution and this was extracted with EtOAc (4 portions). The combined organics were washed with brine, dried ($Na_2SO_4$) and the solvent removed. The residue was purified by flash chromatography on silica gel eluting with $CH_2Cl_2$ (9)/MeOH (0.8)/HOAc (0.8) to give 16-6 as a white solid. $R_f$ 0.31.

$^1$H NMR (300 MHz, $CD_3OD$) δ1.25 (2H, m), 1.45 (9H, s), 1.65 (2H, q), 1.80 (2H, bd), 2.72 (2H, m), 2.97 (3H, s), 3.70 (3H, m), 3.86 (1H, m), 4.05 (2H, bd), 4.34 (1H, m), 4.56 (2H, s), 7.66 (1H, d), 8.08 (1H, d), 8.9 (1H, s).

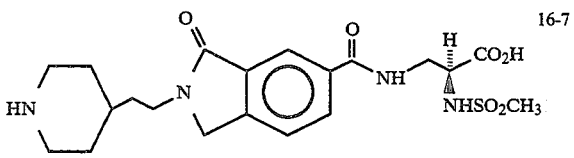

1-H-Isoindole-5-carboxamide, 2,3-dihydro-N-[3-(2(S)-methylsulfonylamino)propionic acid]-2-[2-(4-piperidinyl)ethyl]-3-oxo (16-7)

Treatment of 16-6 (0.22 g, 0.39 mmoles) with HCl gas in EtOAc as described for 1-12 gave 16-7 as a white solid.

$^1$H NMR (300 MHz, $D_2O$) δ1.35 (2H, m), 1.59, (2H, m), 1.87 (2H, bd), 2.78 (2H, bt), 2.95 (3H, m), 3.27 (2H, bd), 3.55 (3H, m), 3.78 (1H, m), 4.20 (1H, m), 4.48 (2H, s), 7.56 (1H, m), 7.87 (1H, m), 7.95 (1H, bs).

1-H-Isoindole-5-carboxamide, 2,3-dihydro-N-[3-(2(S)-n-butylsulfonylamino)-propanoic acid]-2-[2-(4-N-t-butyloxycarbonylpiperidinyl)]-3-oxo (16-8)

Treatment of 16-3 (0.836 mmoles) with n-butylsulfonyl. chloride (1.67 mmoles) as described for 16-6 gave 16-8 as a white solid.

$^1$H NMR (300 MHz, $CD_3OD$) δ0.85 (6H, m), 1.13 (2H, m), 1.35 (4H, m), 1.45 (9H, s), 1.65 (2H, m), 1.75 (2H, m), 2.70 (2H, m), 3.04 (2H, t), 3.68 (2H, m), 3.83 (1H, m), 4.04 (2H, bd), 4.53 (2H, s), 7.62 (1H, d), 8.05 (1H, d), 8.18 (1H, s).

1-H-Isoindole-5-carboxamide, 2,3-dihydro-N-[3-(2(S)-n-butylsulfonylamino)propionic acid]-2-[2-(4-piperidinyl)ethyl]-3-oxo (16-9)

Treatment of 7-8 in EtOAc with HCl gas as described for 1-12 gave pure 16-9 as a white solid.

$^1$H NMR (300 MHz, $CD_3OD$) δ0.59 (2H, t), 1.12 (2H, m), 1.35 (2H, m), 1.50 (2H, m), 1.59 (2H, m), 1.90 (2H, bd), 2.80 (2H, t), 2.98 (2H, t), 3.29 (2H, bd), 3.42 (1H, m), 3.60 (2H, t), 3.70 (1H, m), 4.50 (2H, s), 7.59 (1H, d), 7.91 (1H, d), 7.98 (1H, s).

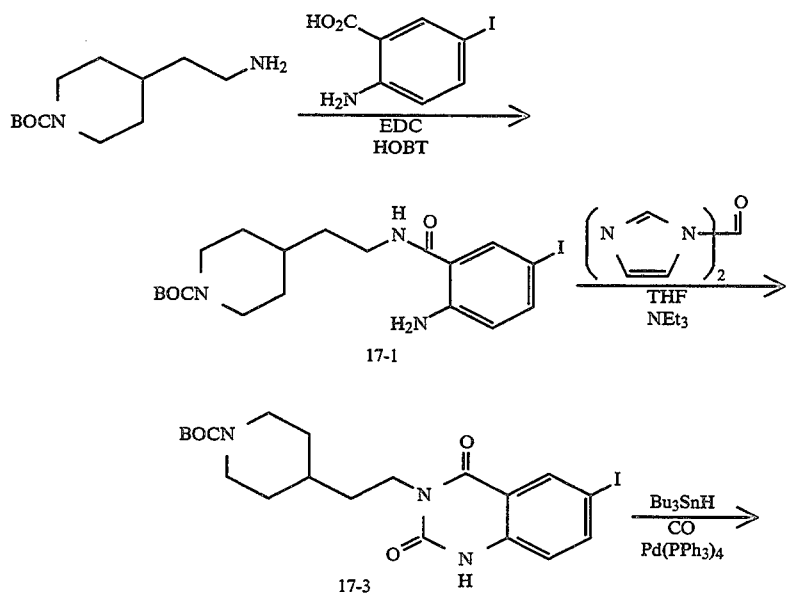

SCHEME 17 -continued

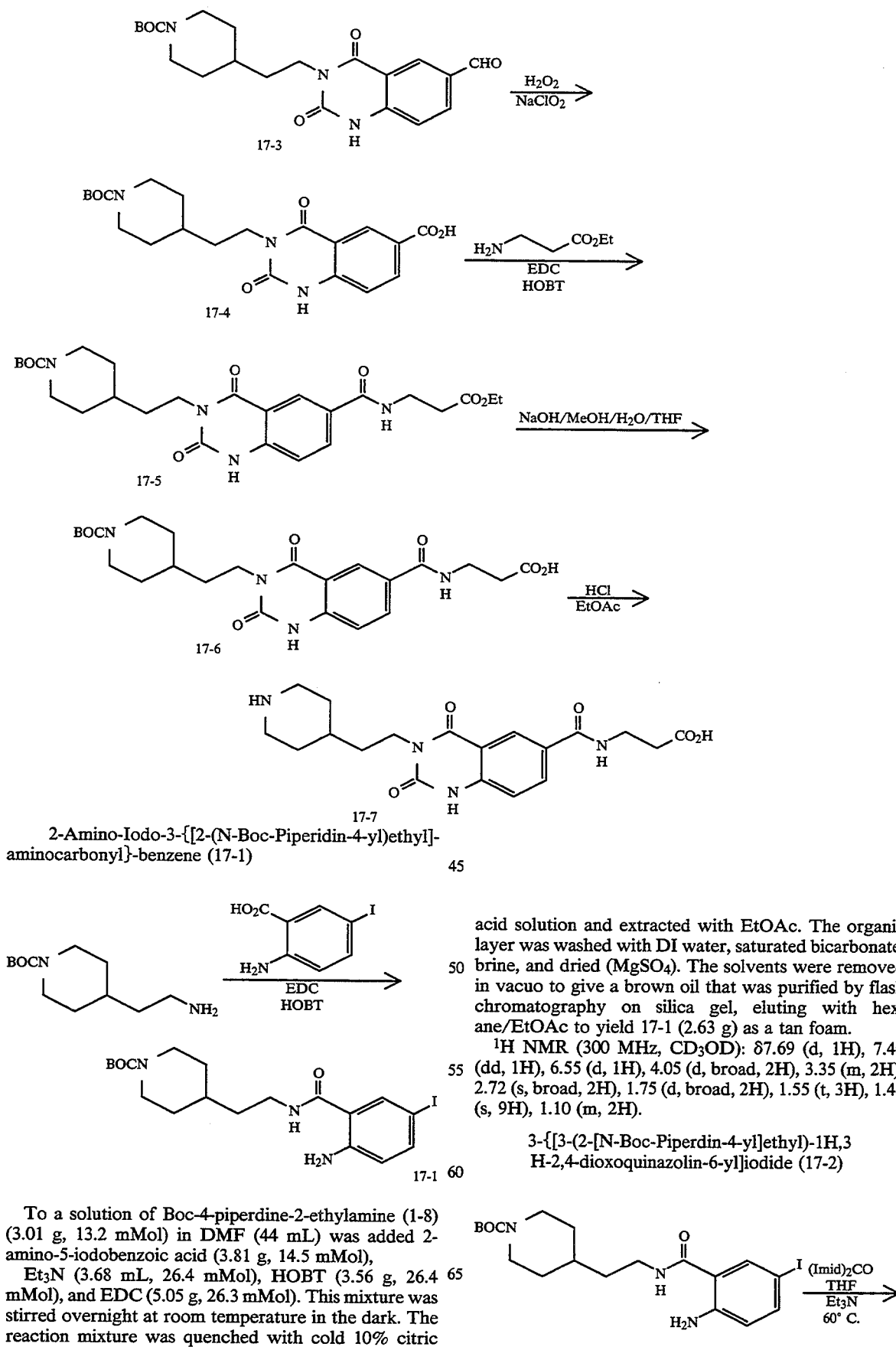

2-Amino-Iodo-3-{[2-(N-Boc-Piperidin-4-yl)ethyl]-aminocarbonyl}-benzene (17-1)

To a solution of Boc-4-piperdine-2-ethylamine (1-8) (3.01 g, 13.2 mMol) in DMF (44 mL) was added 2-amino-5-iodobenzoic acid (3.81 g, 14.5 mMol), Et₃N (3.68 mL, 26.4 mMol), HOBT (3.56 g, 26.4 mMol), and EDC (5.05 g, 26.3 mMol). This mixture was stirred overnight at room temperature in the dark. The reaction mixture was quenched with cold 10% citric acid solution and extracted with EtOAc. The organic layer was washed with DI water, saturated bicarbonate, brine, and dried (MgSO₄). The solvents were removed in vacuo to give a brown oil that was purified by flash chromatography on silica gel, eluting with hexane/EtOAc to yield 17-1 (2.63 g) as a tan foam.

¹H NMR (300 MHz, CD₃OD): δ7.69 (d, 1H), 7.40 (dd, 1H), 6.55 (d, 1H), 4.05 (d, broad, 2H), 3.35 (m, 2H), 2.72 (s, broad, 2H), 1.75 (d, broad, 2H), 1.55 (t, 3H), 1.45 (s, 9H), 1.10 (m, 2H).

3-{[3-(2-[N-Boc-Piperdin-4-yl]ethyl)-1H,3H-2,4-dioxoquinazolin-6-yl]iodide (17-2)

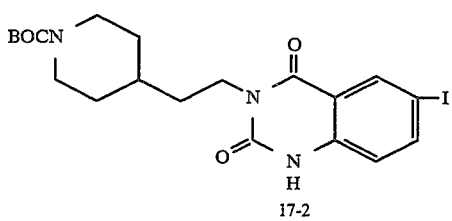

Aniline 17-1 ( 1.20 g, 2.54 mMol) and 1,1-carbonyldiimidazole (0.517 g, 3.19 mMol) were refluxed for 29 h in THF (35 mL) in the presence of Et3N (1.5 mL, 10.77 mMol). The solvent was removed in vacu, 10% citric acid solution added and extracted with $CH_2Cl_2$. The organic layer was washed with DI water and brine, dried ($MgSO_4$), and concentrated to give a brown foam that was purified by methanolic trituration to yield cyclized iodide 17-2 (0.882 g, 1.77 mMol).

$^1$H NMR (300 MHz, DMSO): δ8.14 (d, 1H), 7.91 (dd, 1H), 6.98 (d, 1H), 2.65 (s, broad, 2H), 1.68 (d, 2H), 1.45 (t, 2H), 0.95 (m, 2H).

3-{[3-(2-[N-Boc-Piperidin-4-yl]ethyl)- 1H,3 H-2,4-dioxoquinazolin-6-yl]carboxaldehyde (17-3)

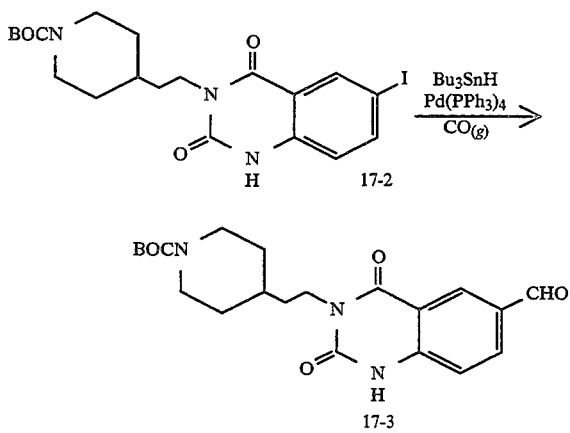

Aryl iodide 17-2 (0.102 g, 0.20 mMol) and tetrakis(triphenylphosphine)palladium (0) (0.011 g, 0.0099 mMol) were heated to 50° C. under an atmosphere of carbon monoxide. Tributyltin hydride (0.06 mL, 0.22 mMol) in toluene (1 mL) was added dropwise over 3H period to the heated reaction mixture. The mixture was stirred for 2 h at 50° C. and then overnight at room temperature. The solvent was removed in vacuo and the residue was purified by flash chromatography on silica gel, eluting with hexane/EtOAc to give aldehyde 17-3 (0.085 g, 0.20 mMol) as a pale yellow solid.

$^1$H NMR (300 MHz, CDCl3): δ10.03 (s, 1H), 9.52 (s, 1H), 8.62 (d, 1H), 8.18 (dd, 1H), 7.39 (d, 1H), 4.12 (m, 4H), 2.71 (t, 2H), 1.80 (d, 2H), 1.67 (m, 2H), 1.53 (m, 1H), 1.46 (s, 9H), 1.21 (m, 2H). 3-{[3-(2-[N-Boc-Piperidin-4-yl]ethyl)- 1H,3 H-2,4-dioxoquinazolin-6-yl[carboxylic acid (17-4)

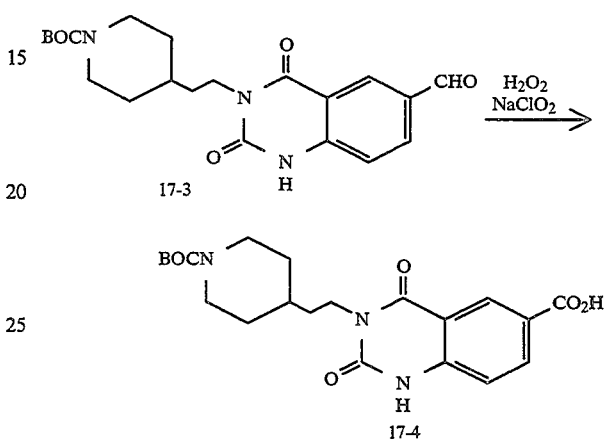

A solution of aldehyde 17-3 (0.244 g, 0.61 mMol) in $CH_3CN$ (3.5mL)/MeOH (5 mL)/$CH_2Cl_2$ (4.5 mL) was treated with hydrogen peroxide (42 μL, 30% solution, 0.41 mMol) and dibasic sodium phosphate buffer (0.025 g, 0.18 mMol)in water (0.4 mL). This mixture was cooled to 0° C., then sodium chlorite (0.162 g, 1.79 mMol) in water (1.5 mL) was added. This mixture was stirred at room temperature for 2.75 h, then organic solvents removed in vacu and diluted with DI water (10 mL). Citric acid solution (10%, 15 mL) was added and extracted into EtOAc. The organic layer was washed with brine, dried ($MgSO_4$), and concentrated to give acid 17-4 (0.216 g, 0.52 mMol) as an off-white solid.

$^1$H NMR (300 MHz, CD3OD): δ8.68 (d, 1H), 8.23 (dd, 1H), 7.22 (d, 1H), 4.10 (m, 4H), 2.68 (t, 2H), 1.81 (d, 2H), 1.62 (m, 2H), 1.42 (s, 9H), 1.07 (m, 2H). 3-{[3-(2-[Piperidin-4-yl]ethyl)-1H,3 H-2,4-dioxoquinazolin-6-yl]carbonylamino}propionic acid, trifluoroacetate salt (17-7)

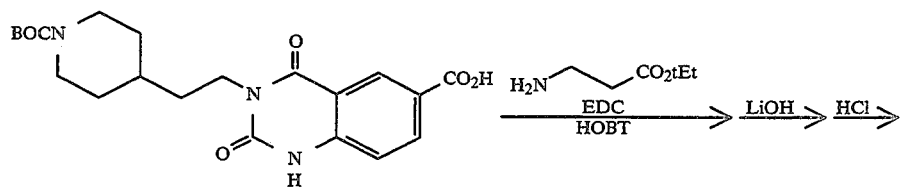

-continued

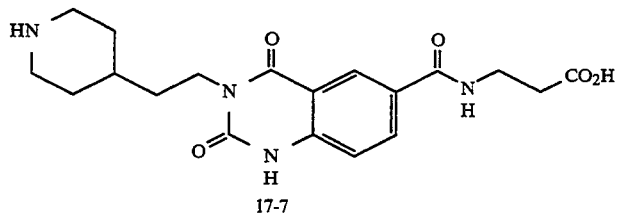

17-7

Acid 17-4 (0.102 g, 0.25 mMol) was coupled with β-alanine ethyl ester hydrochloride (0.069 g, 0.38 mMol) as described for 17-1 using EDC (0.094 g, 0.49 mMol), HOBT (0.067 g, 0.05 mMOL), DMF (0.82 mL), and Et₃N (70 μL, 0.50 mMol) to give 17-5 (0.137 g, 0.25 mMol) as a white foam.

¹H NMR (300 Mhz, CDCl₃): δ10.71 (s, 1H), 8.48 (d, 1H), 8.17 (dd, 1H), 7.23 (m, 2H), 4.10 (m, 4H), 3.70 (dd, 2H), 2.68 (t, 2H), 2.57 (t, 2H), 1.75 (d, 2H), 1.62 (m, 2H), 1.50 (m, 1H), 1.44 (s, 9H), 1.20 (m, 4H).

A solution of ester 17-5 (0.102 g, 0.19 mMol) in THF (5 mL)/MeOH (2 mL)/1 N LiOH (5 mL) was stirred for 4 h at room temperature. The reaction mixture was diluted with EtOAc and acidified to pH~3 with 10% citric acid solution. The layers were separated and the organic layer was washed with DI water and brine, dried (MgSO₄), and concentrated to give acid 17-6 (0.102 g, 0.02 mMol) as white solid.

Acid 17-6 (0.090 g, 0.18 mMol) was suspended in EtOAc (10 mL) cooled to 0° C., then HCl(g) bubbled through for 1h. The solvent was removed in vacuo and crude material purified by preparative HPLC (λ=254 nm) to give 17-7.

¹H NMR (300 MHz, D₂O): δ8.12 (d, 1H), 7.95 (dd, 1H), 7.19 (d, 1H), 3.97 (t, 2H), 3.68 (t, 2H), 3.44 (d, 2H), 3.00 (m, 2H), 2.72 (t, 2H), 2.10 (d, 2H), 1.63 (m, 3H), 1.46 (m, 2H).

SCHEME 18

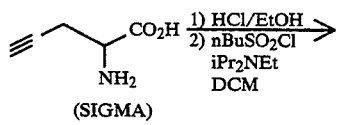

(SIGMA)

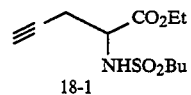

18-1

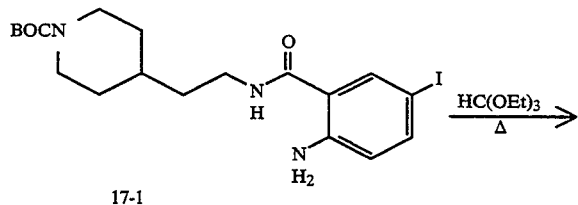

17-1

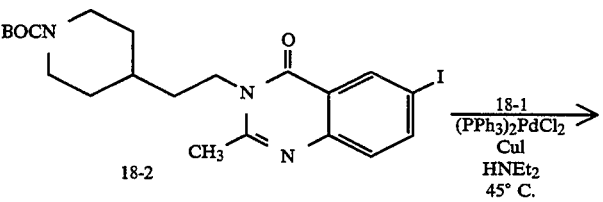

18-2

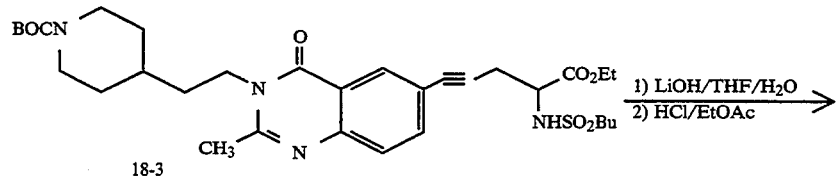

18-3

SCHEME 18 -continued

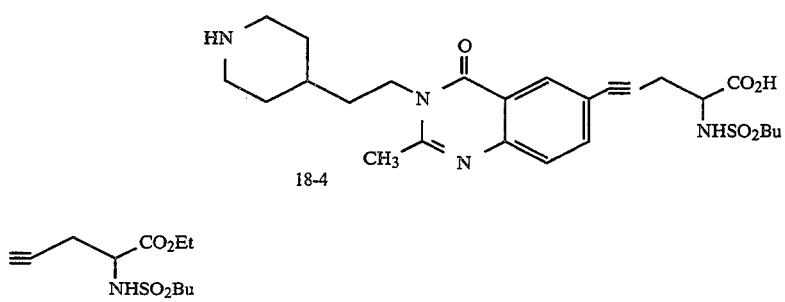

2-(Butanesulfonylamino)pent-4-ynoic acid, ethyl ester (18-1)

A solution of propargyl glycine ethyl ester hydrochloride (from treatment of 2.0 g (17.7 mmol) with EtOH/HCl at reflux) in $CH_2Cl_2$ (30 μl) and 10 ml (57 mmol) diisopropylethylamine was cooled to 0° C. and 35 ml of butanesulfonyl chloride added dropwise. After 30 minutes, reaction mixture was poured into the cold 10% citric acid solution and saturated with ether. The organic phase was washed with $NaHCO_3$ solution, brine and dried ($MgSO_4$). The crude product was purified by flash column chromatography to afford 2.6 g of 18-1.

NMR (300 MHz, $CDCl_3$): 5.12 (d, 1H), 4.27 (m, 3H), 3.06 (m, 2H), 2.68 (m, 2H), 2.09 (t, 1H), 1.83 (m, 2H), 1.45 (m, 2H), 1.31 (t, 3H), 0.95 (t, 1H).

3 h under an atmosphere of argon. Excess reagent was removed in vacu and the crude material was purified by flash chromatography on silica gel (hexane/EtOAc) to yield cyclized iodide 18-2 (0.170 g, 0.40 mMol) as a white foam.

$^1$H NMR (300 MHz, $CDCl_3$): δ8.55 (d, 1H), 7.95 (dd, 1H), 7.30 (d, 1H), 4.11 (m, 4H), 2.74 (t, 2H), 2.62 (s, 3H), 1.77 (d, 2H), 1.63 (m, 3H), 1.45. (s, 9H), 1.22 (m, 2H).

A mixture of iodide 18-2 (0.251 g, 0.50 mMol), acetylene 18-1 (0.141 g, 0.54 mMol) bis(triphenylphosphine)-palladium (II) chloride (0.0433 g, 0.062 mMol), and copper (I) iodide (0.0375 g, 0.20 mMol) in diethylamine (5 mL) was heated to 45° C. under an inert atmosphere for 1 h. The reaction mixture was quenched with 10% citric acid solution and extracted with EtOAc. The organic layer was washed with DI water, saturated bicarbonate, and brine, dried ($MgSO_4$), and concen-

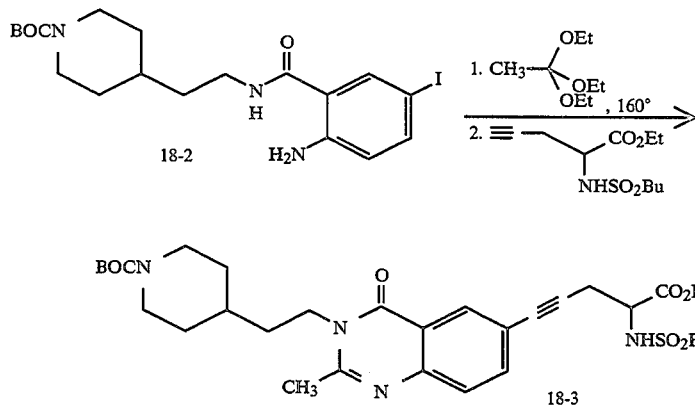

2-Butanesulfonylamino-5-[3-(2-[N-Boc-piperidin-4-yl]ethyl)-3H,4-oxoquinazolin-6-yl]pent-4-ynoic acid, ethyl ester (18-3)

A mixture of aniline 17-1 (0.204 g, 0.43 mMol) and triethylorthoacetate (10 mL) was heated to 160° C. for trated to give brown oil that was purified by silica gel chromatography (hexane/EtOAc) to yield 18-3.

$^1$H NMR (300 MHz, $CDCl_3$): δ8.22 (d, 1H). 5.35 (d, 1H), 4.32 (m, 3H), 4.11 (m, 4H), 3.06 (m, 4H), 2.73 (m, 2H), 2.64 (s, 3H), 1.80 (m, 4H), 1.63 (m, 3H), 1.46 (s, 9H), 1.45–1.15 (m, 9H), 0.91 (z, 3H).

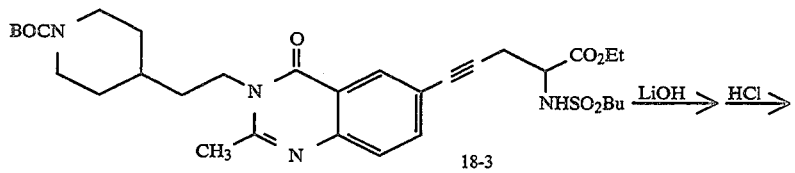

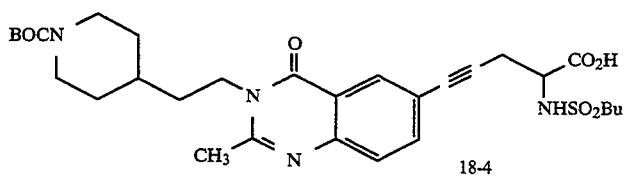
2-Butanesulfonamino-5-[3-(2[piperidin-4-yl]ethyl)-3H-4-oxoquinazolin-6-yl]pent-4-ynoic acid, trifluoroacetate salt (18-4)
18-3 was hydrolyzed, deprotected, and purified in the same way as 17-5 to give 18-4.
$^1$H NMR (300 MHz, D$_2$O): δ 8.05 (d, 1H), 7.75 (dd, 1H), 7.41 (d, 1H), 4.18 (t, 1H), 4.04 (m, 2H), 3.29 (d, 2H), 3.08 (t, 2H), 2.86 (m, 4H), 2.67 (s, 3H), 1.92 (d, 2H), 1.59 (m, 5H), 1.32 (m, 2H), 1.16 (m, 2H), 0.63 (t, 3H).
SCHEME 19
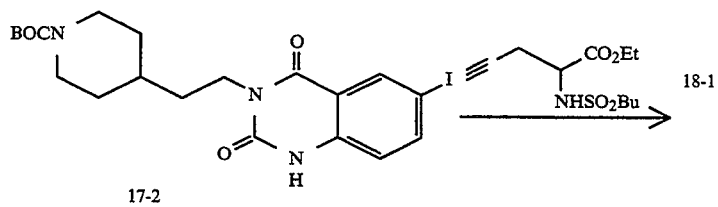
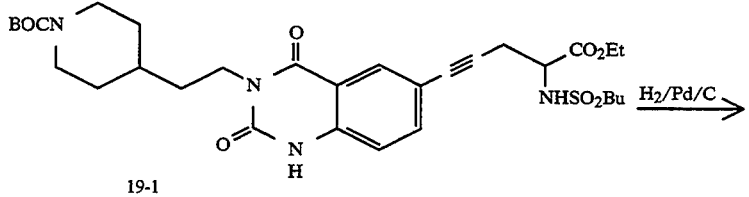
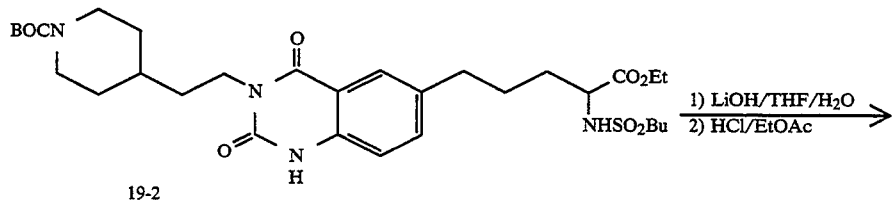
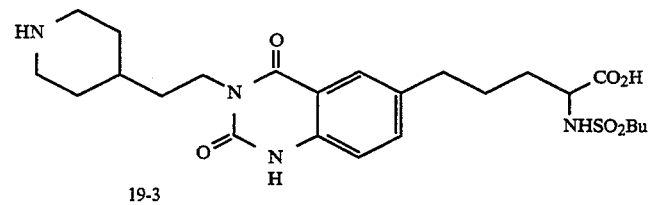
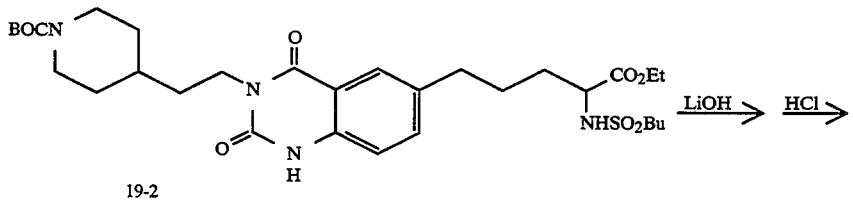
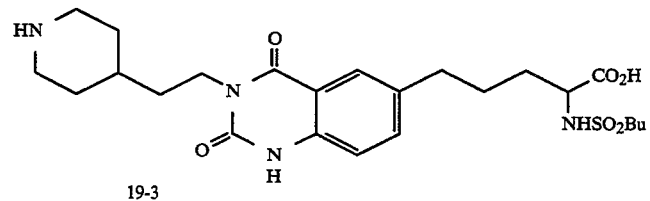

SCHEME 19

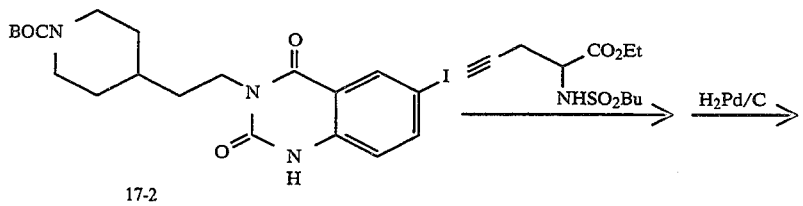

2-Butanesulfonylamino-5-[3-(2-[N-Boc-piperidin-4-yl]-ethyl)-1H,3H-2,4-dioxoquinazolin-6-yl]pentanoic acid, ethyl ester (19-2)

Iodide 17-2 (0.252 g, 0.50 mMol) and acetylene 18-1 (0.137 g, 0.52 mMol) were coupled as described for 18-2 to give 19-1 (0.211 g, 0.33 mMol).

$^1$H NMR (300 MHz, CDCl$_3$): δ9.71 (s, 1H), 7.90 (d, 1H), 7.43 (dd, 1H), 6.85 (d, 1H), 6.07 (d, 1H), 4.42 (m, 1H), 4.30 (m, 2H), 4.09 (m, 4H), 3.13 (t, 2H), 2.98 (t, 2H), 2.72 (t, 2H), 1.80 (m, 4H), 1.66 (m, 2H), 1.48 (s, 9H), 1.33 (t, 3H), 1.20 (m, 2H), 0.95 (t, 3H).

Acetylene 19-1 (0.183 g, 0.29 mMol) was hydrogenated at 50 psi in EtOAc (20 mL)/EtOH (2 mL) using 10% palladium on carbon as the catalyst until reaction complete by $^1$H NMR (CDCl$_3$). The catalyst was filtered off and the solvents were removed in vacuo to give 19-2.

$^1$H NMR (300 MHz, CDCl$_3$): δ10.48 (s, 1H), 7.91 (d, 1H), 7.44 (dd, 1H), 7.08 (d, 1H), 5.31 (d, 1H), 4.23 (m, 2H), 4.09 (m, 4H), 2.99 (t, 2H), 2.70 (m, 4H), 1.25 (s, 9H).

2-Butanesulfonylamino-5-[3-(2-[piperidin-4-yl]ethyl)-1H,3H-2,4-dioxoquinazolin-6-yl]pentanoic acid, hydrochloride salt (19-3)

Ester 19-2 was hydrolyzed as described for 17-5 and purified by trituration in CH$_2$Cl$_2$ to give acid 19-3 as a white solid. The BOC group was removed as described for 17-6 to give 19-4.

$^1$H NMR (300 MHz, D$_2$O): δ7.47 (s, 1H), 7.32 (d, 1H), 6.85 (d, 1H), 3.78 (m, 3H), 3.26 (d, 2H), 2.92 (t, 2H), 2.81 (t, 2H), 2.48 (s, broad, 2H), 1.86 (d, 2H), 1.68–1.39 (m, 8H), 1.38–1.10 (m, 4H), 0.65 (t, 3H).

SCHEME 20

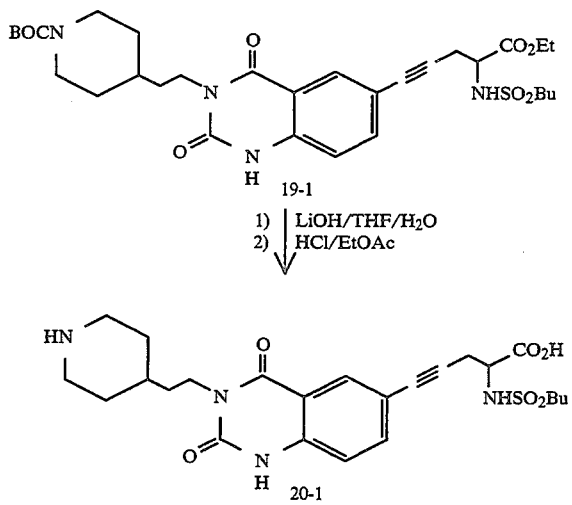

2-Butanesulfonylamino-5-[3-(2-[piperidin-4-yl]ethyl)-1H,3 H-2,4-dioxoquinazolin-6-yl]pent-4-ynoic acid, hydrochloride salt (20-1)

Ester 19-1 was hydrolyzed, purified, and deprotected as described for 19-2 to give 20-1.

$^1$H NMR (300 MHz, D$_2$O): δ7.78 (s, 1H), 7.59 ( (d, 1H), 7.02 (d, 1H), 4.25 (m, 1H), 3.94 (m, 2H), 3.44 (d, broad, 2H), 3.24 (m, 2H), 2.95 (m, 4H), 2.05 (d, broad, 2H), 1.80–1.30 (m, 8H), 0.83 (t, 3H).

SCHEME 21

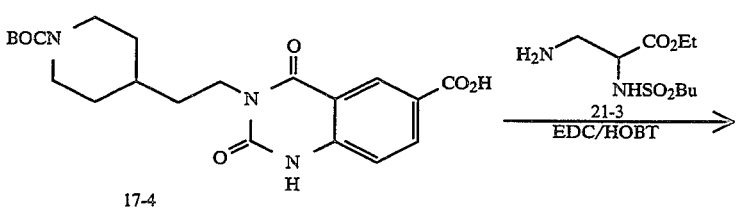

SCHEME 21

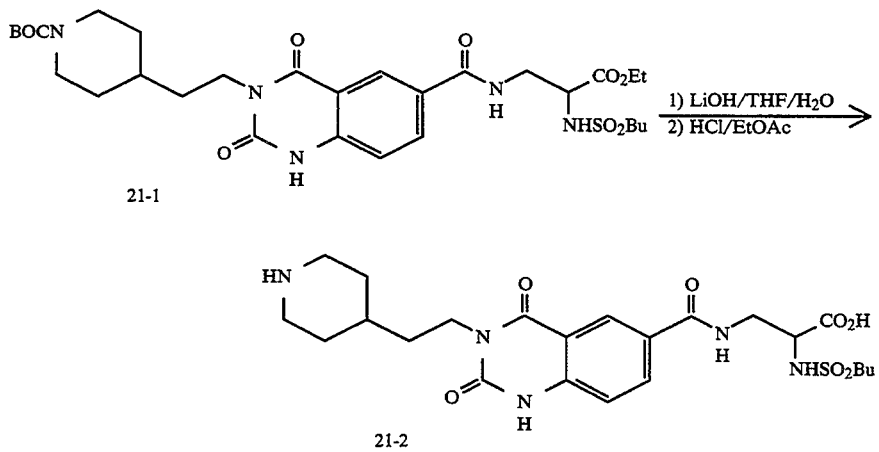

2-Butanesulfonylamino-3-{[3-(2-[piperidin-4-yl]ethyl)-1H,3H-2,4-dioxoquinazolin-6-yl]carbonylamino}-propionic acid, hydrochloride salt (21-2)

Acid 17-4 (0.100 g, 0.24 mMol) and amine 21-3 were coupled as described for 17-1 to give 21-1 (0.155 g, 0.24 mMol) as a white foam.

$^1$H NMR (CDCl$_3$): δ10.18 (s, 1H), 8.39 (d, 1H), 7.99 (dd, 1H), 7.80 (s, broad, 1H), 6.99 (d, 1H), 6.61 (d, 1H), 4.48 (m, 1H), 4.03 (m, 4H), 3.84 (s, 3), 3.10 (t, 2H), 2.68 (t, broad, 2H), 1.81 (m, 2H), 1.72 (d, 2H), 1.55 (m, 2H), 1.45 (s, 9H), 1.26 (t, 2H), 1.12 (m, 2H), 0.91 (t, 3H).

Ester 21-1 (0.155 g, 0.24 mMol) was hydrolyzed and deprotected as described for 17-5 to give 21-2 (0.128 g, 0.20 mMol) as a white solid.

$^1$H NMR (300 MHz, D$_2$O): δ8.15 (s, broad, 1H), 7.85 (d, broad, 1H), 7.05 (d, broad, 1H), 4.18 (m, 1H), 3.84 (t, 2H), 3.73 (m, 1H), 3.47 (m, 1H), 3.27 (d, broad, 2H), 2.98 (t, 2H), 2.80 (m, 2H), 1.49 (m, 6H), 1.28 (m, 2H), 1.11 (m, 4H), 0.59 (t, 3H).

SCHEME 22

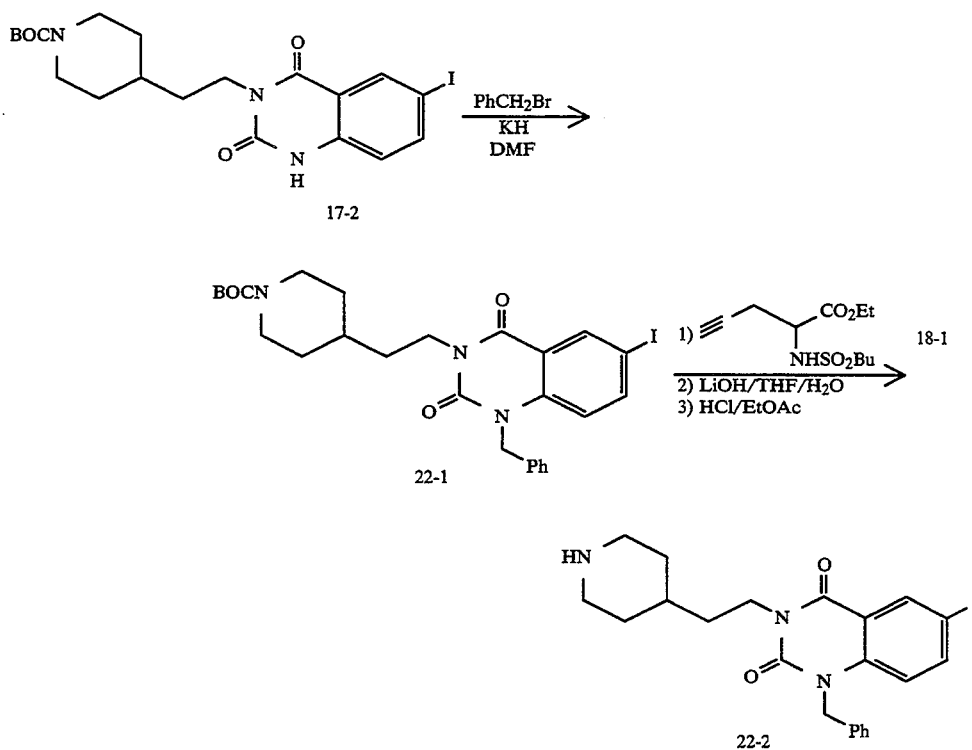

SCHEME 22 -continued

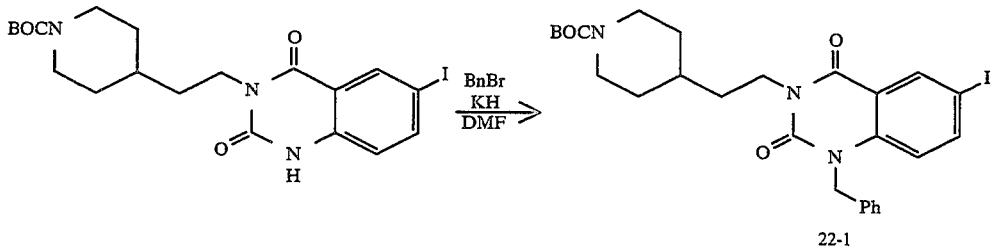

1-Benzyl-3-[2-(N-Boc-piperidin-4-yl)ethyl]-1H,3H-2,4-dioxoquinazolin-6-yl]iodide (22-1)

Potassium hydride (0.120 g, 1.05 mMol) in THF (1 mL) was added dropwise to a DMF (10 mL) solution of 17-2 (0.490 g, 0.98 mMol) and benzyl bromide (0.118 mL, 0.99 mMol) at room temperature. This mixture was stirred under an inert atmosphere for 30 minutes, then quenched with DI water and extracted with EtOAc. The organic layer was washed with 10% citric acid solution, DI water, and brine, dried, and concentrated to give 22-1 (0.674 g) as a white paste. The crude material was purified by triturating in EtOAc (5 mL) for 3 h to give pure 22-1 (0.210 g, 0.36 mMol).

$^1$H NMR (300 MHz, CDCl$_3$): δ8.49 (d, 1H), 7.76 (dd, 1H), 7.36–6.80 (m, 5H), 6.85 (d, 1H), 5.32 (s, 2H), 4.11 (m, 4H), 2.70 (t, 2H), 1.78 (d, 2H), 1.65 (m, 2H), 1.42 (s, 9H).

2-Butanesulfonylamino-5-[1-benzyl-3-(2-[piperidin-4-yl]ethyl)-1H,3 H-2,4-dioxoquinazolin-6-yl]pent-4-ynoic acid, hydrochloride salt (22-2).

Iodide 22-1 (0.505 g, 0.86 mMol) and acetylene 18-1 (0.233 g, 0.89 mMol) were coupled as described for 18-2 to give a brown oil that was purified by silica gel chromatography to yield 22-2 (0.348 g, 0.48 mMol) as a yellow foam.

$^1$H NMR (300 MHz, CDCl$_3$): δ8.18 (d, 1H), 7.50 (dd, 1H), 7.36–7.25 (m, 3H), 7.20 (d, 2H), 7.03 (d, 1H), 5.34 (s, 2H), 5.30 (m, 1H), 4.30 (m, 3H), 4.10 (m, 4H), 3.04 (t, 2H), 2.98 (t, 2H), 2.68 (t, 2H), 1.78 (m, 4H), 1.65 (m, 2H), 1.44 (s, 9H), 1.30 (t, 3H), 1.18 (m, 2H), 0.88 (t, 3H).

22-2 (0.17 g, 0.23 mMol) was hydrolyzed, deprotected, and purified as described for 17-5 to give 2273 (0.082 g) as a white fluffy solid.

$^1$H NMR (300 MHz, DMSO): δ8.37 (s, broad, 2H), 8.01 (d, 1H), 7.62 (m, 6H), 5.35 (s, 2H), 3.98 (m, 3H), 3.00 (t, 2H), 2.97–2.72 (m, 5H), 1.88 (d, broad, 2H), 1.69–1.50 (m, 5H), 1.28 (m, 4H), 1.13 (t, 2H), 0.77 (t, 3H).

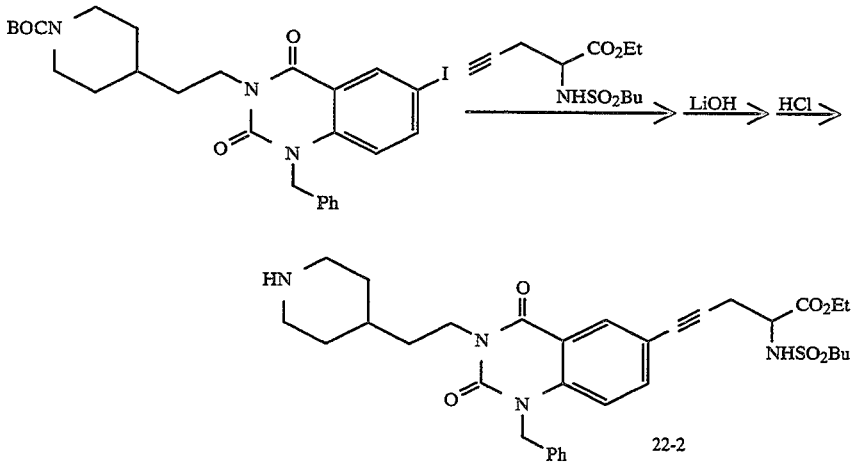

SCHEME 23

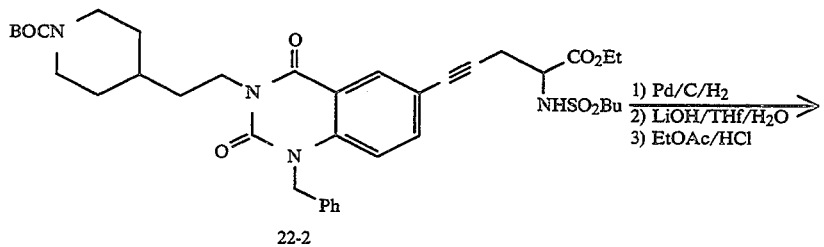

SCHEME 23
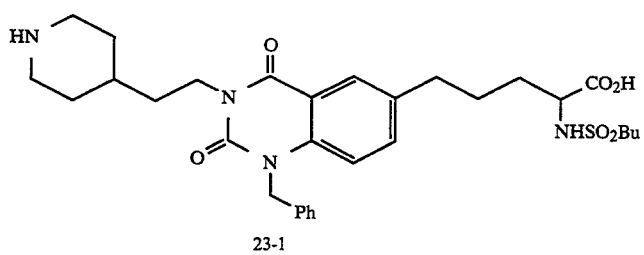
23-1
2-Butanesulfonylamino-5-[1-benzyl-3-(2-piperidin-4-yl]ethyl)-1H,3H-2,4-dioxoquinazolin-6yl]pent-anoic acid, trifluomacetate salt (23-1)
Acetylene 22-2 was reduced, hydrolyzed, deprotected, and purified in the same way as 19-1 to give pure 23-1.
$^1$H NMR (300 MHz, D$_2$O): δ7.67 (d, 1H), 7.10 (m, 6H), 6.89 (d, 1H), 3.90 (m, 3H), 3.68 (m, 1H), 3.24 (d, broad, 2H), 2.79 (m, 4H), 2.38 (m, 2H), 1.83 (d, broad, 2H), 1.60–1.20 (m, 10H), 1.10 (m, 2H), 0.59. (t, 3H).
SCHEME 24
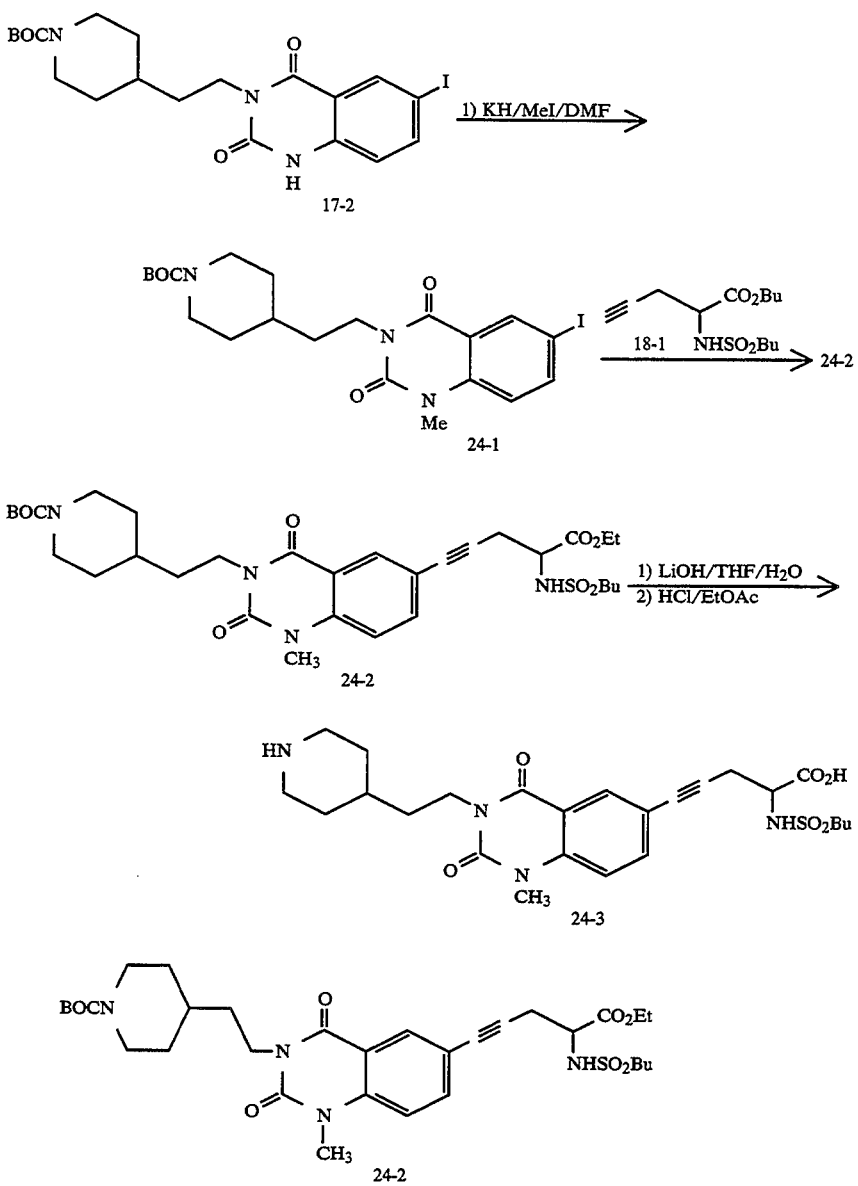

2-Butanesulfonylamino-5-[1-Methyl-3-(2-N-Boc-piperidin-4-yl]ethyl)-1H,3H-2,4-dioxoquinazolin-6-yl]pent-4-ynoic acid, ethyl ester (24-2)

Replacing benzyl bromide with methyl iodide, 17-2 (0.506 g, 1.01 mmol) was methylated as described for 22-1 to give, after trituration with Et$_2$O, 24-1. This iodide was coupled with acetylene 18-1 (0.439 g, 1.68 mmol) as described for 18-2 to give 24-2.

$^1$H NMR (300 MHz, CDCl$_3$): δ8.20 (d, 1H) 7.66 (dd, 1H), 7.14 (d, 1H), 5.13 (d, 1H), 4.32 (m, 3H), 4.10 (m, 4H), 3.59 (s, 3H), 3.05 (m, 4H), 2.70 (t, broad, 2H), 1.80 (m, 4H), 1.62 (m, 3H), 1.46 (s, 9H), 0.92 (t, 3H).

$^1$H NMR (300 MHz, D$_2$O) δ7.50 (d, 1H), 7.39 (dd, 1H), 6.98 (d, 1H), 4.16 (t, 1H), 3.72 (s, broad, 2H), 3.28 (m, 5H), 3.10 (t, 2H), 2.85 (m, 4H), 1.91 (d, 2H), 0.70 (t, 3H).

SCHEME 25

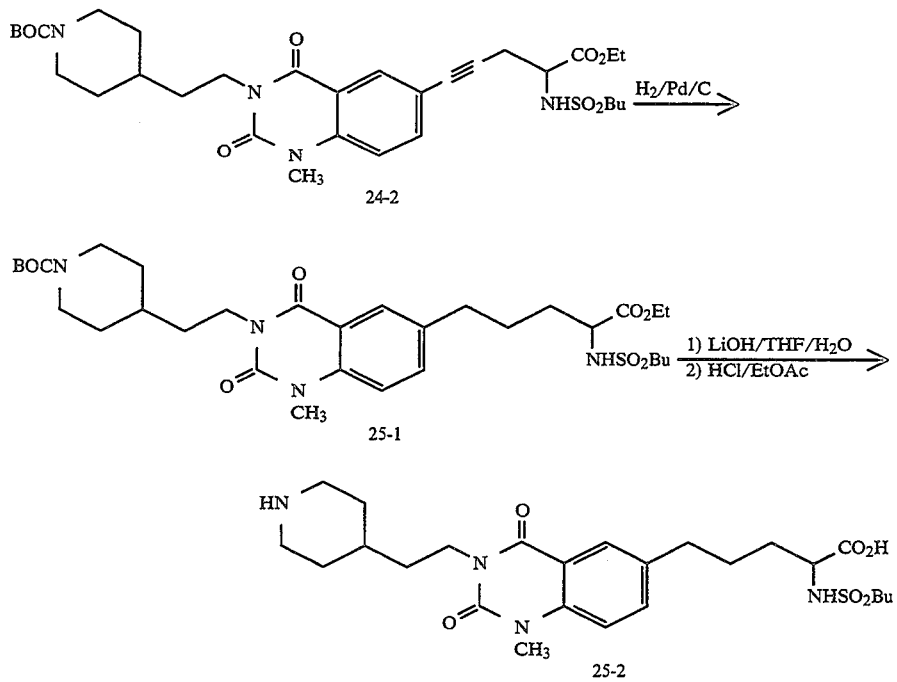

2-Butanesulfonylamino-5-[1-Methyl-3-(2-[piperidin-4-yl]ethyl)-1H,3H-2,4-dioxoquinazolin-6-yl]pent-anoic acid, hydrochloride salt (25-2)

Acetylene 24-2 (0.190 g, 0.29 mMol) was hydrogenated as described for 19-1 to give 25-1 (0.176 g, 0.27 mMol) as a pale yellow oil.

$^1$H NMR 9300 MHz, CDCl$_3$): δ7.99 (d, 1H), 7.51 (dd, 1H), 7.14 (d, 1H), 4.96 (d, 1H), 4.23 (q, 2H), 4.10 (m, 5H), 3.60 (s, 3H), 2.97 (m, 2H), 2.71 (m, 4H), 1.79 (m, 7H), 1.62 (m, 2H), 1.45 (s, 9H), 1.25 (m, 5H), 0.94 (t, 3H).

25-1 was then hydrolyzed and deprotected as described f19-1 to give 25-2 (0.158 g) as a white solid. 1H NMR (CDCl$_3$): δ7.85 (d, 1H), 7.65 (dd, 1H), 7.32 (d,

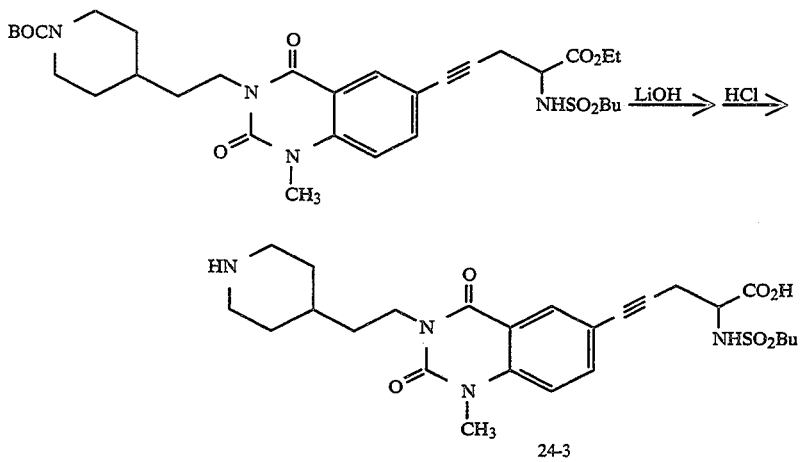

2-Butanesulfonylamino-5-[1-methyl-3-(2-piperidin-4-yl]ethyl)-1H,3 H-2,4-dioxoquinazolin-6-yl]pent-4-ynoic acid, hydrochloride salt (24-3)

24-2 was hydolyzed and deprotected as described for 19-1 to give clean 24-3 (0.112 g) as a white solid.

1H), 4.00 (m, 3H), 3.51 (s, 3H), 3.42 (d, 2H), 3.10 (t, 2H), 2.98 (m, 2H), 2.72 (m, 2H), 2.10 (d, 2H), 1.70 (m, 8H), 1.39 (m, 5H), 0.83 (t, 3H).

was quenched with 10% citric acid solution and extracted with EtOAc. The aqueous layer was basified and extracted with EtOAc. This, organic layer was

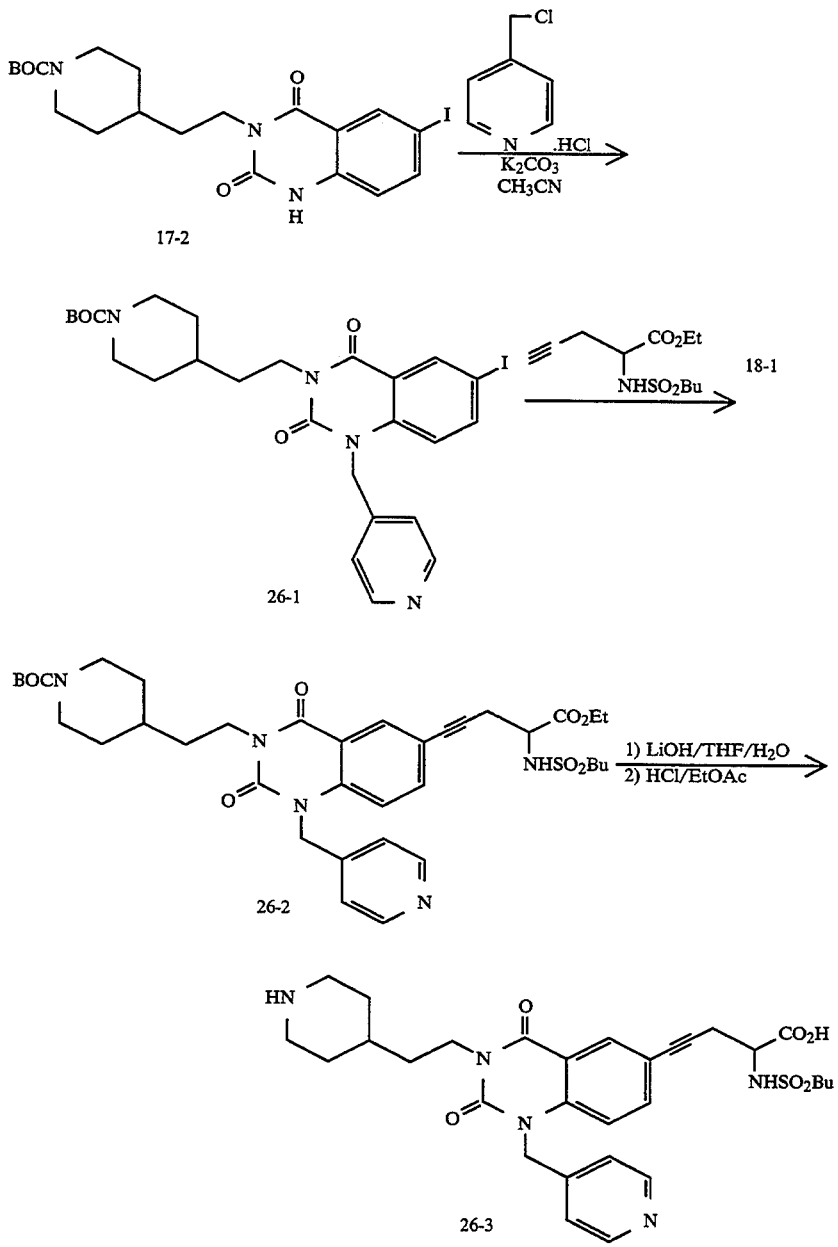

1-(4-Pyridylmethyl)-3-[2-(N-Boc-piperidin-4-yl)ethyl]-1H,3H-2,4-dioxaquinazolin-6-yl iodide (26-1)

Iodide 17-2 (0.70 g, 0.14 mMol), 4-picolyl chloride hydrochloride (0.322 g, 0.20 mMol), and powdered potassium carbonate (0.466 g, 0.34 mMol) were heated to +80° C. in acetonitrile (45 mL) for 4 h. The reaction concentrated and triturated with ether to yield 26-1 (0.6811 g, 0.12 mMol) as a white solid.

$^1$H NMR (300 MHz, DMSO): δ8.51 (d, 2H), 8.29 (d, 1H), 7.93 (dd, 1H), 7.31 (d, 2H), 7.01 (d, 1H), 5.38 (s, 2H), 3.98 (d, 2H), 3.89 (d, 2H), 1.70 (d, 2H), 1.50 (m, 4H), 1.38 (s, 9H), 1.00 (m, 3H), 0.80 (m, 4H).

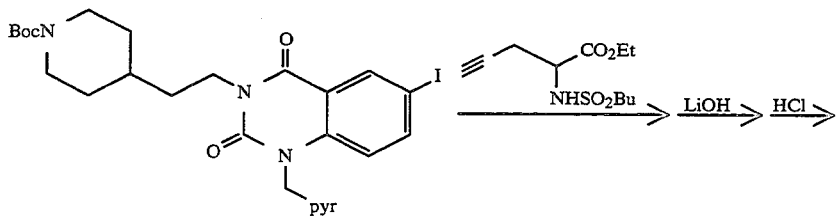

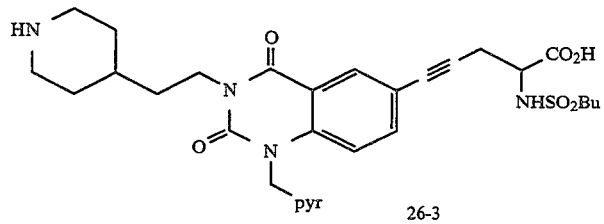

2-Butanesulfonylamino-5-[1-pyridylmethyl-3-(2-piperidin-4-yl]ethyl)-1H,3H-2,4-dioxoquinazolin-6-yl]pent-4-ynoic acid, trifluoroacetate salt (26-3)

26-1 (0.4224 g, 0.72 mMol) was coupled with acetylene 18-1 (0.243 g, 0.93 mMol) as described for 18-2 to give 26-2 (0.32 g, 0.50 mMol) as a yellow foam.

$^1$H NMR (300 MHz, CDCl$_3$): 8.59 (d, 2H), 8.23 (d, 1H), 7.54 (dd, 1H), 7.12 (d, 2H), 6.89 (d, 1H), 5.35 (s, broad, 2H), 5.11 (d, 1H), 4.30 (m, 2H), 4.12 (m, 4H), 3.06 (m, 4H), 3.00 (t, 2H), 2.70 (t, 2H), 1.79 (m, 4H), 1.68 (m, 2H), 1.59 (s, 2H), 1.46 (s, 9H), 0.91 (t, 3H).

26-2 was hydrolyzed and deprotected as described for Y—Y, then purified by triturating in EtOAc/CH$_2$Cl$_2$ to give clean 26-3.

$^1$H NMR (D$_2$O): δ8.56 (d, 1H), 8.02 (d, 1H), 7.78 (d, 2H), 7.54 (dd, 1H), 6.96 (d, 1H), 5.55 (s, 2H), 3.98 (m, 3H), 3.25 (d, 2H), 3.05 (t, 2H), 2.79 (m, 5H), 1.89 (d, 2H), 1.53 (m, 5H), 1.30 (m, 2H), 1.15 (m, 2H), 0.61 (t, 3H).

SCHEME 27

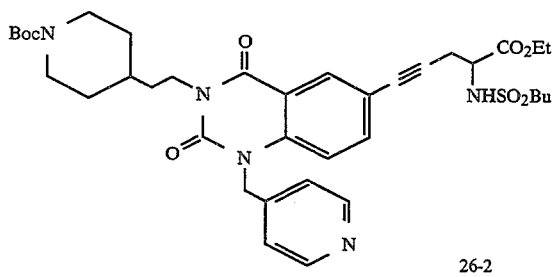

1) H$_2$/Pd/C
2) LiOH/THF/H$_2$O
3) HCl/EtOAc

-continued SCHEME 27

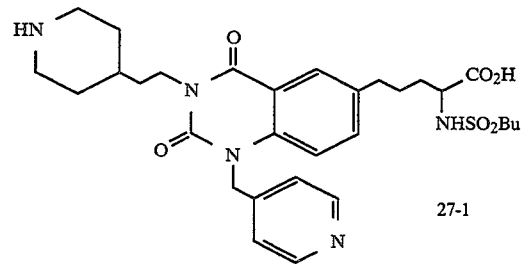

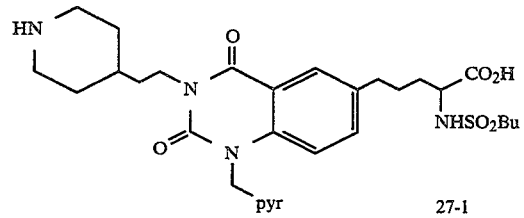

2-Butanesulfonylamino-5-[1-(4-pyridylmethyl)-3-(2-piperidin-4-yl]ethyl)-1H,3H-2,4-dioxoquinazolin-6-yl]pent-anoic acid, trifluoroacetate salt (27-1)

Acetylene 26-2 was hydrogenated and deprotected in the same way as 19-1 to afford 27-1.

$^1$H NMR (D$_2$O): 8.72 (d, 2H), 8.07 (d, 1H), 7.94 (d, 2H), 7.61 (dd, 1H), 7.13 (d, 1H), 5.83 (s, 2H), 4.13 (m, 2H), 3.89 (s, broad, 1H), 3.42 (d, 2H), 3.10 (t, 2H), 2.99 (t, 2H), 2.78 (m, 2H), 2.06 (d, 2H), 1.70 (m, 4H), 0.83 (t, 3H).

SCHEME 28

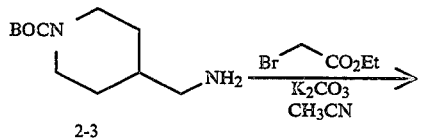

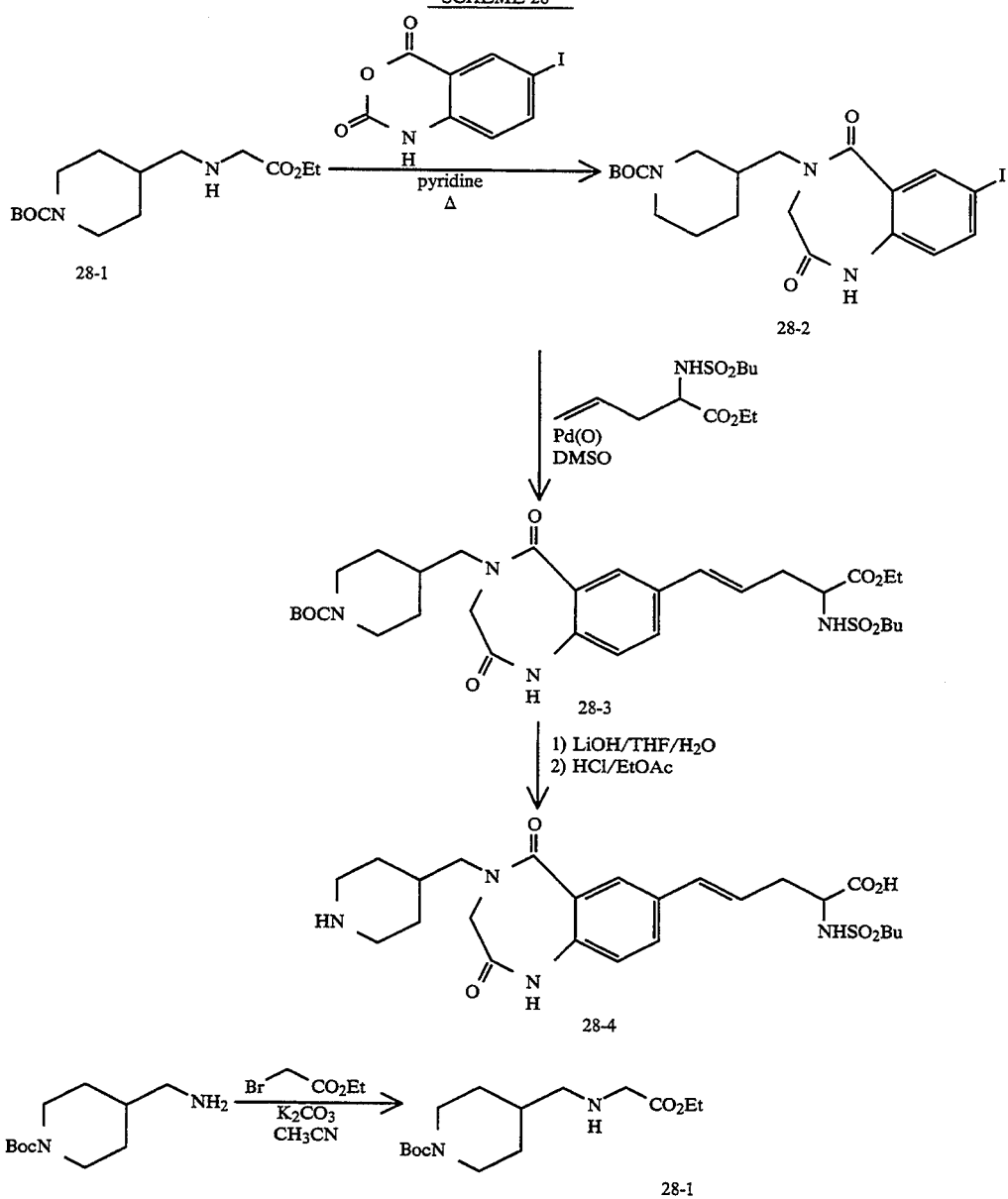

N-(N'-Boc-Piperidin-4-ylmethyl)glycine, ethyl ester (28-1)

A mixture of amine 2-3 (8.714 g) and potassium carbonate (10.55 g) is $CH_3CN$ (100 mL) was cooled to 0° C., then ethyl bromo acetate (4.5 mL) added dropwise. Stirred at RT overnight. Remove acetonitrile in vacuo and add water and 10% citric acid soln. and extract with EtOAc. Wash organics with water, bicarb, and brine. Solvent evaporated and crude product purified by flash column chromatography to give 28-1.

$^1H$ 4.18 (m, 4H), 2.70 (t, 2H), 2.50 (d, 2H), 1.72 (d, broad, 2H), 1.62 (m, 1H), 1.46 (s, 9H), 1.28 (t, 3H), 1.13 (m, 2H)

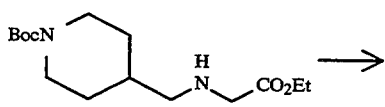

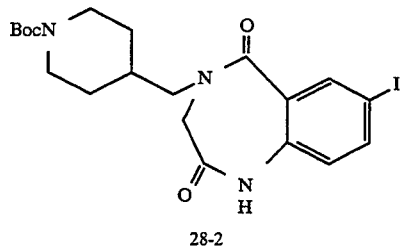

7-Iodo-4-[(N-Boc-piperidin-4-yl)methyl]-1H-1,4-dioxobenzodiazepine (28-2)

A solution of amine 28-1 (2.62 g) and 4-iodoisatoic anhydride (2.52 g) in 55 ml of dry pyridine was heated to reflux for 18 h. Concentration and purification by flash column chromatography (EtOAc/MeOH) afforded 2.81 g of 28.2 as a yellow foam. M.S. (Pos FAB) 444 M+ +1-56 (loss of b-butyl).

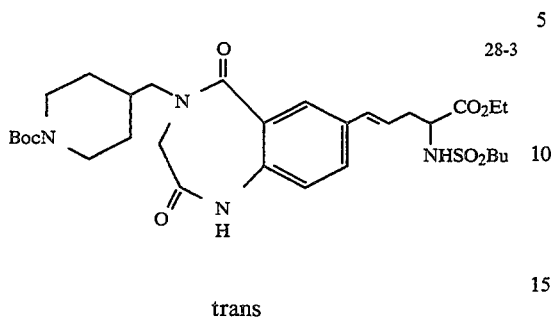

trans
2-Butanesulfonylamino-5-[4-(N-Boc-piperidin-4-yl-methyl)-1H-1,4-dioxobenzodiazepin-7-yl]pent-4-enoic acid, ethyl ester (28-3)

Aryl iodide 28-2 (0.26 g, 0.52 mMol) and olefin (1.125 g, 0.48 mMol) (prepared from allyl glycine in the same way as described for 18-1) were heated to 85° C. in DMSO (10 mL) in the presence of bis(di benzylidendacetone) palladium and his (diphenylphosphino)-1,2-ethane for 24 h. Quenched with water and extracted in EtOAc. The organic layer was washed in DI water, 10% citric acid solution, DI water, bicarb, and brine, dried (MgSO4), and concentrated to give 0.345 g as brown oil, which was purified by silica gel chromatography to yield 28-3 (0.211 g).

¹H (CD3OD) 8.08 (d, 1H), 7.54 (dd, 1H), 7.21 (d, 1H), 6.55 (d, J=15.87 Hz, 1H), 6.34 (dt, 1H), 4.13 (m, 8H), 3.01 (t, 2H), 1.05 (d, 2H), 0.90 (t, 3H).

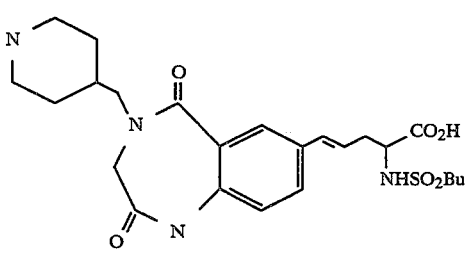

trans
2-Butanesulfonylamino-5-[4-(piperidin-4-yl-methyl)-1H.-1,4-dioxobenzodiazepin-7-yl]pent-4-enoic acid, trifluoroacetate salt (28-4)

Olefin 28-3 was deprotected as described for 17-5 to give amino acid 28-4.

NMR (300 MHz, D2O) 8.4 (d, 1H), 8.05 (d, 1H), 7.77 (dd, 1H), 6.48 (d, 1H), 6.20 (dt, 1H), 4.0–4.2 (m, 6H), 33 (m, 3H), 3.0 (t, 2H), 2.4–2.8 (m, 5H), 0.9–1.8 (m, 2H).

SCHEME 29

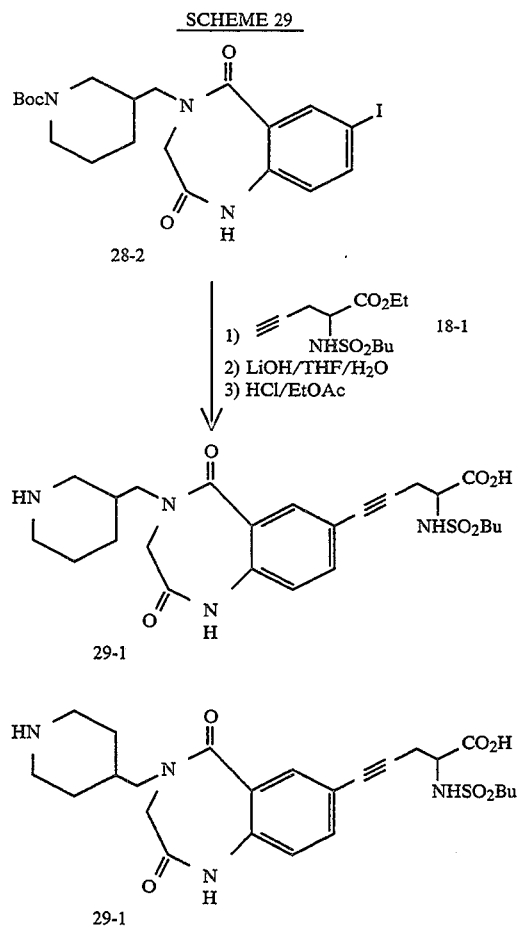

2-Butanesulfonylamino-5-[4-(piperidin-4-ylmethyl)-1H-1',4-dioxobenzodiazepin-7-yl]pent-4-ynoic acid, trifluoroacetate (29-1)

Iodide 28-2 was coupled with acetylene 18-1 and the resulting product deprotected as described for 17-5, to afford acetylene 29-1. ¹H (D2O): 8.28 (d, broad, 1H) 8.06 (s, broad, 1H), 7.66 (d, broad, 1H), 4.27 (m, 1H), 4.18 (m, 2H), 3.51–3.7 (m, 4H), 3.22 (m, 2H), 2.98 (m, 4H), 2.03 (m, 3H), 1.75 (m, 2H), 1.51 (m, 2H), 1.32 (m, 2H), 0.81 (t, 3H).

SCHEME 30

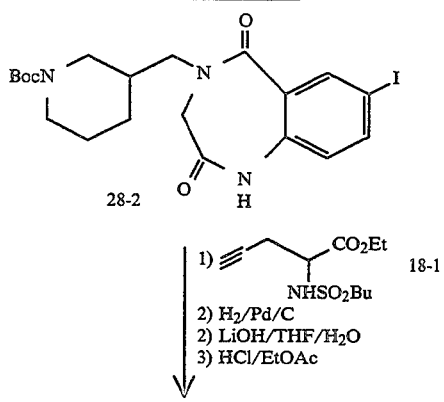

-continued
SCHEME 30

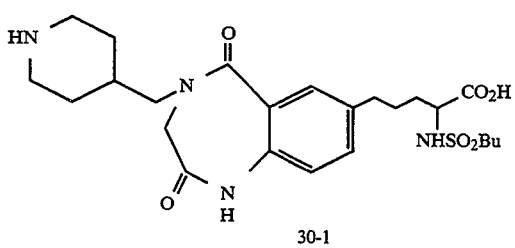
30-1

2-Butanesulfonylamino-5-[4-(piperidin-4-ylmethyl)-1H-1,4-dioxobenzodiazepin-7-yl]pentanoic acid, trifluoroacetate salt (30-1)

Iodide 28-2 was coupled with acetylene 18-1 as described in 18-2 and the product hydrogenated and deprotected as described in 19-1 to afford 30-1.

NMR (300 MHz, D$_2$O), 7.80 (d, 1H), 7.43 (dd, 1H), 7.14 (d, 1H), 4.11 (s, 2H), 3.9 (m, 1H), 3.1–3.4 (m, 4H), 2.95 (t, 2H), 2.5–2.9 (m, 4H) 1.1–1.95 (m, 13H), 0.66 (t, 3H). MS (Pos FAB) 553 (M$^+$+1+CO$_2$)

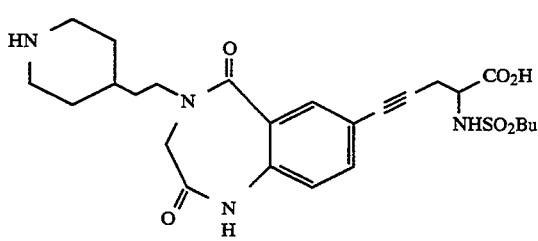
31-1

2-Butanesulfonylamino-5-[4-[2-(piperidin-4-yl)ethyl]-1H-1,4-dioxobenzodizepin-7-yl]pent-4-ynoic acid, trifluoroacetate salt (31-1)

31-1 was prepared analogously to 29-1, with substitution of N-(BOC-piperidinylethyl)glycine ethyl ester for N-(BOC-piperdinemethyl)glycine ethyl ester.

NMR (300 MHz, D$_2$O) 7.8 (d, 1H), 7.60 (dd, 1H), 7.22 (d, 1H), 4.19 (dd, 1H), 4.10 (s, 2H), 3.0–3.6 (m, 6H), 2.7–2.92 (m, 4H), 1.0–1.9 (m, 11H), 0.61 (t, 3H).

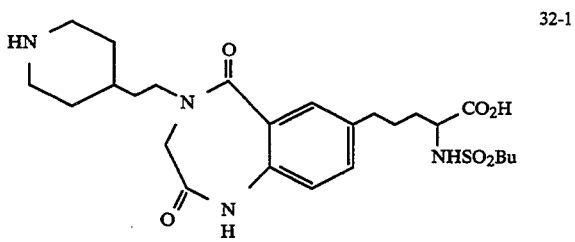
32-1

2-Butanesulfonylamino-5-[4-[2-piperidin-4-yl)ethyl]-1H-1,4-dioxobenzodiazepin-7-yl]pentanoic acid, trifluoroacetete salt (32-1)

Compound 32-1 was prepared in the same way as 30-1, but substituting N-(Boc piperidinylethyl) glycine ethyl ester for N-Boc-piperdinylethyl) glycine ethyl ester.

NMR (300 MHz, D$_2$O) δ7.82 (d, 1H), 7.46 (dd, 1H), 7.16 (d, 1H), 4.10 (s, 2H), 3.84 (m, 1H), 3.2–3.6 (m, 4H), 2.96 (t, 2H), 2.5–2.9 (m, 4H), 1.8 (m, 2H), 1.1–1.8 (m, 13H), 0.69 (t, 3H).

SCHEME 37

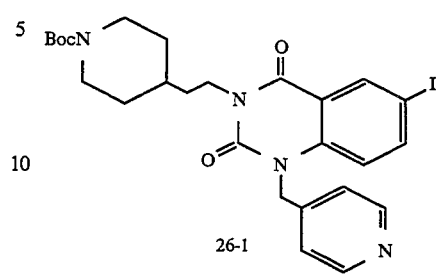
26-1

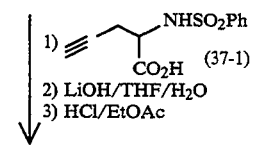
1)
2) LiOH/THF/H$_2$O
3) HCl/EtOAc

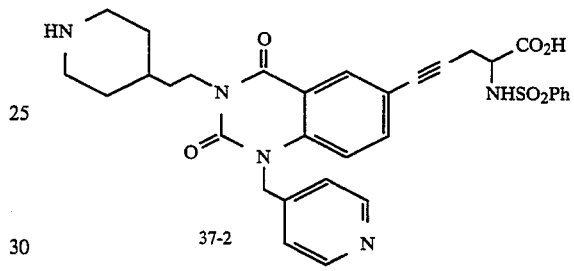
37-2

2-Benzenesulfonylamino-5-[1-(pyridin-4-yl)methyl-3-(2-piperidin-4yl)ethyl-1H,3H-2,4-dioxoquinazolin-6-yl]pent-4-ynoic acid (37-2).

37-2 was prepared from iodide 26-1 using the procedures described for Example 26 but replacing n-butanesulfonylacetylene 18-1 with the analogously prepared bezenesulfonylacetylene 37-1.

NMR (300 MHz, D$_2$O) 8.55 (d, 2H), 7.75–7.85 (m, 3H), 7.67 (d, 1H), 7.20–7.45 (m, 5H), 6.93 (d, 1H), 5.55 (s, 2H), 3.9–4 (m, 3H), 3.75 (brd, 2H), 2.81 (brd, 2H), 2.65 (m, 2H), 1.87 (brd, 2H), 1.2–1.6 (m, 5H).

SCHEME 38

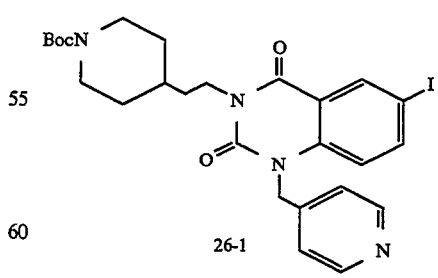
26-1

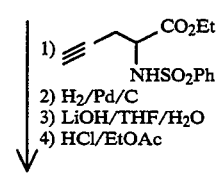
1)
2) H$_2$/Pd/C
3) LiOH/THF/H$_2$O
4) HCl/EtOAc

-continued
SCHEME 38

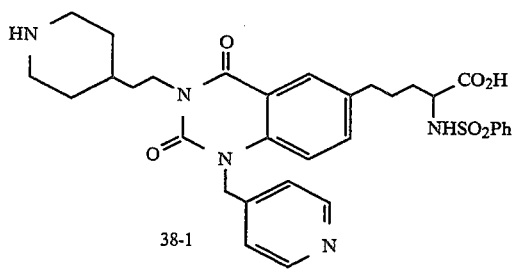

2-Benzenesulfonylamino-5-[1-(pyridin-4-yl)methyl-3-[2-piperidin-4-yl]ethyl)-1H,3H-2,4-dioxoquinazolin-6-yl]-pentanoic acid, trifluoroacetate salt (38-1)

38-1 was prepared from iodide 26-1 using the procedures described for Example 27, but replacing n-butanesulfonylacetylene 18-1 with the analogously prepared bezenesulfonylacetylene 37-1.

NMR (300 MHZ, D20) 8.58 (D, 2H), 7.78 (M, 3H), 7.61 (D, 2H) 7.25–7.45 (M, 3H), 6.75 (D, 2H), 5.56 (S, 2H), 3.95 (M, 2H), 3.55 (M, 1H), 3.26 (BD, 2H), 2.7 (BRD, 2H), 2.42 (M, 2H), 1.87 (BRD, 2H), 1.2–1.6 (M, 9H).

What is claimed is:

1. A compound of the following formula:

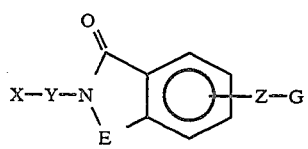

wherein
G is

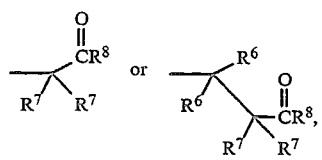

E is —(CHR$^1$)$_m$—J—;
m is zero or one;
J is

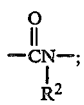

X is a 6-membered monocyclic nonaromatic ring system containing a nitrogen atom and either unsubstituted or substituted with C$_{1-10}$ alkyl, aryl C$_{0-8}$ alkyl, oxo, thio, amino CO$_{0-8}$ alkyl, C$_{1-3}$ acylamino C$_{0-8}$ alkyl, C$_{1-6}$ alkylamino C$_{0-8}$ alkyl, C$_{1-6}$ dialkylamino C$_{0-8}$ alkyl, C$_{1-4}$ alkoxy C$_{0-6}$ alkyl, carboxy C$_{0-6}$ alkyl, C$_{1-3}$ alkoxycarbonyl C$_{0-6}$ alkyl, carboxy C$_{0-6}$ alkyloxy, hydroxy C$_{0-6}$ alkyl;

Y is C$_{0-8}$ alkyl, C$_{0-8}$ alkyl—NR$^3$—CO—C$_{0-8}$ alkyl, C$_{0-8}$ alkyl—CONR$^3$—C$_{0-8}$ alkyl, C$_{0-8}$ alkyl—O—C$_{0-8}$ alkyl, C$_{0-8}$ alkyl-S(O$_n$)—C$_{0-8}$ alkyl, or C$_{0-8}$ alkyl—SO$_2$—NR$^3$—C$_{0-8}$ alkyl, C$_{0-8}$ alkyl—NR$^3$—SO$_2$—C$_{0-8}$ alkyl, or C$_{1-8}$ alkyl—CO—C$_{0-8}$ alkyl;

Z is

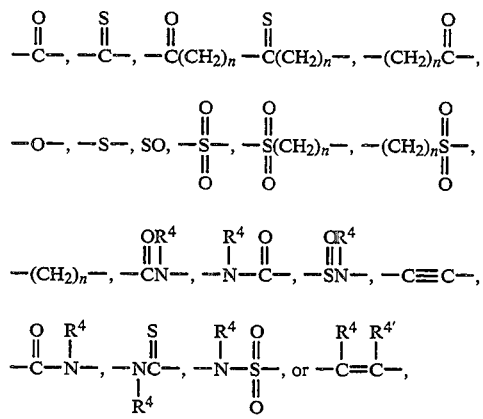

wherein n is 0–6;

R$^1$, R$^2$, R$^3$, R$^4$, and R$^{4'}$, are independently selected from the group consisting of hydrogen, C$_{1-10}$ alkyl, aryl C$_{0-8}$ alkyl, oxo, thio, amino CO$_{0-8}$ alkyl, C$_{1-3}$ acylamino C$_{0-8}$ alkyl, C$_{1-6}$ alkylamino C$_{0-8}$ alkyl, C$_{1-6}$ dialkylamino C$_{0-8}$ alkyl, C$_{1-4}$ alkoxy C$_{0-6}$ alkyl, carboxy C$_{0-6}$ alkyl, C$_{1-3}$ alkoxycarbonyl C$_{0-6}$ alkyl, carboxy C$_{0-6}$ alkyloxy, hydroxy C$_{0-6}$ alkyl, R$^6$ is hydrogen, C$_{1-8}$ alkyl, aryl C$_{0-6}$ alkyl, C$_{3-8}$ cycloalkyl C$_{0-6}$ alkyl, C$_{0-6}$ alkylcarboxy C$_{0-6}$ alkyl, carboxy C$_{0-6}$ alkyl, C$_{1-4}$ alkyloxy C$_{0-6}$ alkyl, hydroxy C$_{0-6}$ alkyl, provided that any of which groups may be substituted or unsubstituted independently with R$^1$ or R$^2$, and provided that, when two R$^6$ groups are attached to the same carbon, they may be the same or different;

R$^7$ is hydrogen, fluorine C$_{1-8}$ alkyl, C$_{3-8}$ cycloalkyl, aryl C$_{0-6}$ alkyl, C$_{0-6}$ alkylamino C$_{0-6}$ alkyl, C$_{0-6}$ dialkylamino C$_{0-6}$ alkyl, C$_{1-8}$ alkylsulfonylamino C$_{0-6}$ alkyl, aryl C$_{0-6}$ alkylsulfonylamino C$_{0-6}$ alkyl, C$_{1-8}$ alkyloxycarbonylamino C$_{0-8}$-alkyl, aryl C$_{0-8}$ alkyloxycarbonylamino C$_{0-8}$ alkyl, C$_{1-8}$ alkylcarbonylamino C$_{0-6}$ alkyl, aryl C$_{0-6}$ alkylcarbonylamino C$_{0-6}$ alkyl, C$_{0-8}$ alkylaminocarbonylamino C$_{0-6}$ alkyl, aryl C$_{0-8}$ alkylaminocarbonylamino C$_{0-6}$ alkyl, C$_{1-6}$ alkylsulfonyl C$_{0-6}$ alkyl, aryl C$_{0-6}$ alkylsulfonyl C$_{0-6}$ alkyl, C$_{1-6}$ alkylcarbonyl C$_{0-6}$ alkyl aryl C$_{0-6}$ alkylcarbonyl C$_{0-6}$ alkyl, C$_{1-6}$ alkylthiocarbonylamino C$_{0-6}$ alkyl, or aryl C$_{0-6}$ alkylthiocarbonylamino C$_{0-6}$ alkyl wherein groups may be unsubstituted or substituted with one or more substituents selected from R$^1$ and R$^2$, and provided that when two R$^7$ groups are attached to the same carbon atom, they may be the same or different; and R$^8$ is hydroxy, C$_{1-8}$ alkyloxy, aryl C$_{0-6}$ alkyloxy, C$_{1-8}$ alkylcarbonyloxy C$_{1-4}$ alkyloxy, aryl C$_{1-8}$ alkylcarbonyloxy C$_{1-4}$ alkyloxy, or proline joined by an amide linkage and wherein the carboxylic acid moiety of said proline is as the free acid or is esterified by C$_{1-6}$ alkyl.

2. A compound of claim 1 wherein
E is —(CHR$^1$)$_m$—J—;
m is zero;
J is

R² is H.

3. A compound of claim 17 wherein
E is —(CHR¹)$_m$—J—;
m is zero;
J is

R² is $C_{1-10}$ alkyl, aryl $C_{0-8}$ alkyl, oxo, thio, amino $C_{0-8}$ alkyl, $C_{1-3}$ acylamino $C_{0-8}$ alkyl, $C_{1-6}$ alkylamino $C_{0-8}$ alkyl, $C_{1-6}$ dialkylamino $C_{0-8}$ alkyl, $C_{1-4}$ alkoxy $C_{0-6}$ alkyl, carboxy $C_{0-6}$ alkyl, $C_{1-3}$ alkoxycarbonyl $C_{0-6}$ alkyl, carboxy $C_{0-6}$ alkyloxy, hydroxy $C_{0-6}$ alkyl, 4. A compound of claim 1 wherein
E is —(CHR¹)$_m$—J—;
m is one; and
J is

5. A compound of claim 2 selected from the group consisting of:

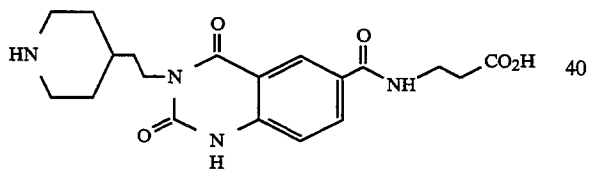

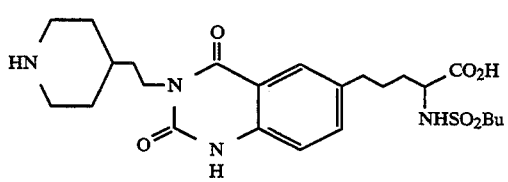

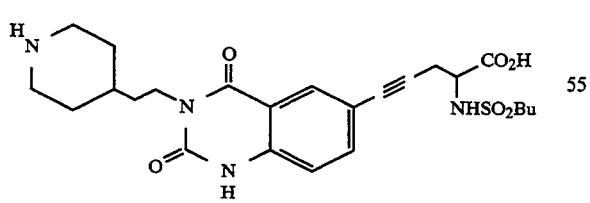

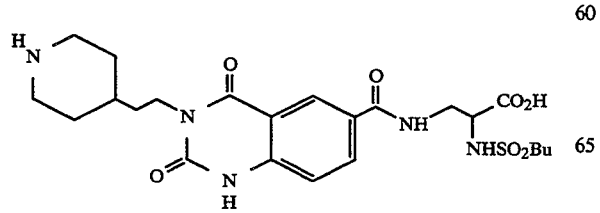

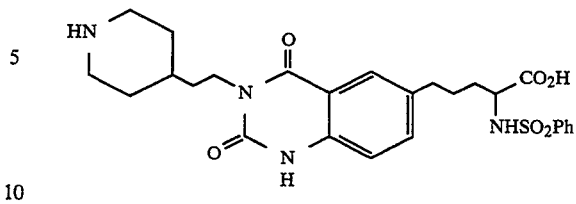

6. A compound of claim 3 selected from the group consisting of:

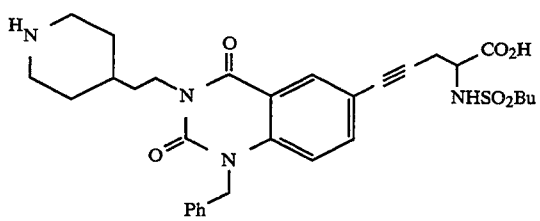

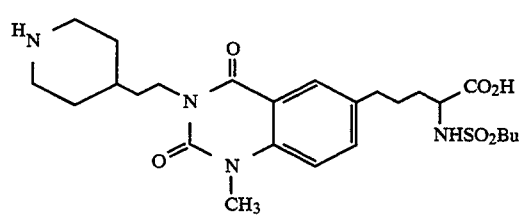

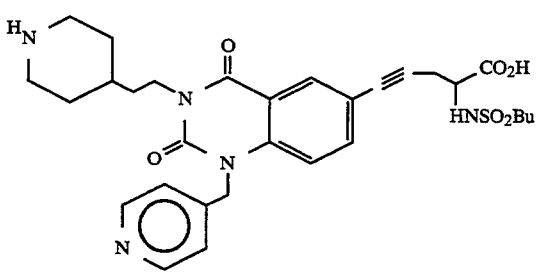

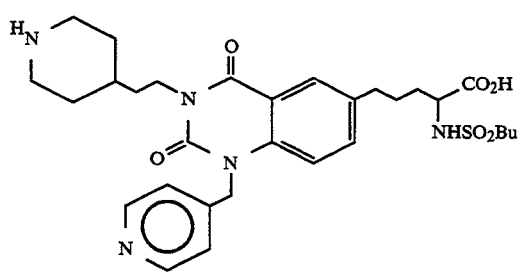

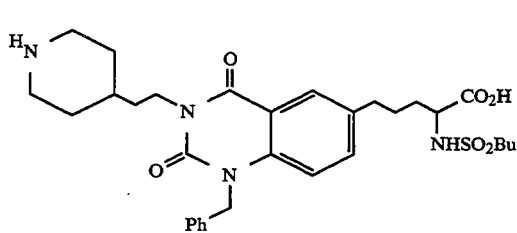

-continued

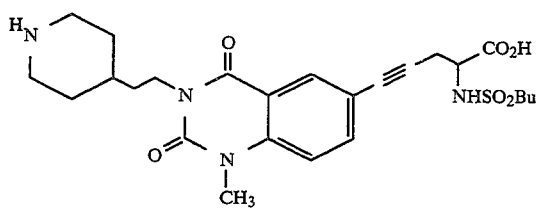

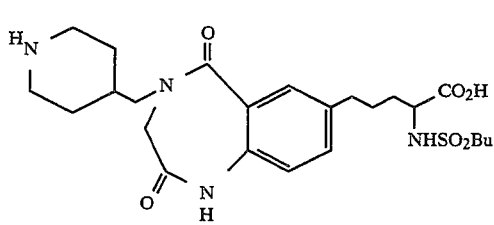

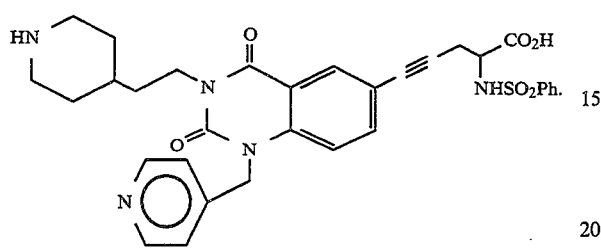

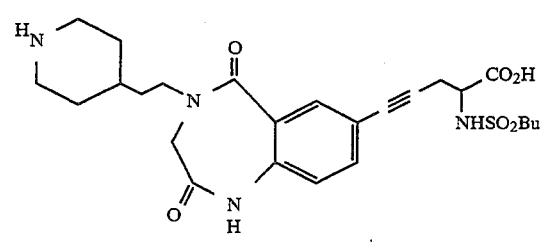

7. A compound of claim 4 selected from the group consisting of:

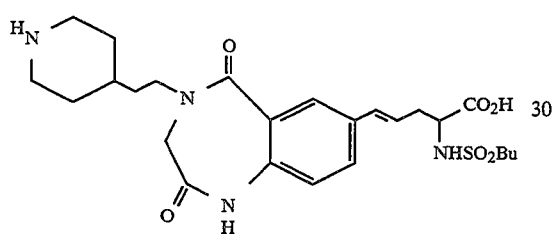

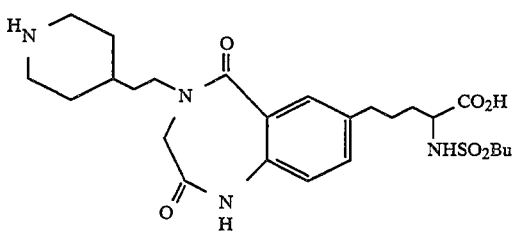

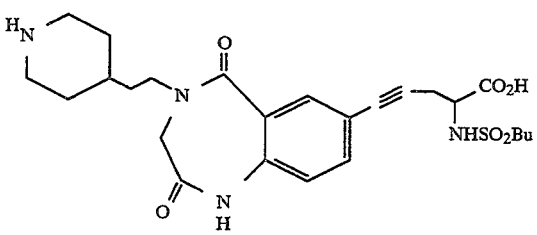

8. A composition for inhibiting the binding of fibrinogen, to blood platelets in a mammal, comprising a compound of claim 1 and a pharmaceutically acceptable carrier.

9. A composition for inhibiting the aggregation; of blood platelets in a mammal, comprising a compound of claim 1 and a pharmaceutically acceptable carrier.

10. A method for inhibiting the binding of fibrinogen to blood platelets in a mammal, comprising administering to the mammal a composition of claim 9.

11. A method for inhibiting the aggregation of blood platelets in a mammal, comprising administering to the mammal the composition of claim 9.

* * * * *